(12) United States Patent
Calzone et al.

(10) Patent No.: US 11,242,398 B2
(45) Date of Patent: Feb. 8, 2022

(54) ANTI-OX40 ANTIBODIES AND METHODS OF ACTIVATING OX40

(71) Applicant: REMD Biotherapeutics, Inc., Camarillo, CA (US)

(72) Inventors: Frank J Calzone, Westlake Village, CA (US); Hai Yan, Thousand Oaks, CA (US); John Zhang, Camarillo, CA (US)

(73) Assignee: REMD Biotherapeutics, Inc., Camarillo, CA (US)

( * ) Notice: Subject to any disclaimer, the term of this patent is extended or adjusted under 35 U.S.C. 154(b) by 161 days.

(21) Appl. No.: 16/635,806

(22) PCT Filed: Aug. 1, 2018

(86) PCT No.: PCT/US2018/044882
§ 371 (c)(1),
(2) Date: Jan. 31, 2020

(87) PCT Pub. No.: WO2019/028182
PCT Pub. Date: Feb. 7, 2019

(65) Prior Publication Data
US 2021/0024640 A1  Jan. 28, 2021

Related U.S. Application Data

(60) Provisional application No. 62/539,946, filed on Aug. 1, 2017.

(51) Int. Cl.
*C07K 16/18* (2006.01)
*A61K 39/395* (2006.01)
*C07K 16/28* (2006.01)

(52) U.S. Cl.
CPC .... *C07K 16/2878* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,576,184 A | 11/1996 | Better et al. |
| 2004/0031072 A1 | 2/2004 | La Rosa et al. |
| 2005/0108791 A1 | 5/2005 | Edgerton et al. |
| 2016/0244785 A1 | 8/2016 | Koepke et al. |
| 2019/0375847 A1* | 12/2019 | Cortez ............. A61K 39/39541 |
| 2020/0048363 A1* | 2/2020 | Harding ............ C07K 16/2875 |
| 2020/0071409 A1* | 3/2020 | Attinger .................... A61P 3/10 |
| 2020/0079861 A1* | 3/2020 | Wilson .................... A61P 37/04 |
| 2020/0181275 A1* | 6/2020 | Hopson ................. C07K 16/30 |

FOREIGN PATENT DOCUMENTS

| | | |
|---|---|---|
| WO | 199530004 | 11/1995 |
| WO | 199749800 | 12/1997 |
| WO | 2002088306 | 11/2002 |
| WO | 2005028511 | 3/2005 |
| WO | 2011023785 | 3/2011 |
| WO | 2012148003 | 11/2012 |
| WO | 2013038191 | 3/2013 |
| WO | 2015035190 | 3/2015 |
| WO | 2015094106 | 6/2015 |
| WO | 2016094837 | 6/2016 |

OTHER PUBLICATIONS

Croft, "Control of Immunity by the TNFR-Related Molecule OX40 (CD134)", Annu Rev Immunol., 28: 57-78, Mar. 1, 2010.
Linch et al., "OX40 agonists and combination immunotherapy: putting the pedal to the metal", Frontiers in Oncology, 5(34): 1-14, Feb. 16, 2015.
PCT Written Opinion of the International Search Authority, dated Dec. 26, 2018.

* cited by examiner

*Primary Examiner* — Phillip Gambel
(74) *Attorney, Agent, or Firm* — Craig A Crandall, APC; Craig A Crandall

(57) ABSTRACT

This application provides, inter alia, antibodies or antigen-binding fragments thereof, targeting OX40 expressed on injured tissues associated with multiple diseases. These OX40 antibodies, or antigen-binding fragments thereof, have a high affinity for OX40 and function as OX40 agonists or as OX40/OX40L antagonists. The antibodies and antigen-binding fragments are useful for treatment of human diseases, infections, and other conditions.

16 Claims, 2 Drawing Sheets
Specification includes a Sequence Listing.

ANTI-OX40 ANTIBODIES AND METHODS OF ACTIVATING OX40

RELATED PATENT APPLICATIONS

This application is a U.S. National Stage Application pursuant to 35 U.S.C. § 371 of PCT/US2018/044882, filed Aug. 1, 2018, which claims benefit of U.S. Provisional Application No. 62/539,946, filed on Aug. 1, 2017, each incorporated in its entirety by reference herein.

TECHNICAL FIELD

Tumor necrosis factor receptor/tumor necrosis factor (TNFR/TNF) superfamily members can control diverse aspects of immune function. It has been established that one of the most important and prominent interactions in this family is that between OX40 (CD134) and its partner OX40L (CD252). These molecules strongly regulate conventional CD4 and CD8 T cells, and more recent data has demonstrated their ability to modulate NKT cell and NK cell function as well as to mediate cross-talk with professional antigen-presenting cells and diverse cell types such as mast cells, smooth muscle cells, and endothelial cells (Croft, Michael. *Annu Rev Immunol.*, 28: 57-78, 2010). Additionally, OX40-OX40L interactions alter the differentiation and activity of regulatory T cells. Blocking OX40L has produced strong therapeutic effects in multiple animal models of autoimmune and inflammatory disease, and, in line with a prospective clinical future, reagents that stimulate OX40 signaling are showing promise as adjuvants for vaccination as well as for treatment of cancer (Id).

The ability of OX40 agonists to regulate immune responses, as well as the expression of OX40 on CD4 and CD8 lymphocytes from the tumors and tumor-draining lymph nodes in mice and humans led investigators to examine OX40 manipulation as a treatment for cancer patients (Vetto et al., Am J Surg, 174(3):258-65, 1997). Preclinical studies demonstrated that treatment of tumor-bearing hosts with OX40 agonists, including both OX40 mAb and OX40L-Fc fusion proteins, resulted in tumor regression in several preclinical models (Piconese et al., *J Exp Med*, 205(4):825-39, 2008). Recently, the use of OX40 monotherapy was tested in a Phase 1 trial in patients with solid tumors, with promising results (Curti et al, Cancer Res, 73(24):7189-98, 2013). Twelve out of 30 patients receiving an OX40 agonist had regression of at least 1 metastatic lesion with only 1 cycle of treatment. Unfortunately, the development of human anti-mouse antibodies to the drug precluded continued treatment. MedImmune has several Phase 1 clinical trials investigating OX40 agonists including NCT02318394, NCT02205333, and NCT02221960. GlaxoSmithKline has first time in human (FTIH), open-label, non-randomized, multicenter study designed to evaluate the safety, tolerability, pharmacokinetics (PK), pharmacodynamics, and preliminary clinical activity of GSK3174998 administered intravenously to subjects with selected advanced or recurrent solid tumors (NCT02528357). Indeed, the use of OX40 agonists in the clinic represents an exciting new chapter in cancer immunotherapy. Further studies and patient immune monitoring will provide further insight into the mechanisms by which OX40 agonists enhance an anti-tumor immune response.

DISCLOSURE OF THE INVENTION

In accordance with the present invention, there are provided isolated antibodies, and antigen-binding fragments thereof, that specifically bind OX40 receptor (also known as Tumor necrosis factor receptor superfamily, member 4 (TNFRSF4) and CD134). These OX40 antibodies, or antigen-binding fragments thereof, have a high affinity for OX40, function as OX40 agonists or OX40/OX40L antagonists, and are less immunogenic compared to their unmodified parent antibodies in a given species (e.g., a human), and can be used to treat human diseases (e.g., cancer), infections, and other disorders.

In various embodiments, the antibody or antigen-binding fragment is selected from a fully human antibody, a humanized antibody, a chimeric antibody, a monoclonal antibody, a polyclonal antibody, a recombinant antibody, a single chain antibody, a diabody, a triabody, a tetrabody, a Fab fragment, a Fab' fragment, a Fab$_2$ fragment, a F(ab)'$_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds. In various embodiments, the antibody is a chimeric antibody. In various embodiments, the antibody is a humanized antibody. In various embodiments, the antibody is a fully human antibody. In various embodiments, isolated antibodies, and antigen-binding fragments thereof, that have a high affinity for the human OX40 protein of SEQ ID NO: 1 are provided. In various embodiments, the antibody or antigen-binding fragment is an agonist of OX40. In various embodiments, the antibody or antigen-binding fragment is an OX40/OX40L antagonist.

In various embodiments, the antibody or antigen-binding fragment binds to OX40 protein with a dissociation constant ($K_D$) of at least about $1\times10^{-6}$ M, at least about $1\times10^{-7}$ M, at least about $1\times10^{-8}$ M, at least about $1\times10^{-9}$ M, at least about $1\times10^{10}$M, at least about $1\times10^{-11}$ M, or at least about $1\times10^{-12}$ M.

In one aspect, an isolated antibody or antigen-binding fragment thereof of the present invention binds to human OX40 and comprises either: (a) a light chain CDR3 sequence identical, substantially identical or substantially similar to a CDR3 sequence selected from SEQ ID NOs: 26-28; (b) a heavy chain CDR3 sequence identical, substantially identical or substantially similar to a CDR3 sequence selected from SEQ ID NOs: 13-17; or (c) the light chain CDR3 sequence of (a) and the heavy chain CDR3 sequence of (b).

In various embodiments, the isolated antibody or antigen-binding fragment further comprises an amino acid sequence selected from: (d) a light chain CDR1 sequence identical, substantially identical or substantially similar to a CDR1 sequence selected from SEQ ID NO: 18-21; (e) a light chain CDR2 sequence identical, substantially identical or substantially similar to a CDR2 sequence selected from SEQ ID NOs: 22-25; (f) a heavy chain CDR1 sequence identical, substantially identical or substantially similar to a CDR1 sequence selected from SEQ ID NO: 2-7; (g) a heavy chain CDR2 sequence identical, substantially identical or substantially similar to a CDR2 sequence selected from SEQ ID NOs: 8-12; (h) the light chain CDR1 sequence of (d) and the heavy chain CDR1 sequence of (f); or (i) the light chain CDR2 sequence of (e) and the heavy chain CDR2 sequence of (g).

In various embodiments, the isolated human monoclonal antibody or antigen-binding fragment thereof of the present invention binds to human OX40 and comprises: (a) a light chain CDR1 sequence identical, substantially identical or substantially similar to a CDR1 sequence selected from SEQ ID NO: 18-21; (b) a light chain CDR2 sequence identical, substantially identical or substantially similar to a CDR2 sequence selected from SEQ ID NOs: 22-25; (c) a light chain CDR3 sequence identical, substantially identical or substantially similar to a CDR3 sequence selected from SEQ ID NOs: 26-28; (d) a heavy chain CDR1 sequence identical, substantially identical or substantially similar to a CDR1 sequence selected from SEQ ID NOs: 2-7; (e) a heavy chain CDR2 sequence identical, substantially identical or substantially similar to a CDR2 sequence selected from SEQ ID NOs: 8-12; and (f) a heavy chain CDR3 sequence identical, substantially identical or substantially similar to a CDR3 sequence selected from SEQ ID NOs: 13-17.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 18; (b) a light chain CDR2 sequence identical, substantially identical or substantially similar to SEQ ID NO: 22; (c) a light chain CDR3 sequence identical, substantially identical or substantially similar to SEQ ID NO: 26; (d) a heavy chain CDR1 sequence identical, substantially identical or substantially similar to SEQ ID NO: 2; (e) a heavy chain CDR2 sequence identical, substantially identical or substantially similar to SEQ ID NO: 8; and (f) a heavy chain CDR3 sequence identical, substantially identical or substantially similar to SEQ ID NO: 13.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 18; (b) a light chain CDR2 sequence identical, substantially identical or substantially similar to SEQ ID NO: 22; (c) a light chain CDR3 sequence identical, substantially identical or substantially similar to SEQ ID NO: 26; (d) a heavy chain CDR1 sequence identical, substantially identical or substantially similar to SEQ ID NO: 3; (e) a heavy chain CDR2 sequence identical, substantially identical or substantially similar to SEQ ID NO: 9; and (f) a heavy chain CDR3 sequence identical, substantially identical or substantially similar to SEQ ID NO: 13.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 19; (b) a light chain CDR2 sequence identical, substantially identical or substantially similar to SEQ ID NO: 23; (c) a light chain CDR3 sequence identical, substantially identical or substantially similar to SEQ ID NO: 27; (d) a heavy chain CDR1 sequence identical, substantially identical or substantially similar to SEQ ID NO: 4; (e) a heavy chain CDR2 sequence identical, substantially identical or substantially similar to SEQ ID NO: 10; and (f) a heavy chain CDR3 sequence identical, substantially identical or substantially similar to SEQ ID NO: 14.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 20; (b) a light chain CDR2 sequence identical, substantially identical or substantially similar to SEQ ID NO: 24; (c) a light chain CDR3 sequence identical, substantially identical or substantially similar to SEQ ID NO: 28; (d) a heavy chain CDR1 sequence identical, substantially identical or substantially similar to SEQ ID NO: 5; (e) a heavy chain CDR2 sequence identical, substantially identical or substantially similar to SEQ ID NO: 11; and (f) a heavy chain CDR3 sequence identical, substantially identical or substantially similar to SEQ ID NO: 15.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 21; (b) a light chain CDR2 sequence identical, substantially identical or substantially similar to SEQ ID NO: 25; (c) a light chain CDR3 sequence identical, substantially identical or substantially similar to SEQ ID NO: 28; (d) a heavy chain CDR1 sequence identical, substantially identical or substantially similar to SEQ ID NO: 6; (e) a heavy chain CDR2 sequence identical, substantially identical or substantially similar to SEQ ID NO: 12; and (f) a heavy chain CDR3 sequence identical, substantially identical or substantially similar to SEQ ID NO: 16.

In various embodiments, the isolated human monoclonal antibody or antigen-binding fragment thereof of the present invention binds to human OX40 and comprises: (a) a light chain CDR1 sequence identical, substantially identical or substantially similar to SEQ ID NO: 20; (b) a light chain CDR2 sequence identical, substantially identical or substantially similar to SEQ ID NO: 24; (c) a light chain CDR3 sequence identical, substantially identical or substantially similar to SEQ ID NO: 28; (d) a heavy chain CDR1 sequence identical, substantially identical or substantially similar to SEQ ID NO: 7; (e) a heavy chain CDR2 sequence identical, substantially identical or substantially similar to SEQ ID NO: 11; and (f) a heavy chain CDR3 sequence identical, substantially identical or substantially similar to SEQ ID NO: 17.

In various embodiments, an isolated antibody or antigen-binding fragment thereof of the present invention binds to human OX40 and comprises either: (a) a heavy and/or light chain variable domain(s), the variable domain(s) having a set of three light chain CDR1, CDR2, and CDR3 identical, substantially identical or substantially similar to SEQ ID NOs: 18-21, 22-25, and 26-28, and/or a set of three heavy chain CDR1, CDR2, and CDR3 identical, substantially identical or substantially similar to SEQ ID NOs: 2-7, 8-12, and 13-17; and (b) a set of four variable region framework regions from a human immunoglobulin (IgG). In various embodiments, the antibody can optionally include a hinge region. In various embodiments, the antibody is a fully humanized antibody. In various embodiments, the antibody is a fully human antibody.

In various embodiments, the framework regions are chosen from human germline exon $X_H$, $J_H$, Vκ and Jκ sequences. For example, acceptor sequences for humanization of FR of a $V_H$ domain can be chosen from genuine $V_H$ exons $V_H$ 1-18 (Matsuda et al., Nature Genetics 3:88-94, 1993) or $V_H$1-2 (Shin et al., EMBO J. 10:3641-3645, 1991) and for the hinge region ($J_H$), exon $J_H$-6 (Mattila et al., Eur. J. Immunol. 25:2578-2582, 1995). In other examples, germline Vκ exon B3 (Cox et al., Eur. J. Immunol. 24:827-836, 1994) and Jκ exon JK-1 (Hieter et al., J. Biol. Chem. 257:1516-1522, 1982) can be chosen as acceptor sequences for $V_L$ domain humanization.

In various embodiments, the isolated antibody or antigen-binding fragment, when bound to human OX40: (a) binds to human OX40 with substantially the same or greater Kd as a reference antibody; (b) competes for binding to human OX40 with said reference antibody; or (c) is less immunogenic in a human subject than said reference antibody, wherein said reference antibody comprises the combination of heavy chain variable domain and light chain variable domain sequences set forth in SEQ ID NOs: 40 and 52.

In various embodiments, an isolated humanized antibody or antigen-binding fragment thereof of the present invention binds to human OX40 and comprises a heavy chain variable region having a sequence identical, substantially identical or substantially similar to the sequences set forth in SEQ ID NOs: 56-62, and a light chain variable region having the sequence identical, substantially identical or substantially similar to the sequences set forth in SEQ ID NOs: 63-69.

In various embodiments the antibody is a humanized antibody which comprises the heavy chain variable region having the amino acid sequence set forth in SEQ ID NO: 61 and the light chain variable region having the amino acid sequence set forth in SEQ ID NO: 67. In various embodiments the antibody is a humanized antibody which comprises the heavy chain variable region having the amino acid sequence set forth in SEQ ID NO: 61 and the light chain variable region having the amino acid sequence set forth in SEQ ID NO: 68. In various embodiments the antibody is a humanized antibody which comprises the heavy chain variable region having the amino acid sequence set forth in SEQ ID NO: 61 and the light chain variable region having the amino acid sequence set forth in SEQ ID NO: 69.

In various embodiments, an isolated humanized antibody or antigen-binding fragment thereof of the present invention binds to human OX40 and comprises a heavy chain having a sequence identical, substantially identical or substantially similar to the sequences set forth in SEQ ID NOs: 86-92, and a light chain having the sequence identical, substantially identical or substantially similar to the sequences set forth in SEQ ID NOs: 93-99.

In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 97. In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 98. In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 99.

In another aspect, the present invention relates to a pharmaceutical composition comprising an isolated antibody or antigen-binding fragment of the present invention in admixture with a pharmaceutically acceptable carrier. In various embodiments, the pharmaceutical composition comprises an isolated human antibody in admixture with a pharmaceutically acceptable carrier. In various embodiments, the pharmaceutical composition is formulated for administration via a route selected from the group consisting of subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or via infusions.

In another aspect, the present invention relates to methods for enhancing the immune response to cancerous cells in a subject, comprising administering to the subject a therapeutically effective amount (either as monotherapy or in a combination therapy regimen) of an isolated antibody or antigen-binding fragment of the present invention. In various embodiments, the present invention provides for a method of treating cancerous cells in a subject, comprising administering to said subject a therapeutically effective amount (either as monotherapy or in a combination therapy regimen) of an antibody or antigen-binding fragment thereof of the present invention. In various embodiments, the cancerous cell is selected from the group consisting of ovarian cancer, lung cancer, breast cancer, gastric cancer, prostate cancer, colon cancer, renal cell cancer, glioblastoma, and melanoma.

In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancerous cells are immunogenic tumors (e.g., those tumors for which vaccination using the tumor itself can lead to immunity to tumor challenge).

In another aspect, the present invention relates to combination therapies designed to treat a cancer in an subject, comprising administering to the subject a therapeutically effective amount of an isolated antibody or antigen-binding fragment of the present invention, and b) one or more additional therapies selected from the group consisting of immunotherapy, chemotherapy, small molecule kinase inhibitor targeted therapy, surgery, radiation therapy, and stem cell transplantation, wherein the combination therapy provides increased cell killing of tumor cells, i.e., a synergy exists between the isolated antibody or antigen-binding fragment and the additional therapies when co-administered.

In various embodiments, the present invention relates to methods for stimulating an immune response to pathogens, toxins and self-antigens in a subject, comprising administering to the subject a therapeutically effective amount (either as monotherapy or in a combination therapy regimen) of an isolated antibody or antigen-binding fragment of the present invention. In various embodiments, the subject has an infectious disease that is resistant to, or ineffectively treated by, treatment using conventional vaccines.

In another aspect, an isolated immunoconjugate or fusion protein comprising an antibody or antigen-binding fragment conjugated to, linked to (or otherwise stably associated with) an effector molecule is provided. In various embodiments, the effector molecule is an immunotoxin, cytokine, chemokine, therapeutic agent, or chemotherapeutic agent.

In another aspect, the antibodies or antigen-binding fragments disclosed herein may be covalently linked to (or otherwise stably associated with) an additional functional moiety, such as a label or a moiety that confers desirable pharmacokinetic properties. In various embodiments, the label is selected from the group consisting of: a fluorescent label, a radioactive label, and a label having a distinctive nuclear magnetic resonance signature.

In another aspect, the present invention provides a method for detecting in vitro or in vivo the presence of human OX40 antigen in a sample, e.g., for diagnosing a human OX40-related disease.

In another aspect, provided is an isolated nucleic acid comprising the polynucleotide sequence that encodes either the heavy chain variable domain, the light chain variable domain, or both, of an antibody or antigen-binding fragment of the invention. In various embodiments, the polynucleotide comprises a heavy chain variable domain polynucleotide sequence of SEQ ID NOs: 70-76; a light chain variable domain polynucleotide sequence of SEQ ID NOs: 77-83, or both.

In another aspect, provided is an isolated nucleic acid comprising the polynucleotide sequence that encodes either the heavy chain, the light chain, or both, of an antibody or antigen-binding fragment of the invention. In various embodiments, the polynucleotide comprises a heavy chain polynucleotide sequence of SEQ ID NOs: 100-106; a light chain polynucleotide sequence of SEQ ID NOs: 107-113, or both.

Also provided are vectors comprising the nucleic acid of the present invention. In one embodiment the vector is an expression vector. Also provided is an isolated cell comprising the nucleic acid of the invention. In one embodiment, the cell is a host cell comprising the expression vector of the invention. In another embodiment, the cell is a hybridoma, wherein the chromosome of the cell comprises nucleic acid of the invention. Further provided is a method of making the antibody or antigen-binding fragment of the present invention comprising culturing or incubating the cell under conditions that allow the cell to express the antigen binding protein of the invention.

MODE(S) FOR CARRYING OUT THE INVENTION

Figure 1A:
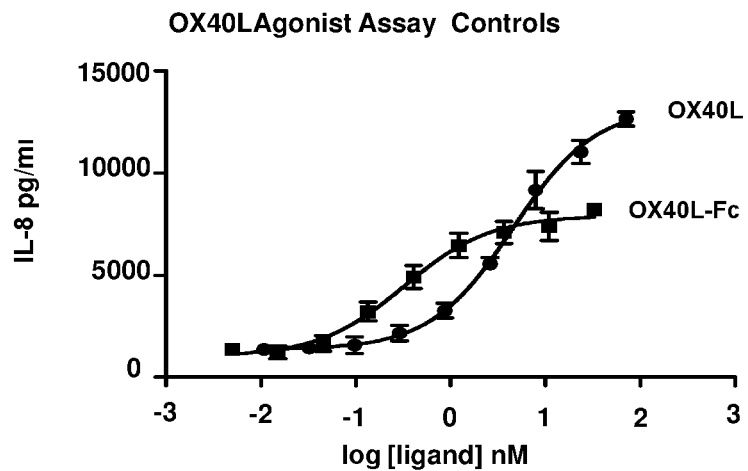
FIG. 1A is a line plot depicting the potency of OX40L agonist assay controls OX40L-Fc (—●—) and OX40L (—■—) in an in vitro cell-based OX40 functional assay. The potency of samples was measured by the concentration of interleukin 8 (IL-8) secreted by HT1080 OX40 stable cell lines.

The present invention relates to antigen binding proteins such as antibodies, or antigen-binding fragments thereof that specifically bind to human OX40. In one aspect, there are provided isolated antibodies, and antigen-binding fragments thereof, that specifically bind OX40, have a high affinity for OX40, function as OX40 agonists or OX40/OX40L antagonists, are less immunogenic compared to their unmodified parent antibodies in a given species (e.g., a human), and can be used to treat human diseases (e.g., cancer), infections, and other disorders mediated by OX40. Also provided are nucleic acid molecules, and derivatives and fragments thereof, comprising a sequence of polynucleotides that encode all or a portion of a polypeptide that binds to OX40, such as a nucleic acid encoding all or part of an OX40 antibody, antibody fragment, or antibody derivative. Also provided are vectors and plasmids comprising such nucleic acids, and cells or cell lines comprising such nucleic acids and/or vectors and plasmids. Also provided are methods of making, identifying, or isolating antigen binding proteins that bind to human OX40, such as OX40 antibodies, methods of determining whether an antigen binding protein binds to OX40, methods of making compositions, such as pharmaceutical compositions, comprising an antigen binding protein that binds to human OX40, and methods for administering an antibody, or antigen-binding fragment thereof that binds OX40 to a subject, for example, methods for treating a condition mediated by OX40.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Green and Sambrook, Molecular Cloning: A Laboratory Manual, 4th ed., Cold Spring Harbor Laboratory Press, Cold Spring Harbor, N.Y. (2012), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of subjects.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 80 to 119, or by the actual residue at that site such as Ser80 to Ser119. A particular polypeptide or polynucleotide sequence also can be described based upon how it differs from a reference sequence. Polynucleotide and polypeptide sequences of particular light and heavy chain variable domains are designated L1 ("light chain variable domain 1") and H1 ("heavy chain variable domain 1"). Antibodies comprising a light chain and heavy chain are indicated by combining the name of the light chain and the name of the heavy chain variable domains. For example, "L4H4," indicates, for example, an antibody comprising the light chain variable domain of L4 and the heavy chain variable domain of H4.

The term "antibody" is used herein to refer to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition.

In a full-length antibody, each heavy chain is comprised of a heavy chain variable region (abbreviated herein as HCVR or VH) and a heavy chain constant region. The heavy chain constant region is comprised of three domains, CH1, CH2 and CH3 (and in some instances, CH4). Each light chain is comprised of a light chain variable region (abbreviated herein as LCVR or VL) and a light chain constant region. The light chain constant region is comprised of one domain, $C_L$. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The CDRs are primarily responsible for binding to an epitope of an antigen. The CDRs of each chain are typically referred to as CDR1, CDR2, CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The Kabat definition is a standard for numbering the residues in an antibody and is typically used to identify CDR regions. The Kabat database is now maintained online and CDR sequences can be determined, for example, see IMGT/V-QUEST programme version: 3.2.18., Mar. 29, 2011, available on the internet and Brochet, X. et al., Nucl. Acids Res. 36, W503-508, 2008). The Chothia definition is similar to the Kabat definition, but the Chothia definition takes into account positions of certain structural loop regions. See, e.g., Chothia et al., J. Mol. Biol., 196: 901-17, 1986; Chothia et al., Nature, 342: 877-83, 1989. The AbM definition uses an integrated suite of computer programs produced by Oxford Molecular Group that model antibody structure. See, e.g., Martin et al., Proc. Natl. Acad. Sci. USA, 86:9268-9272, 1989; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198, 1999. The contact definition is based on an analysis of the available complex crystal structures. See, e.g., MacCallum et al., J. Mol. Biol., 5:732-45, 1996.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (sdFv), intrabodies, and epitope-binding fragments or antigen binding fragments of any of the above.

Papain digestion of antibodies produces two identical antigen-binding fragments, called "Fab" fragments, each with a single antigen-binding site. A "Fab fragment" comprises one light chain and the CH1 and variable regions of one heavy chain. The heavy chain of a Fab molecule cannot form a disulfide bond with another heavy chain molecule. A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule.

Pepsin treatment of an antibody yields an F(ab')$_2$ fragment that has two antigen-combining sites and is still capable of cross-linking antigen. A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649, U.S. Pat. Nos. 4,946,778 and 5,260,203, the disclosures of which are incorporated by reference.

The terms "an antigen-binding fragment" and "antigen-binding protein" as used herein means any protein that binds a specified target antigen. "Antigen-binding fragment" includes but is not limited to antibodies and binding parts thereof, such as immunologically functional fragments. An exemplary antigen-binding fragment of an antibody is the heavy chain and/or light chain CDR(s), or the heavy and/or light chain variable region.

The term "immunologically functional fragment" (or simply "fragment") of an antibody or immunoglobulin chain (heavy or light chain) antigen binding protein, as used herein, is a species of antigen binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding proteins, including intact antibodies, for binding to a given epitope. In some embodiments, the fragments are neutralizing fragments. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, a diabody, Fab', F(ab')$_2$, Fv, domain antibodies and single-chain antibodies, and can be derived from any mammalian source, including but not limited to human, mouse, rat, camelid or rabbit. It is further contemplated that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

Diabodies are bivalent antibodies comprising two polypeptide chains, wherein each polypeptide chain comprises VH and VL regions joined by a linker that is too short to allow for pairing between two regions on the same chain, thus allowing each region to pair with a complementary region on another polypeptide chain (see, e.g., Holliger et al., Proc. Natl. Acad. Sci. USA, 90:6444-48, 1993; and Poljak et al., Structure, 2:1121-23, 1994). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci. USA, 78:5807, 1981; by "polydoma" techniques (see, e.g., U.S. Pat. No. 4,474,893); or by recombinant DNA techniques. In various embodiments bispecific antibodies of the present disclosure can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions.

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In various embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. All such recombinant means are well known to those of ordinary skill in the art.

The term "epitope" as used herein includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present disclosure. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

An antigen binding protein, including an antibody, "specifically binds" to an antigen if it binds to the antigen with a high binding affinity as determined by a dissociation constant ($K_D$, or corresponding Kb, as defined below) value of at least $1\times10^{-6}$ M, or at least $1\times10^{-7}$ M, or at least $1\times10^{-8}$ M, or at least $1\times10^{-9}$ M, or at least $1\times10^{-10}$ M, or at least $1\times10^{-11}$ M. An antigen binding protein that specifically binds to the human antigen of interest may be able to bind to the same antigen of interest from other species as well, with the same or different affinities. The term "$K_D$" as used herein refers to the equilibrium dissociation constant of a particular antibody-antigen interaction.

The term "surface plasmon resonance" as used herein refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin., 51:19-26, 1993; Jonsson U. et al., Biotechniques, 11:620-627, 1991; Jonsson B. et al., J. Mol. Recognit., 8:125-131, 1995; and Johnsson B. et al., Anal. Biochem, 198:268-277, 1991.

The term "immunogenicity" as used herein refers to the ability of an antibody or antigen binding fragment to elicit an immune response (humoral or cellular) when administered to a recipient and includes, for example, the human anti-mouse antibody (HAMA) response. A HAMA response is initiated when T-cells from a subject make an immune response to the administered antibody. The T-cells then recruit B-cells to generate specific "anti-antibody" antibodies.

The term "immune cell" as used herein means any cell of hematopoietic lineage involved in regulating an immune response against an antigen (e.g., an autoantigen). In various embodiments, an immune cell is, e.g., a T cell, a B cell, a dendritic cell, a monocyte, a natural killer cell, a macrophage, Langerhan's cells, or Kuffer cells.

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "recombinant polypeptide", as used herein, is intended to include all polypeptides, including fusion molecules that are prepared, expressed, created, derived from, or isolated by recombinant means, such as polypeptides expressed using a recombinant expression vector transfected into a host cell.

Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:
  Alanine (A), Serine (S), and Threonine (T)
  Aspartic acid (D) and Glutamic acid (E)
  Asparagine (N) and Glutamine (Q)
  Arginine (R) and Lysine (K)

Isoleucine (I), Leucine (L), Methionine (M), and Valine (V)

Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within +0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within 2 is included, in various embodiments, those that are within ±1 are included, and in various embodiments, those within ±0.5 are included. Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |

TABLE 1-continued

| Original Residues | Exemplary Substitutions | Preferred Substitutions |
|---|---|---|
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 25:3389-3402, 1997. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See Id.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent, and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

As used herein, the term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as OX40, PD-1, PD-L1, OX-40, CD137, GITR, LAG3, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF, IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

The term "immunoconjugate" or "fusion protein" as used herein refers to a molecule comprising an antibody or antigen-binding fragment thereof conjugated (or linked) directly or indirectly to an effector molecule. The effector molecule can be a detectable label, an immunotoxin, cytokine, chemokine, therapeutic agent, or chemotherapeutic agent. The antibody or antigen-binding fragment thereof may be conjugated to an effector molecule via a peptide linker. An immunoconjugate and/or fusion protein retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate may also be referred to as an antibody drug conjugate (ADC). Because immunoconjugates and/or fusion proteins are originally prepared from two molecules with separate functionalities, such as an antibody and an effector molecule, they are also sometimes referred to as "chimeric molecules."

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. As used herein, "treatment" is an approach for obtaining beneficial or desired clinical results. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, and remission (whether partial or total). Also encompassed by "treatment" is a reduction of pathological consequence of a proliferative disease. The methods of the invention contemplate any one or more of these aspects of treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

Resistant or refractory cancer" refers to tumor cells or cancer that do not respond to previous anti-cancer therapy including, e.g., chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, surgery alone, or combinations thereof. For ease of description and not limitation, it will be understood that the refractory tumor cells are interchangeable with resistant tumor.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

OX40 Antigen

OX40 (also known as ACT35, CD134, TNFRSF4) was first discovered in 1987 with an antibody (termed MRC OX40) that bound to activated rat CD4 T cells (Paterson et al., Mol Immunol., 24:1281-90, 1987). OX40 is an approximately 50-kD glycoprotein and has been cloned in the rat, mouse, and human (Latza et al., Eur J Immunol, 24:677-83, 1994). It is a type 1 transmembrane protein of 249 amino acids, with a 49 amino acid cytoplasmic tail and a 186 amino acid extracellular region. It was initially found to have homology to NGFR (nerve growth factor receptor) and CD40 and was then classified as a member of the TNFR (tumor necrosis factor receptor) superfamily, as more proteins with sequence and structural similarity to TNFR were discovered. The gene for OX40 is clustered on human chromosome 1 (mouse chromosome 4) with several other TNFR family molecules, TNFR2, 4-1BB, HVEM, CD30, GITR, and DR3. OX40 has three complete and one truncated cysteine-rich domains that are characteristic of the TNFR superfamily.

Human OX40 as used herein may comprise the amino acid sequence set forth in NCBI Reference Sequence: NP_003318 (SEQ ID NO: 1):

(SEQ ID NO: 1)
LHCVGDTYPSNDRCCHECRPGNGMVSRCSRSQNTVCRPCGPGFYNDVVSS

KPCKPCTWCNLRSGSERKQLCTATQDTVCRCRAGTQPLDSYKPGVDCAPC

PPGHFSPGDNQACKPWTNCTLAGKHTLQPASNSSDAICEDRDPPATQPQE

TQGPPARPITVQPTEAWPRTSQGPSTRPVEVPGGRAVAAILGLGLVLGLL

GPLAILLALYLLRRDQRLPPDAHKPPGGGSFRTPIQEEQADAHSTLAKI

In various embodiments, a OX40 polypeptide comprises an amino acid sequence that shares an observed homology of, e.g., at least 70%, at least 75%, at least 80%, at least 85%, at least 90%, at least 95%, at least 96%, at least 97%, at least 98%, or at least 99% with the human OX40 sequence of SEQ ID NO: 1. In some embodiments, the GDF-15 variant has at least 70%, at least 75%, at least 80%, at least 85%, at least 90%, at least 95%, at least 96%, at least 97%, at least 98%, at least 99%, at least 1×, at least 1.5×, at least 2×, at least 2.5×, or at least 3× activity of the human OX40 of SEQ ID NO: 1. Polypeptide variants of OX40 may be described herein by reference to the addition, deletion, or substitution of amino acid residue present at a given position in the 223 amino acid sequence of SEQ ID NO: 1. Thus, for example, the term "P21W" indicates that the "P" (proline, in standard single letter code) residue at position 21 in SEQ ID NO: 1 has been substituted with a "W" (tryptophan, in standard single letter code).

Antibodies

Methods of generating novel antibodies that bind to human OX40 polypeptide are known to those skilled in the art. For example, a method for generating a monoclonal antibody that binds specifically to an OX40 polypeptide may comprise administering to a mouse an amount of an immunogenic composition comprising the OX40 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the OX40 polypeptide. Once obtained, a hybridoma can be propagated in a cell culture, optionally in culture conditions where the hybridoma-derived cells produce the monoclonal antibody that binds specifically to OX40 polypeptide. The monoclonal antibody may be purified from the cell culture. A variety of different techniques are then available for testing antibody:antigen interactions to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555, 1993; Jakobovits et al., Nature, 362:255-258, 1993; Lonberg et al., U.S. Pat. No. 5,545,806; Surani et al., U.S. Pat. No. 5,545,807.

Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science, 240:1041-1043, 1988; Liu et al., PNAS USA, 84:3439-3443, 1987; Liu et al., J. Immunol. 139:3521-3526, 1987; Sun et al., PNAS USA, 84:214-218, 1987; Nishimura et al., Canc. Res. 47:999-1005, 1987; Wood et al., Nature 314:446-449, 1985; and Shaw et al., J. Natl Cancer Inst., 80:1553-1559, 1988).

Methods for humanizing antibodies have been described in the art. In practice, humanized antibodies are typically human antibodies in which some hypervariable region residues and possibly some framework region residues are substituted by residues from analogous sites in rodent antibodies. Accordingly, such "humanized" antibodies are chimeric antibodies wherein substantially less than an intact human variable region has been substituted by the corresponding sequence from a nonhuman species. To a degree, this can be accomplished in connection with techniques of humanization and display techniques using appropriate libraries. It will be appreciated that murine antibodies or antibodies from other species can be humanized or primatized using techniques well known in the art (see e.g., Winter et al., Immunol Today, 14:43-46, 1993; and Wright et al., Crit. Reviews in Immunol., 12125-168, 1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., P.N.A.S. 84:3439, 1987; J. Immunol. 139:3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions to genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. In various embodiments, the isotype is selected from the group consisting of IgG1, IgG2, IgG3 and IgG4. Either of the human light chain constant regions, kappa or lambda, may be used. The chimeric, humanized antibody is then expressed by conventional methods.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen-binding as described by Riechmann et al, 1988. Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

The choice of human variable regions, both light and heavy, to be used in making the desired humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296, 1993; Chothia et al., J. Mol. Biol., 196:901, 1987). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. USA, 89:4285, 1992; Presta et al., J. Immunol., 151:2623, 1993).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an OX40 antibody or antigen-binding fragment thereof comprises the steps of synthesizing a library of human antibodies on phage, screening the library with OX40 or an antibody-binding portion thereof, isolating phage that bind OX40, and obtaining the antibody from the phage. By way of another example, one method for preparing the library of antibodies for use in phage display techniques comprises the steps of immunizing a non-human animal comprising human immunoglobulin loci with OX40 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant OX40 antibodies of the invention may be obtained in this way.

Recombinant human OX40 antibodies of the invention can also be isolated by screening a recombinant combinatorial antibody library. Preferably the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85, 1992; Huse et al., Science 246: 1275-1281, 1989; McCafferty et al., Nature 348:552-554, 1990; Griffiths et al., EMBO J. 12:725-734, 1993; Hawkins et al., J. Mol. Biol. 226:889-896, 1992; Clackson et al., Nature 352:624-628, 1991; Gram et al., Proc. Natl. Acad. Sci. USA 89:3576-3580, 1992; Garrad et al., Bio/Technology 9:1373-1377, 1991; Hoogenboom et al., Nuc. Acid Res. 19:4133-4137, 1991; and Barbas et al., Proc. Natl. Acad. Sci. USA 88:7978-7982, 1991, each incorporated herein by reference for purposes of teaching preparation and screening of phase display libraries.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics 7:13-21, 1994; and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse™ mice further contain approximately all of the human lambda light chain locus. See Mendez et al., Nature Genetics 15:146-156, 1997, Green and Jakobovits, J. Exp. Med. 188:483-495 (1998), and WO 98/24893 (each incorporated by reference in its entirety for purposes of teaching the preparation of fully human antibodies). In another aspect, the present invention provides a method for making OX40 antibodies from non-human, non-mouse animals by immunizing non-human transgenic animals that comprise human immunoglobulin loci with a OX40 antigen. One can produce such animals using the methods described in the above-cited documents.

Characterization of Antibody Binding to Antigen

Antibodies of the present invention can be tested for binding to OX40 by, for example, standard ELISA. As an example, microtiter plates are coated with purified OX40 in PBS, and then blocked with 5% bovine serum albumin in PBS. Dilutions of antibody (e.g., dilutions of plasma from OX40-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions. An ELISA assay can also be used to screen for hybridomas that show positive reactivity with OX40 immunogen. Hybridomas that bind with high avidity to OX40 are subcloned and further characterized. One clone from each hybridoma, which retains the reactivity of the parent cells (by ELISA), can be chosen for making a 5-10 vial cell bank stored at −140° C., and for antibody purification.

To determine if the selected OX40 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using OX40 coated-ELISA plates as described above. Biotinylated mAb binding can be detected with a strep-avidin-alkaline phosphatase probe. To determine the isotype of purified antibodies, isotype ELISAs can be performed using reagents specific for antibodies of a particular isotype. For example, to determine the isotype of a human monoclonal antibody, wells of microtiter plates can be coated with 1 .mu.g/ml of anti-human immunoglobulin overnight at 4.degree. C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

OX40 human IgGs can be further tested for reactivity with OX40 antigen by Western blotting. Briefly, OX40 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Identification of OX40 Antibodies

The present invention provides monoclonal antibodies, and antigen-binding fragments thereof, that specifically bind to OX40 antigen.

Further included in the present invention are antibodies that bind to the same epitope as the OX40 antibodies of the present invention. To determine if an antibody can compete for binding to the same epitope as the epitope bound by the OX40 antibodies of the present invention, a cross-blocking assay, e.g., a competitive ELISA assay, can be performed. In an exemplary competitive ELISA assay, OX40 coated on the wells of a microtiter plate is pre-incubated with or without candidate competing antibody and then the biotin-labeled OX40 antibody of the invention is added. The amount of labeled OX40 antibody bound to the OX40 antigen in the wells is measured using avidin-peroxidase conjugate and appropriate substrate. The antibody can be labeled with a radioactive or fluorescent label or some other detectable and measurable label. The amount of labeled OX40 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an OX40 antibody of the invention if the candidate antibody can block binding of the OX40 antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

The amino acid sequences of the heavy chain CDRs and the light chain CDRs of various antigen binding proteins (antibodies) A1-A6 are shown below in Table 2. Antibodies A1-A6 corresponds to heavy chain variable regions H1-H6 below, and light chain variable regions L1-L6 below.

TABLE 2

| Ab | CDR1 | CDR2 | CDR3 |
|---|---|---|---|
| Heavy Chain CDRs | | | |
| A1 | DYAIH (SEQ ID NO: 2) | VINTYYGDAAYNQKFQG (SEQ ID NO: 8) | LDDFVY (SEQ ID NO: 13) |
| A2 | DYAMH (SEQ ID NO: 3) | VISTYYGDAAYNQKFKD (SEQ ID NO: 9) | LDDFVY (SEQ ID NO: 13) |
| A3 | SYGVH (SEQ ID NO: 4) | VIWAGGSTDYNSALMS (SEQ ID NO: 10) | EEVWD (SEQ ID NO: 14) |
| A4 | SYIMH (SEQ ID NO: 5) | YINPYNDGTKYNEKFKG (SEQ ID NO: 11) | YYGSSYTMDY (SEQ ID NO: 15) |
| A5 | ENYMN (SEQ ID NO: 6) | DINRNNGGTRYNQKFKG (SEQ ID NO: 12) | TVVGYFDV (SEQ ID NO: 16) |
| A6 | SYVMH (SEQ ID NO: 7) | YINPYNDGTKYNEKFKG (SEQ ID NO: 11) | YYGSNYAMDY (SEQ ID NO: 17) |
| Light Chain CDRs | | | |
| A1 | KSSQSLLDSDGKTYLN (SEQ ID NO: 18) | LVSKLDS (SEQ ID NO: 22) | WQGTHFPRT (SEQ ID NO: 26) |
| A2 | KSSQSLLDSDGKTYLN (SEQ ID NO: 18) | LVSKLDS (SEQ ID NO: 22) | WQGTHFPRT (SEQ ID NO: 26) |
| A3 | RASQDISNYLN (SEQ ID NO: 19) | YTSRLQS (SEQ ID NO: 23) | QQGNTLPLT (SEQ ID NO: 27) |
| A4 | RASQDIRNYLN (SEQ ID NO: 20) | YTSRLHS (SEQ ID NO: 24) | QQGNTLPWT (SEQ ID NO: 28) |
| A5 | RSSQDISNYLN (SEQ ID NO: 21) | YTSRLKS (SEQ ID NO: 25) | QQGNTLPWT (SEQ ID NO: 28) |
| A6 | RASQDIRNYLN (SEQ ID NO: 20) | YTSRLHS (SEQ ID NO: 24) | QQGNTLPWT (SEQ ID NO: 28) |

In various embodiments of the present invention, the antibody or antigen-binding fragment is a murine antibody A1 (5A8G11B11) comprising the heavy chain variable region sequence of H1 (SEQ ID NO: 30):

(SEQ ID NO: 30)
MGWSCIIFFLVATATGVHSQVQLQQSGAELVRPGVSVKISCKGSDYTFTD

YAIHWVKQSPAKSLEWIGVINTYYGDAAYNQKFQGKATMTVDKSSSAAYM

ELARLTSEDSAIYYCARLDDFVYWGQGTLVTVSA and the light chain variable region sequence of L1 (SEQ ID NO: 42):

(SEQ ID NO: 42)
MMSPAQFLFLLVLWIRETNGDVVMTQTPLTLSVTIGQPASISCKSSQSLL

DSDGKTYLNWLLQRPGQSPKRLIYLVSKLDSGVPDRFTGSGSGTDFTLKI

SRVEAEDLGVYYCWQGTHFPRTFGGGTKLEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 30, or its corresponding polynucleotide sequence SEQ ID NO: 29:

(SEQ ID NO: 29)
atgggttggagctgtatcatcttctttctggtagcaacagctacaggtgt gcactcccaggtccagctgcaacagtctggggctgagctggtgaggcctg gggtctcagtgaagatttcctgcaagggttctgactacacattcactgat tatgctatacactgggtgaagcagagtcctgcaaagagtctagagtggat tggagttattaatacttactatggtgatgctgcctacaaccagaagttcc agggcaaggccacaatgactgtagacaaatcctccagcgcagcctatatg gaacttgccagactgacatctgaggattctgccatctattactgtgcaag attagacgattttgtttactggggccaagggactctggtcactgtctctg ca and wherein the light chain comprises alight chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 42, or its corresponding polynucleotide sequence SEQ ID NO: 41:

(SEQ ID NO: 41)
atgatgagtcctgcccagttcctgtttctgttagtgctctggattcggga aaccaacggtgatgttgtgatgacccagactccactcactttgtcggtta ccattggtcaaccggcctccatctcttgcaagtcaagtcagagcctctta gatagtgatggaaagacatatttg aattggttgttacagaggccaggcc agtctccaaagcgcctaatctatctggtgtctaaactggactctggagtc cctgacaggttcactggcagtggatcagggacagatttcacactgaaaat cagcagagtggaggctgaggatttgggagtttattattgctggcaaggta cacattttcctcggacgttcggtggaggcaccaagctggaaatcaaa In various embodiments of the present invention, the antibody or antigen-binding fragment is a murine antibody A2 (4B12C9D9) comprising the heavy chain variable region sequence of H2 (SEQ ID NO: 32):

(SEQ ID NO: 32)
MGWSCIIFFLVATATGVHSQVQLQQSGAELVRPGVSVKIYCKGSGYTFTD

YAMHWVKQSHAKSLEWIGVISTYYGDAAYNQKFKDKATMTVDKSSSTAYM

ELARLTSEDSAIYYCARLDDFVYWGQGTLVTVSA and the light chain variable region sequence of L2 (SEQ ID NO: 44):

(SEQ ID NO: 44)
MMSPAQFLFLLVLWIREINGDVVMTQTPLTLSVTIGQPASISCKSSQSLL

DSDGKTYLNWLLQRPGQSPKRLIYLVSKLDSGVPDRFTGSGSGTDFTLKI

SRVEAEDLGVYYCWQGTHFPRTFGGGTKLEIK

In certain alternative embodiments, the antibody is an antibody comprising a heavy chain and alight chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 32, or its corresponding polynucleotide sequence SEQ ID NO: 31:

(SEQ ID NO: 31)
atgggttggagctgtatcatcttctttctggtagcaacagctacaggtgtg cactcccaggtccagctgcagcagtctggggctgagctggtgaggcctggg gtctcagtgaagatttactgcaagggttctggctacacattcactgattac gctatgcactgggtgaagcagagtcatgcaaagagtctagagtggattgga gttattagtacttactatggtgatgctgcttacaaccagaaattcaaggac aaggccacaatgactgtagacaaatcctccagcacagcctatatggaactt gccagactgacatctgaggattctgccatctattactgtgcaagattagac gattttgtttactggggccaagggactctggtcactgtctctgca and wherein the light chain comprises alight chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 44, or its corresponding polynucleotide sequence SEQ ID NO: 43:

(SEQ ID NO: 43)
atgatgagtcctgcccagttcctgtttctgttagtgctctggattcgggaa atcaacggtgatgttgtgatgacccagactccactcactttgtcggttacc attggacaaccagcctccatctcttgcaagtcaagtcagagcctcttagat agtgatggaaagacatatttgaattggttgttacagaggccaggccagtct ccaaagcgcctaatctatctggtgtctaaactggactctggagtccctgac aggttcactggcagtggatcagggacagatttcacactgaaaatcagcaga gtggaggctgaggatttgggagtttattattgctggcaaggtacacatttt cctcggacgttcggtggaggcaccaagctggaaatcaaa In various embodiments of the present invention, the antibody or antigen-binding fragment is a murine antibody A3 (14F2C2D7) comprising the heavy chain variable region sequence of H3 (SEQ ID NO: 34):

(SEQ ID NO: 34)
MAVLVLFLCLVAFPSCVLSQVQLKESGPGLVAPSQSLSITCTVSGFSLSSY

GVHWVRQPPGKGLEWLGVIWAGGSTDYNSALMSRLSISKDNSKSQVVLKMN

SLQTDDTAMYYCAREEVWDWGQGTLVTVSA and the light chain variable region sequence of L3 (SEQ ID NO: 46):

(SEQ ID NO: 46)
MMSSAQFLGLLLLCFQVLGIRCDIQMTQTTSSLSASLGDRVTISCRASQDI

SNYLNWYQQKPDGTVKLLIYYTSRLQSGVPSRFSGSGSGTDYSLTISNLEQ

EDIATYFCQQGNTLPLTFGAGTKLELK

In certain alternative embodiments, the antibody is an antibody comprising a heavy chain and alight chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 34, or its corresponding polynucleotide sequence SEQ ID NO: 33:

(SEQ ID NO: 33)
atggctgtcctggtgctgttcctctgcctggttgcatttccaagctgtgtc ctgtcccaggtgcagctgaaggagtcaggacctggcctggtggcgccctca cagagcctgtccatcacctgcactgtctctgggttttcattaagcagctat ggtgtacactgggttcgccagcctccaggaaagggtctggaatggctggga gtaatatggctggtggaagcacagattataattcggctctcatgtccaga ctgagcatcagcaaagacaactccaagagccaagttgtcttaaaaatgaac agcctgcaaactgatgacacagccatgtactactgtgccagagaagaggtc tgggactggggccaagggactctggtcactgtctctgca and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 46, or its corresponding polynucleotide sequence SEQ ID NO: 45:

(SEQ ID NO: 45)
atgatgtcctctgctcagttccttggtctcctgttgctctgttttcaagtc ctaggtatcagatgtgatatccagatgacacagactacatcctccctgtct gcctctctgggagacagagtcaccatcagttgcagggcaagtcaggacatt agcaattatttaaactggtatcagcagaaaccagatggaactgttaaactc ctgatctactacacatcaagattacagtcaggagtcccatcaaggttcagt ggcagtgggtctggaacagattattctctcaccattagcaacctggagcaa gaagatattgccacttacttttgccaacagggtaatacgcttcctctcacg ttcggtgctgggaccaagctggagctgaaa In various embodiments of the present invention, the antibody or antigen-binding fragment is a murine antibody A4 (13C2G10F10) comprising the heavy chain variable region sequence of H4 (SEQ ID NO: 36):

(SEQ ID NO: 36)
MEWSWIFLFLLSGTAGVHSEVQLQQSGPELVKPGASVKMSCKASGYTFTSY

IMHWVKQKPGQGLEWIGYINPYNDGTKYNEKFKGKATLTSDKSSSTAYMEL

SSLTSEDSAVYYCANYYGSSYTMDYWGQGTSVTVSS and the light chain variable region sequence of L4 (SEQ ID NO: 48):

(SEQ ID NO: 48)
MMSSAQFLGLLLLCFQGTRCDIQMTQTTSSLSASLGDRVTISCRASQDIRN

YLNWYQQKPDGSVKLLIYYTSRLHSGVPSRFSGSGSGTDYSLTISNLEQED

IATYFCQQGNTLPWTFGGGTKLEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 36, or its corresponding polynucleotide sequence SEQ ID NO: 35:

(SEQ ID NO: 35)
atggaatggagttggatatttctctttctcctgtcaggaactgcaggtgtc cactctgaggtccagctgcagcagtctggacctgagctggtaaagcctggg gcttcagtgaagatgtcctgcaaggcttctggatacacattcactagctat attatgcactgggtgaagcagaagcctgggcagggccttgagtggattgga tatattaatccttacaatgatggtactaagtacaatgaaaagttcaaaggc aaggccacactgacttcagacaaatcctccagcacagcctacatggagctc agcagcctgacctctgaggactctgcggtctattactgtgcaaattactac ggtagtagctatactatggactactggggtcaaggaacctcagtcaccgtc tcctca and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 48, or its corresponding polynucleotide sequence SEQ ID NO: 47:

(SEQ ID NO: 47)
atgatgtcctctgctcagttccttggtctcctgttgctctgttttcaaggt accagatgtgatatccagatgacacagactacatcctccctgtctgcctct ctgggagacagagtcaccatcagttgcagggcaagtcaggacattagaaat tatttaaactggtatcagcagaaaccagatggaagtgttaaactcctgatc tactacacatcaagattacactcaggagtcccatcaaggttcagtggcagt gggtctggaacagattattctctcaccattagcaacctggagcaagaagat attgccacttacttttgccaacagggtaatacgcttccgtggacgttcggt ggaggcaccaagctggaaatcaaa In various embodiments of the present invention, the antibody or antigen-binding fragment is a murine antibody A5 (40H11C2F5) comprising the heavy chain variable region sequence of H5 (SEQ ID NO: 38):

(SEQ ID NO: 38)
MGWSWIFLFLLSGTAGVLSEVQLQQSGPELVKPGASVKISCKASGYTFTEN

YMNWVKQSHGKSLEWIGDINRNNGGTRYNQKFKGKATLTVDKSSSTDYMEL

RSLTSEDSAVYYCGGTVVGYFDVWGTGTTVTVSS and the light chain variable region sequence of L5 (SEQ ID NO: 50):

(SEQ ID NO: 50)
MMSSAQFLGLLLLCFQGTRCDIQMTQIITSLSASLGDRVTISCRSSQDISN

YLNWYQQKPDGTVKLLIYYTSRLKSGVPSRFSGSGSGTDYSLTISNLEQED

IATYFCQQGNTLPWTFGGGTKLEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 38, or its corresponding polynucleotide sequence SEQ ID NO: 37:

(SEQ ID NO: 37)
atgggatggagctggatctttctctttctcctgtcaggaactgcaggtgtc ctctctgaggtccagctgcaacaatctggacctgagctggtgaagcctggg gcttcagtgaagatatcctgtaaggcttctggatacacgttcactgaaaac tacatgaactgggtgaagcagagccatggaaagagccttgagtggattgga gatattaatcgtaataatggtggtactagatacaaccagaagttcaaggac aaggccacattgactgtagacaagtcctccagcacagactacatggagctc cgcagcctgacatctgaggactctgcagtctattactgtgggggcacggta gtagggtacttcgatgtctggggcacagggaccacggtcaccgtctcctca and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 50, or its corresponding polynucleotide sequence SEQ ID NO: 49:

(SEQ ID NO: 49)
atgatgtcctctgctcagttccttggtctcctgttgctctgttttcaaggt accagatgtgatatccagatgacacagattataacctccctgtctgcctct ctgggagacagagtcaccatcagttgcaggtcaagtcaggacattagtaat tatttaaattggtatcagcagaaaccagatggaactgttaaactcctgatc tactacacatcaagattaaaatcaggagtcccatcaaggttcagtggcagt gggtctggaacagattattctctcaccattagcaacctggagcaagaagat attgccacttacttttgccaacagggtaatacgcttccgtggacgttcggt ggaggcaccaagctggaaatcaaa In various embodiments of the present invention, the antibody or antigen-binding fragment is a murine antibody A6 (2G2E2D8) comprising the heavy chain variable region sequence of H6 (SEQ ID NO: 40):

(SEQ ID NO: 40)
MEWSWIFLFLLSGTAGVHSEVQLQQSGPELVKPGASVKMSCKASGYTFTSY

VMHWVKQKPGQGLEWIGYINPYNDGTKYNEKFKGKATLTSDKSSTAYMEL

SSLTSEDSAVYYCANYYGSNYAMDYWGQGTSVTVSS and the light chain variable region sequence of L6 (SEQ ID NO: 52):

(SEQ ID NO: 52)
MMSSAQFLGLLLLCFQGTRCDIQMTQTTSSLSASLGDRVTISCRASQDIRN

YLNWYQQKPDGTVKLLIYYTSRLHSGVPSRFSGSGSGTDYSLTISNLEQED

IATYFCQQGNTLPWTFGGGTKLEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 40, or its corresponding polynucleotide sequence SEQ ID NO: 39:

(SEQ ID NO: 39)
atggaatggagttggatatttctctttctcctgtcaggaactgcaggtgtc cactctgaggtccagctgcagcagtctggacctgagctggtaaagcctggg gcttcagtgaagatgtcctgcaaggcttctggatacacattcactagctat gttatgcactgggtgaagcagaagcctgggcagggccttgagtggattgga tatattaatccttacaatgatggtactaagtacaatgagaagttcaaaggc aaggccacactgacttcagacaaatcctccagcacagcctacatggagctc agcagcctgacctctgaggactctgcggtctattactgtgcaaattactac ggtagtaactatgctatggactactggggtcaaggaacctcagtcaccgtc tcctca and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 52, or its corresponding polynucleotide sequence SEQ ID NO: 51:

(SEQ ID NO: 51)
atgatgtcctctgctcagttccttggtctcctgttgctctgttttcaaggt accagatgtgatatccagatgacacagactacatcctccctgtctgcctct ctgggagacagagtcaccatcagttgcagggcaagtcaggacattaggaat tatttaaactggtatcagcagaaaccagacggaactgttaaactcctgatc tactacacatcaagattacactcaggagtcccatcaaggttcagtggcagt gggtctggaacagattattctctcaccatcagcaacctggagcaagaagat attgccacttacttttgccaacagggtaatacgcttccgtggacgttcggt ggaggcaccaagctggaaatcaaa In various embodiments, the antibodies or antigen-binding fragments thereof comprise a heavy chain variable domain comprising a sequence of amino acids that differs from the sequence of a heavy chain variable domain having the amino acid sequence set forth in SEQ ID NOs: 30, 32, 34, 36, 38 or 40 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the heavy chain variable domain comprises a sequence of amino acids that is encoded by a polynucleotide that hybridizes under moderately stringent conditions to the complement of a polynucleotide that encodes a heavy chain variable domain having the sequence of SEQ ID NO: 29, 31, 33, 35, 37 or 39. In another embodiment, the heavy chain variable domain comprises a sequence of amino acids that is encoded by a polynucleotide that hybridizes under stringent conditions to the complement of a polynucleotide that encodes a heavy chain variable domain having the sequence of SEQ ID NO: 29, 31, 33, 35, 37 or 39.

In various embodiments, the antibodies or antigen-binding fragments thereof comprise a light chain variable domain comprising a sequence of amino acids that differs from the sequence of a light chain variable domain having the amino acid sequence set forth in SEQ ID NOs: 42, 44, 46, 48, 50 or 52 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the light chain variable domain comprises a sequence of amino acids that is encoded by a polynucleotide that hybridizes under moderately stringent conditions to the complement of a polynucleotide that encodes a light chain variable domain having the sequence of SEQ ID NO: 41, 43, 45, 47, 49 or 51. In another embodiment, the light chain variable domain comprises a sequence of amino acids that is encoded by a polynucleotide that hybridizes under stringent conditions to the complement of a polynucleotide that encodes a light chain variable domain having the sequence of SEQ ID NO: 41, 43, 45, 47, 49 or 51.

In various embodiments of the present disclosure, the antibody may be an OX40 antibody that has the same or higher antigen-binding affinity as that of the antibody comprising the heavy chain variable region sequence as set forth in any of SEQ ID NOS: 30, 32, 34, 36, 38 and 40. In various embodiments, the antibody may be an OX40 antibody which binds to the same epitope as the antibody comprising the heavy chain variable region sequence as set forth in any of SEQ ID NOs: 30, 32, 34, 36, 38 and 40. In various embodiments, the antibody is an OX40 antibody which competes with the antibody comprising the heavy chain variable region sequence as set forth in any of SEQ ID NOs: 30, 32, 34, 36, 38 and 40. In various embodiments, the antibody may be an OX40 antibody which comprises at least one (such as two or three) CDRs of the heavy chain variable region sequence as set forth in any of SEQ ID NOs: 30, 32, 34, 36, 38 and 40.

In various embodiments of the present disclosure the antibody may be an OX40 antibody that has the same or higher antigen-binding affinity as that of the antibody comprising the light chain variable region sequence as set forth in any of SEQ ID NOS: 42, 44, 46, 48, 50 and 52. In various embodiments, the antibody may be an OX40 antibody which binds to the same epitope as the antibody comprising the light chain variable region sequence as set forth in any of SEQ ID NOS: 42, 44, 46, 48, 50 and 52. In various embodiments, the antibody is an OX40 antibody which competes with the antibody comprising the light chain variable region sequence as set forth in any of SEQ ID NOS: 42, 44, 46, 48, 50 and 52. In various embodiments, the antibody may be an OX40 antibody which comprises at least one (such as two or three) CDRs of the light chain variable region sequence as set forth in any of SEQ ID NOS: 42, 44, 46, 48, 50 and 52.

In various embodiments, an isolated humanized antibody or antigen-binding fragment thereof of the present invention binds to human OX40 and comprises a heavy chain variable region having a sequence identical, substantially identical or substantially similar to the sequences set forth in SEQ ID NOs: 56-62, and a light chain variable region having the sequence identical, substantially identical or substantially similar to the sequences set forth in SEQ ID NOs: 63-69.

In various embodiments, an isolated antibody or antigen-binding fragment thereof of the present invention binds to human OX40 and comprises a heavy chain variable domain comprising a sequence of amino acids that differs from the sequence of a heavy chain variable domain having the amino acid sequence set forth in SEQ ID NOs: 56-62 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In various embodiments, the isolated antibodies or antigen-binding fragments thereof comprise a heavy chain variable domain comprising a sequence that has at least about 80%, at least about 85%, at least about 90%, 91%, 92%, 93%, 94%, 95%, 96%, 97%, 98%, or at least about 99% identity to the amino acid sequence as set forth in SEQ ID NOs: 56-62.

In various embodiments, an isolated antibody or antigen-binding fragment thereof of the present invention binds to human OX40 and comprises a light chain variable domain comprising a sequence of amino acids that differs from the sequence of a light chain variable domain having the amino acid sequence set forth in SEQ ID NOs: 63-69 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In various embodiments, the antibodies or antigen-binding fragments thereof comprise a light chain variable domain comprising a sequence that has at least about 80%, at least about 85%, at least about 90%, 91%, 92%, 93%, 94%, 95%, 96%, 97%, 98%, or at least about 99% identity to the amino acid sequence as set forth in SEQ ID NOs: 63-69.

In various embodiments the antibody is a humanized antibody which comprises the heavy chain variable region having the amino acid sequence set forth in SEQ ID NO: 61 and the light chain variable region having the amino acid sequence set forth in SEQ ID NO: 67. In various embodiments the antibody is a humanized antibody which comprises the heavy chain variable region having the amino acid sequence set forth in SEQ ID NO: 61 and the light chain variable region having the amino acid sequence set forth in SEQ ID NO: 68. In various embodiments the antibody is a humanized antibody which comprises the heavy chain variable region having the amino acid sequence set forth in SEQ ID NO: 61 and the light chain variable region having the amino acid sequence set forth in SEQ ID NO: 69.

In another embodiment, an isolated antibody or antigen-binding fragment thereof of the present invention binds to human OX40 and comprises a heavy chain variable domain which comprises a sequence of amino acids that is encoded by a polynucleotide that hybridizes under moderately stringent conditions to the complement of a polynucleotide that encodes a heavy chain variable domain having the sequence of SEQ ID NOs: 70-76. In another embodiment, the heavy chain variable domain comprises a sequence of amino acids that is encoded by a polynucleotide that hybridizes under stringent conditions to the complement of a polynucleotide that encodes a heavy chain variable domain having the sequence of SEQ ID NOs: 70-76. In another embodiment, an isolated antibody or antigen-binding fragment thereof of the present invention binds to human OX40 and comprises a light chain variable domain which comprises a sequence of amino acids that is encoded by a polynucleotide that hybridizes under moderately stringent conditions to the complement of a polynucleotide that encodes a light chain variable domain having the sequence of SEQ ID NOs: 77-83. In another embodiment, the light chain variable domain comprises a sequence of amino acids that is encoded by a polynucleotide that hybridizes under stringent conditions to the complement of a polynucleotide that encodes a light chain variable domain having the sequence of SEQ ID NOs: 77-83.

In various embodiments of the present invention, the antibody or antigen-binding fragment is a murine-human chimeric antibody derived from murine antibody A6 comprising the heavy chain sequence of SEQ ID NO: 84 and wherein amino acids 1-19 are a leader sequence:

(SEQ ID NO: 84)
MGWSWILLFLLSVTAGVHSEVQLQQSGPELVKPGASVKMSCKASGYTFTSY

VMHWVKQKPGQGLEWIGYINPYNDGTKYNEKFKGKATLTSDKSSSTAYMEL

SSLTSEDSAVYYCANYYGSNYAMDYWGQGTSVTVSSASTKGPSVFPLAPSS

KSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQP

ENNYKTIPPVLDSDGSFFLYSKLTVDKSRWQQGNVFSCSVMHEALHNHYTQ

KSLSLSPGK and the light chain sequence of SEQ ID NO: 85 and wherein amino acids 1-19 are a leader sequence (SEQ ID NO: 85)
MGWSWILLFLLSVTAGVHSDIQMTQTTSSLSASLGDRVTISCRASQDIRNY

LNWYQQKPDGTVKLLIYYTSRLHSGVPSRFSGSGSGTDYSLTISNLEQEDI

ATYFCQQGNTLPWTFGGGTKLEIKRTVAAPSVFIFPPSDEQLKSGTASVVC

LLNNFYPREAKVQWKVDNALQSGNSQESVTEQDSKDSTYSLSSTLTLSKAD

YEKHKVYACEVTHQGLSSPVTKSFNRGEC

Antibodies or antigen-binding fragments thereof of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a IgA-, IgD-, IgE-, IgG- and IgM-type heavy chain constant region. In various embodiments, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16, 2002.

In various embodiments, an antibody of the invention further comprises a light chain kappa or lambda constant domain, or a fragment thereof, and further comprises a heavy chain constant domain, or a fragment thereof. Sequences of the light chain constant region and heavy chain constant region used in the exemplified antibodies, and polynucleotides encoding them, are provided below.

Light Chain (Kappa) Constant Region
(SEQ ID NO: 53)
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC

Light Chain (Lambda) Constant Region
(SEQ ID NO: 54)
QPKAAPSVTLFPPSSEELQANKATLVCLISDFYPGAVTVAWKADSSPVKAG

VETTTPSKQSNNKYAASSYLSLTPEQWKSHRSYSCQVTHEGSTVEKTVAPT

ECS

Heavy Chain Constant Region
(SEQ ID NO: 55)
TKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCD

KTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSC

SVMHEALHNHYTQKSLSLSPGK

In various embodiments of the present invention, the antibody or antigen-binding fragment is a humanized antibody derived from murine antibody A6 (2G2E2D8).

Examples of Humanized OX40 Antibodies

| HC | LC |
|---|---|
| SEQ ID NO: 86 | SEQ ID NO: 93 |
| SEQ ID NO: 86 | SEQ ID NO: 94 |
| SEQ ID NO: 86 | SEQ ID NO: 95 |
| SEQ ID NO: 86 | SEQ ID NO: 96 |
| SEQ ID NO: 86 | SEQ ID NO: 97 |
| SEQ ID NO: 86 | SEQ ID NO: 98 |
| SEQ ID NO: 86 | SEQ ID NO: 99 |
| SEQ ID NO: 87 | SEQ ID NO: 93 |
| SEQ ID NO: 87 | SEQ ID NO: 94 |
| SEQ ID NO: 87 | SEQ ID NO: 95 |
| SEQ ID NO: 87 | SEQ ID NO: 96 |
| SEQ ID NO: 87 | SEQ ID NO: 97 |
| SEQ ID NO: 87 | SEQ ID NO: 98 |
| SEQ ID NO: 87 | SEQ ID NO: 99 |
| SEQ ID NO: 88 | SEQ ID NO: 93 |
| SEQ ID NO: 88 | SEQ ID NO: 94 |
| SEQ ID NO: 88 | SEQ ID NO: 95 |
| SEQ ID NO: 88 | SEQ ID NO: 96 |
| SEQ ID NO: 88 | SEQ ID NO: 97 |
| SEQ ID NO: 88 | SEQ ID NO: 98 |
| SEQ ID NO: 88 | SEQ ID NO: 99 |
| SEQ ID NO: 89 | SEQ ID NO: 93 |
| SEQ ID NO: 89 | SEQ ID NO: 94 |
| SEQ ID NO: 89 | SEQ ID NO: 95 |
| SEQ ID NO: 89 | SEQ ID NO: 96 |
| SEQ ID NO: 89 | SEQ ID NO: 97 |
| SEQ ID NO: 89 | SEQ ID NO: 98 |

| HC | LC |
| --- | --- |
| SEQ ID NO: 89 | SEQ ID NO: 99 |
| SEQ ID NO: 90 | SEQ ID NO: 93 |
| SEQ ID NO: 90 | SEQ ID NO: 94 |
| SEQ ID NO: 90 | SEQ ID NO: 95 |
| SEQ ID NO: 90 | SEQ ID NO: 96 |
| SEQ ID NO: 90 | SEQ ID NO: 97 |
| SEQ ID NO: 90 | SEQ ID NO: 98 |
| SEQ ID NO: 90 | SEQ ID NO: 99 |
| SEQ ID NO: 91 | SEQ ID NO: 93 |
| SEQ ID NO: 91 | SEQ ID NO: 94 |
| SEQ ID NO: 91 | SEQ ID NO: 95 |
| SEQ ID NO: 91 | SEQ ID NO: 96 |
| SEQ ID NO: 91 | SEQ ID NO: 97 |
| SEQ ID NO: 91 | SEQ ID NO: 98 |
| SEQ ID NO: 91 | SEQ ID NO: 99 |
| SEQ ID NO: 92 | SEQ ID NO: 93 |
| SEQ ID NO: 92 | SEQ ID NO: 94 |
| SEQ ID NO: 92 | SEQ ID NO: 95 |
| SEQ ID NO: 92 | SEQ ID NO: 96 |
| SEQ ID NO: 92 | SEQ ID NO: 97 |
| SEQ ID NO: 92 | SEQ ID NO: 98 |
| SEQ ID NO: 92 | SEQ ID NO: 99 |

In various embodiments, the antibody may be an OX40 antibody which binds to the same epitope as the antibody comprising the heavy chain sequence as set forth in any of SEQ ID NOs: 86-92. In various embodiments, the antibody is an OX40 antibody which competes with the antibody comprising the heavy chain sequence as set forth in any of SEQ ID NOs: 86-92. In various embodiments, the antibody may be an OX40 antibody which comprises at least one (such as two or three) CDRs of the heavy chain sequence as set forth in any of SEQ ID NOs: 86-92. In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 86-92. In various embodiments, the antibody contains a nucleic acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 100-106.

In various embodiments, the antibody may be an OX40 antibody which binds to the same epitope as the antibody comprising the light chain sequence as set forth in any of SEQ ID NOs: 93-99. In various embodiments, the antibody is an OX40 antibody which competes with the antibody comprising the light chain sequence as set forth in any of SEQ ID NOs: 93-99. In various embodiments, the antibody may be an OX40 antibody which comprises at least one (such as two or three) CDRs of the light chain sequence as set forth in any of SEQ ID NOs: 93-99. In various embodiments, the antibody contains an amino acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 93-99. In various embodiments, the antibody contains a nucleic acid sequence that shares an observed homology of, e.g., at least 70%, at least 75%, at least 80%, at least 85%, at least 90%, at least 95%, at least 96%, at least 97%, at least 98%, or at least 99% with any of SEQ ID NOs: 107-113.

In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 97. In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 98. In various embodiments, an isolated humanized antibody or antigen-binding fragment thereof of the present invention binds to human OX40 and comprises the heavy chain sequence set forth in SEQ ID NO: 91, and the light chain sequence set forth in SEQ ID NO: 99.

In various embodiments of the present invention, the antibody is a humanized IgG comprising the heavy chain sequence of SEQ ID NO: 91 and wherein amino acids 1-19 are a leader sequence:

(SEQ ID NO: 91)
MGWSWILLFLLSVTAGVHSEVQLVQSGAEVKKPGESLKISCKGSGYTFTSY

VMHWVRQMPGKGLEWMGYINPYNDGTKYNEKFKGQVTISADKSISTAYLQW

SSLKASDTAMYYCARYYGSNYAMDYWGQGTMVTVSSASTKGPSVFPLAPSS

KSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQP

ENNYKTIPPVLDSDGSFFLYSKLTVDKSRWQQGNVFSCSVMHEALHNHYTQ

KSLSLSPGK and the light chain sequence of SEQ ID NO: 97 and wherein amino acids 1-19 are a leader sequence:

(SEQ ID NO: 97)
MGWSWILLFLLSVTAGVHSDIQMTQSPSSLSASVGDRVTISCRASQDIRNY

LNWYQQKPGKTVKLLIYYTSRLHSGVPSRFSGSGSGTDYTFTISSLQPEDI

ATYFCQQGNTLPWTFGGGTKLEIKRTVAAPSVFIFPPSDEQLKSGTASVVC

LLNNFYPREAKVQWKVDNALQSGNSQESVTEQDSKDSTYSLSSTLTLSKAD

YEKHKVYACEVTHQGLSSPVTKSFNRGEC

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 91, or its corresponding polynucleotide sequence SEQ ID NO: 105:

(SEQ ID NO: 105)
atgggctggagctggatcctgctgttcctcctgagcgtgacagcaggagtg cacagcgaagtgcagctggtgcagagcggggcagaagtgaagaagcctggg gaaagcctgaagattagttgtaaagggagcggatatacattcacttcttac gtgatgcactgggtccggcagatgccaggcaagggactggagtggatggga tacatcaacccttataatgacggcaccaaatataacgaaaagttcaaaggg caggtgaccatctcagcagacaagtctattagtacagcctacctgcagtgg

```
agctccctgaaagccagcgacacagctatgtactattgcgctagatattat ggctcaaactacgctatggactactggggacaggggactatggtcaccgtc tcaagcgctagcaccaagggcccatcggtcttcccctggcaccctcctcc aagagcacctctgggggcacagcggccctgggctgcctggtcaaggactac ttccccgaaccggtgacggtgtcgtggaactcaggcgccctgaccagcggc gtgcacaccttcccggctgtcctacagtcctcaggactctactccctcagc agcgtggtgaccgtgccctccagcagcttgggcacccagacctacatctgc aacgtgaatcacaagcccagcaacaccaaggtggacaagaaagttgagccc aaatcttgtgacaaaactcacacatgcccaccgtgcccagcacctgaactc ctggggggaccgtcagtcttcctcttcccccaaaacccaaggacaccctc atgatctcccggacccctgaggtcacatgcgtggtggtggacgtgagccac gaagaccctgaggtcaagttcaactggtacgtggacggcgtggaggtgcat aatgccaagacaaagccgcgggaggagcagtacaacagcacgtaccgtgtg gtcagcgtcctcaccgtcctgcaccaggactggctgaatggcaaggagtac aagtgcaaggtctccaacaaagccctcccagcccccatcgagaaaaccatc tccaaagccaaagggcagccccgagaaccacaggtgtacaccctgccccca tcccgggatgagctgaccaagaaccaggtcagcctgacctgcctggtcaaa ggcttctatcccagcgacatcgccgtggagtgggagagcaatgggcagccg gagaacaactacaagaccacgcctcccgtgctggactccgacggctccttc ttcctctacagcaagctcaccgtggacaagagcaggtggcagcaggggaac gtcttctcatgctccgtgatgcatgaggctctgcacaaccactacacgcag aagagcctctccctgtctccgggtaaatga
``` and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 97, or its corresponding polynucleotide sequence SEQ ID NO: 111:

```
(SEQ ID NO: 111)
atgggctggagctggatcctgctgttcctcctgagcgtgacagcaggagtg cacagcgacattcagatgacccagagcccttccagcctgagtgcttccgtc ggggatagagtgacaattagttgcagagccagccaggacattaggaactac ctgaattggtatcagcagaagcccggcaaaactgtgaagctgctgatctac tataccagccggctgcactccggggtccctagtagattctctggcagtggg tcaggaacagactacacctttacaatcagctccctgcagcccgaggatatt gccacctatttctgtcagcagggaaatactctgccttggaccttcggcggc ggaactaaactggaaatcaaacgaacggtggctgcaccatctgtcttcatc ttcccgccatctgatgagcagttgaaatctggaactgcctctgttgtgtgc ctgctgaataacttctatcccagagaggccaaagtacagtggaaggtggat aacgccctccaatcgggtaactcccaggagagtgtcacagagcaggacagc aaggacagcacctacagcctcagcagcaccctgacgctgagcaaagcagac
```

```
tacgagaaacacaaagtctacgcctgcgaagtcacccatcagggcctgagc tcgcccgtcacaaagagcttcaacaggggagagtgttag
```

In various embodiments of the present invention, the antibody is a humanized IgG comprising the heavy chain sequence of SEQ ID NO: 91 and wherein amino acids 1-19 are a leader sequence and the light chain sequence of SEQ ID NO: 98 and wherein amino acids 1-19 are a leader sequence:

```
(SEQ ID NO: 98)
MGWSWILLFLLSVTAGVHSEIVLTQSPATLSLSPGERATLSCRASQDIRNY

LNWYQQKPGQAPRLLIYYTSRLHSGIPARFSGSGSGTDFTLTISSLEPEDF

AVYYCQQGNTLPWTFGQGTKVEIKRTVAAPSVFIFPPSDEQLKSGTASVVC

LLNNFYPREAKVQWKVDNALQSGNSQESVTEQDSKDSTYSLSSTLTLSKAD

YEKHKVYACEVTHQGLSSPVTKSFNRGEC
```

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 91, or its corresponding polynucleotide sequence SEQ ID NO: 105, and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 98, or its corresponding polynucleotide sequence SEQ ID NO: 112:

```
(SEQ ID NO: 112)
atgggctggagctggatcctgctgttcctcctgagcgtgacagcaggagtg cacagcgaaatcgtgctgacccagtccccgccacactgagtctgtccccc ggagaaagagccaccctgagctgtagggcaagccaggatattcggaactac ctgaattggtatcagcagaagccaggacaggcacctcgactgctgatctac tatactagcagactgcactctgggattccagctaggttctctggcagtggg tcaggaaccgactttaccctgacaatcagctccctggagcccgaagatttc gccgtgtactattgccagcaggggaatactctgccttggaccttcggccag gggactaaagtggaaatcaaacgaacggtggctgcaccatctgtcttcatc ttcccgccatctgatgagcagttgaaatctggaactgcctctgttgtgtgc ctgctgaataacttctatcccagagaggccaaagtacagtggaaggtggat aacgccctccaatcgggtaactcccaggagagtgtcacagagcaggacagc aaggacagcacctacagcctcagcagcaccctgacgctgagcaaagcagac tacgagaaacacaaagtctacgcctgcgaagtcacccatcagggcctgagc tcgcccgtcacaaagagcttcaacaggggagagtgttag
```

In various embodiments of the present invention, the antibody is a humanized IgG comprising the heavy chain sequence of SEQ ID NO: 91 and wherein amino acids 1-19 are a leader sequence and the light chain sequence of SEQ ID NO: 99 and wherein amino acids 1-19 are a leader sequence:

```
                                              (SEQ ID NO: 99)
MGWSWILLFLLSVTAGVHSEIVMTQSPATLSASPGERVTLSCRASQDIRNY

LNWYQQKPGGAVRLLIYYTSRLHSGVPARFSGSGSGTDYTLTISSLEPEDY

AVYFCQQGNTLPWTFGQGTKVEIKRTVAAPSVFIFPPSDEQLKSGTASVVC

LLNNFYPREAKVQWKVDNALQSGNSQESVTEQDSKDSTYSLSSTLTLSKAD

YEKHKVYACEVTHQGLSSPVTKSFNRGEC
```

In certain alternative embodiments, the antibody is an antibody comprising a heavy chain and a light chain, wherein the heavy chain comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 91, or its corresponding polynucleotide sequence SEQ ID NO: 105, and wherein the light chain comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 99, or its corresponding polynucleotide sequence SEQ ID NO: 113:

```
                                              (SEQ ID NO: 113)
atgggctggagctggatcctgctgttcctcctgagcgtgacagcaggagtg cacagcgaaatcgtgatgacccagagcccagccacactgtccgccagccca ggcgagagagtcacactgtcttgccgagccagccaggatattcggaactac ctgaattggtatcagcagaagccaggaggagccgtgcggctgctgatctac tatactagcagactgcactctggcgtccctgctaggttctctggaagtggc tcagggaccgactacaccctgacaattagctccctggagcccgaagattac gccgtgtattttgccagcaggaaatactctgccttggacattcggacag gggactaaagtggaaatcaaacgaacggtggctgcaccatctgtcttcatc ttcccgccatctgatgagcagttgaaatctggaactgcctctgttgtgtgc ctgctgaataacttctatcccagagaggccaaagtacagtggaaggtggat aacgccctccaatcgggtaactcccaggagagtgtcacagagcaggacagc aaggacagcacctacagcctcagcagcaccctgacgctgagcaaagcagac tacgagaaacacaaagtctacgcctgcgaagtcacccatcagggcctgagc tcgcccgtcacaaagagcttcaacaggggagagtgttag
```

Antibodies of the present invention may also be described or specified in terms of their cross-reactivity. Antibodies that bind OX40 polypeptides, which have at least 95%, at least 90%, at least 85%, at least 80%, at least 75%, at least 70%, at least 65%, at least 60%, at least 55%, and at least 50% identity (as calculated using methods known in the art and described herein) to human OX40 are also included in the present invention.

Further included in the present invention are antibodies that bind to the same epitope as the OX40 antibodies of the present invention. To determine if an antibody can compete for binding to the same epitope as the epitope bound by the OX40 antibodies of the present invention, a cross-blocking assay, e.g., a competitive ELISA assay, can be performed. In an exemplary competitive ELISA assay, OX40 coated on the wells of a microtiter plate is pre-incubated with or without candidate competing antibody and then the biotin-labeled OX40 antibody of the invention is added. The amount of labeled OX40 antibody bound to the OX40 antigen in the wells is measured using avidin-peroxidase conjugate and appropriate substrate. The antibody can be labeled with a radioactive or fluorescent label or some other detectable and measurable label. The amount of labeled OX40 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an OX40 antibody of the invention if the candidate antibody can block binding of the OX40 antibody by at least 20%, by at least 30%, by at least 40%, or by at least 50% as compared to the control performed in parallel in the absence of the candidate competing antibody. It will be understood that variations of this assay can be performed to arrive at the same quantitative value.

In certain alternative embodiments, the antibodies of the present invention can be engineered by modifying one or more residues within one or both variable regions (i.e., $V_H$ and/or $V_L$), or by modifying residues within the constant region(s), e.g., to alter the effector function(s) of the antibody. In various embodiments, the variable region of the antibody will by modified by performing CDR grafting using framework sequences can be obtained from public DNA databases or published references that include germline antibody gene sequences (e.g., Tomlinson, I. M., et al., J. Mol. Biol. 227:776-798, 1992; and Cox, J. P. L. et al., Eur. J. Immunol. 24:827-836, 1994; the contents of each of which are expressly incorporated herein by reference). In various embodiments, the antibodies may be modified using site-directed mutagenesis or PCR-mediated mutagenesis to introduce a mutation(s) in the VH and/or VL which improves binding affinity and/or decreases immunogenicity. In various embodiments, the antibodies may be modified in the Fc region for purposes of altering the serum half-life, complement fixation, Fc receptor binding, and/or antigen-dependent cellular cytotoxicity of the antibody. In various embodiments, the antibodies may be modified for purposes of modifying the glycosylation of the antibody. Methods for performing each of the modifications described herein, and others, are well known to the skilled artisan.

Pharmaceutical Compositions

In one aspect, the present invention provides a pharmaceutical composition comprising an antibody or antigen-binding fragment thereof as described above. The pharmaceutical compositions, methods and uses of the invention thus also encompass embodiments of combinations (co-administration) with other active agents, as detailed below.

Generally, the antibodies, or antigen-binding fragments thereof antibodies of the present invention are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Various embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the OX40 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurized container, pump, spray, atomizer (preferably an atomizer using electrohydrodynamics to produce a fine mist), or nebulizer, with or without the use of a suitable propellant, or as nasal drops.

The pressurized container, pump, spray, atomizer, or nebulizer generally contains a solution or suspension of an antibody of the invention comprising, for example, a suitable agent for dispersing, solubilizing, or extending release of the active, a propellant(s) as solvent.

Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the compound of the invention, a suitable powder base and a performance modifier.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate- and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Pharmaceutical compositions intended for oral use may be prepared according to any method known to the art for the manufacture of pharmaceutical compositions and such compositions may contain one or more agents selected from the group consisting of sweetening agents in order to provide a pharmaceutically elegant and palatable preparation. For example, to prepare orally deliverable tablets, the antibody or antigen-binding fragment thereof is mixed with at least one pharmaceutical excipient, and the solid formulation is compressed to form a tablet according to known methods, for delivery to the gastrointestinal tract. The tablet composition is typically formulated with additives, e.g. a saccharide or cellulose carrier, a binder such as starch paste or methyl cellulose, a filler, a disintegrator, or other additives typically usually used in the manufacture of medical preparations. To prepare orally deliverable capsules, DHEA is mixed with at least one pharmaceutical excipient, and the solid formulation is placed in a capsular container suitable for delivery to the gastrointestinal tract. Compositions comprising antibodies or antigen-binding fragments thereof may be prepared as described generally in Remington's Pharmaceutical Sciences, 18th Ed. 1990 (Mack Publishing Co. Easton Pa. 18042) at Chapter 89, which is herein incorporated by reference.

In various embodiments, the pharmaceutical compositions are formulated as orally deliverable tablets containing antibodies or antigen-binding fragments thereof in admixture with non-toxic pharmaceutically acceptable excipients which are suitable for manufacture of tablets. These excipients may be inert diluents, such as calcium carbonate, sodium carbonate, lactose, calcium phosphate or sodium phosphate; granulating and disintegrating agents, for example, maize starch, gelatin or acacia, and lubricating agents, for example, magnesium stearate, stearic acid, or talc. The tablets may be uncoated or they may be coated with known techniques to delay disintegration and absorption in the gastrointestinal track and thereby provide a sustained action over a longer period of time. For example, a time delay material such as glyceryl monostearate or glyceryl distearate alone or with a wax may be employed.

In various embodiments, the pharmaceutical compositions are formulated as hard gelatin capsules wherein the antibody or antigen-binding fragment thereof is mixed with an inert solid diluent, for example, calcium carbonate, calcium phosphate, or kaolin or as soft gelatin capsules wherein the antibody or antigen-binding fragment thereof is mixed with an aqueous or an oil medium, for example, arachis oil, peanut oil, liquid paraffin or olive oil.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Therapeutic And Diagnostic Uses

In another aspect, the present invention relates to methods for enhancing the immune response to cancerous cells in a subject, comprising administering to the subject a therapeutically effective amount (either as monotherapy or in a combination therapy regimen) of an isolated antibody or antigen-binding fragment of the present invention. In various embodiments, the present invention provides for a method of treating cancerous cells in a subject, comprising administering to said subject a therapeutically effective amount (either as monotherapy or in a combination therapy regimen) of an antibody or antigen-binding fragment thereof of the present invention. In various embodiments, the cancerous cell is associated with elevated expression of OX40.

Cancerous cells that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, lymphoma, melanoma, Kaposi's sarcoma, Ewing's tumor, leiomyosarcoma, rhabdomyosarcoma, colo-rectal carcinoma, gastric carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In various embodiments, the cancerous cell is selected from the group consisting of ovarian cancer, lung cancer, breast cancer, gastric cancer, prostate cancer, colon cancer, renal cell cancer, glioblastoma, and melanoma.

In various embodiments, the subject previously responded to treatment with an anti-cancer therapy, but, upon cessation of therapy, suffered relapse (hereinafter "a recurrent cancer"). In various embodiments, the subject has resistant or refractory cancer. In various embodiments, the cancerous cells are immunogenic tumors (e.g., those tumors for which vaccination using the tumor itself can lead to immunity to tumor challenge).

In various embodiments, the present antibodies and antigen-binding fragments thereof can be utilized to directly kill or ablate cancerous cells in vivo. Direct killing involves administering the antibodies (which are optionally fused to a cytotoxic drug) to a subject requiring such treatment. In various embodiments, the cancer comprises cancer cells expressing OX40 at a higher level than noncancerous cells of a comparable tissue. Since the antibodies recognize OX40 on cancer cells, any such cells to which the antibodies bind are destroyed. Where the antibodies are used alone to kill or ablate cancer cells, such killing or ablation can be effected by initiating endogenous host immune functions, such as CDC and/or ADCC. Assays for determining whether an antibody kills cells in this manner are within the purview of those skilled in the art.

In various embodiments, the present antibodies and antigen-binding fragments thereof can be utilized to promote growth inhibition and/or proliferation of a cancerous tumor cell. These methods may inhibit or prevent the growth of the cancer cells of said subject, such as for example, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. As a result, where the cancer is a solid tumor, the modulation may reduce the size of the solid tumor by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

The inhibition of the cancer cell proliferation can be measured by cell-based assays, such as bromodeoxyuridine (BRDU) incorporation (Hoshino et al., Int. J. Cancer 38, 369, 1986; Campana et al., J. Immunol. Meth. 107:79, 1988; [$^3$H]-thymidine incorporation (Chen, J., Oncogene 13:1395-403, 1996; Jeoung, J., J. Biol. Chem. 270:18367-73, 1995; the dye Alamar Blue (available from Biosource International) (Voytik-Harbin et al., In Vitro Cell Dev Biol Anim 34:239-46, 1998). The anchorage independent growth of cancer cells is assessed by colony formation assay in soft agar, such as by counting the number of cancer cell colonies formed on top of the soft agar (see Examples and Sambrook et al., Molecular Cloning, Cold Spring Harbor, 1989).

The inhibition of cancer cell growth in a subject may be assessed by monitoring the cancer growth in a subject, for example in an animal model or in human subjects. One exemplary monitoring method is tumorigenicity assays. In one example, a xenograft comprises human cells from a pre-existing tumor or from a tumor cell line. Tumor xenograft assays are known in the art and described herein (see, e.g., Ogawa et al., Oncogene 19:6043-6052, 2000). In another embodiment, tumorigenicity is monitored using the hollow fiber assay, which is described in U.S. Pat. No. 5,698,413, which is incorporated herein by reference in its entirety.

The percentage of the inhibition is calculated by comparing the cancer cell proliferation, anchorage independent growth, or cancer cell growth under modulator treatment with that under negative control condition (typically without modulator treatment). For example, where the number of cancer cells or cancer cell colonies (colony formation assay), or PRDU or [$^3$H]-thymidine incorporation is A (under the treatment of modulators) and C (under negative control condition), the percentage of inhibition would be (C−A)/C× 100%.

Examples of tumor cell lines derived from human tumors and available for use in the in vitro and in vivo studies include, but are not limited to, leukemia cell lines (e.g., CCRF-CEM, HL-60(TB), K-562, MOLT-4, RPM1-8226, SR, P388 and P388/ADR); non-small cell lung cancer cell lines (e.g., A549/ATCC, EKVX, HOP-62, HOP-92, NCI-H226, NCI-H23, NCI-H322M, NCI-H460, NCI-H522 and LXFL 529); small cell lung cancer cell lines (e.g., DMS 114 and SHP-77); colon cancer cell lines (e.g., COLO 205, HCC-2998, HCT-116, HCT-15, HT29, KM12, SW-620, DLD-1 and KM20L2); central nervous system (CNS) cancer cell lines (e.g., SF-268, SF-295, SF-539, SNB-19, SNB-75, U251, SNB-78 and XF 498); melanoma cell lines (e.g., LOX I MVI, MALME-3M, M14, SK-MEL-2, SK-MEL-28, SK-MEL-5, UACC-257, UACC-62, RPMI-7951 and M19-MEL); ovarian cancer cell lines (e.g., IGROV, OVCAR-3, OVCAR-4, OVCAR-5, OVCAR-8 and SK-OV-3); renal cancer cell lines (e.g., 786-0, A498, ACHN, CAKI-1, RXF 393, SN12C, TK-10, UO-31, RXF-631 and SN12K1); prostate cancer cell lines (e.g., PC-3 and DU-145); breast cancer cell lines (e.g., MCF7, NCI/ADR-RES, MDA-MB-231/ATCC, HS 578T, MDA-MB-435, BT-549, T-47D and MDA-MB-468); and thyroid cancer cell lines (e.g., SK-N-SH).

In various embodiments, the present invention relates to methods for stimulating an immune response to pathogens, toxins and self-antigens in a subject, comprising administering to the subject a therapeutically effective amount (either as monotherapy or in a combination therapy regimen) of an isolated antibody or antigen-binding fragment of the present invention. In various embodiments, the subject has an infectious disease that is resistant to, or ineffectively treated by, treatment using conventional vaccines.

Pathogens contemplated for treatment include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania*, *Staphylococcus aureus*, and *Pseudomonas aeruginosa*. Pathogenic viruses causing infections treatable by methods of the invention include hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria. Pathogenic fungi causing infections treatable by methods of the invention include *Candida* (*albicans, krusei, glabrata, tropicalis*, etc.), *Cryptococcus neoformans*, *Aspergillus* (*fumigatus, niger*, etc.), Genus *Mucorales* (*Mucor, Absidia, Rhizophus*), *Sporothrix schenkii, Blastomyces dermatitidis, Paracoccidioides brasiliensis, Coccidioides immitis* and *Histoplasma capsulatum*. Pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

"Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an IC$_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the antibodies or antigen-binding fragments thereof of the disclosure can be in the range of 0.5-1200 mg per subject, 0.5-1100 mg per subject, 0.5-1000 mg per subject, 0.5-900 mg per subject, 0.5-800 mg per subject, 0.5-700 mg per subject, 0.5-600 mg per subject, 0.5-500 mg per subject, 0.5-400 mg per subject, 0.5-300 mg per subject, 0.5-200 mg per subject, 0.5-100 mg per subject, 0.5-50 mg per subject, 1-1200 mg per subject, 1-1100 mg per subject, 1-1000 mg per subject, 1-900 mg per subject, 1-800 mg per subject, 1-700 mg per subject, 1-600 mg per subject, 1-500 mg per subject, 1-400 mg per subject, 1-300 mg per subject, 1-200 mg per subject, 1-100 mg per subject, or 1-50 mg per subject depending, of course, on the mode of administration. For example, an intravenous monthly dose can require about 1-1000 mg/subject. In various embodiments, the antibodies or antigen-binding fragments thereof of the disclosure can be administered at about 1-200 mg per subject, 1-150 mg per subject or 1-100 mg/subject. The total monthly dose can be administered in single or divided doses and can, at the physician's discretion, fall outside of the typical ranges given herein.

An exemplary, non-limiting daily dosing range for a therapeutically or prophylactically effective amount of an antibody or antigen-binding fragment thereof of the disclosure can be 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 µg/ml, about 1 to 750 µg/ml, about 1 to 500 µg/ml, about 1 to 250 µg/ml, about 10 to 1000 µg/ml, about 10 to 750 µg/ml, about 10 to 500 µg/ml, about 10 to 250 µg/ml, about 20 to 1000 µg/ml, about 20 to 750 µg/ml, about 20 to 500 µg/ml, about 20 to 250 µg/ml, about 30 to 1000 µg/ml, about 30 to 750 µg/ml, about 30 to 500 µg/ml, about 30 to 250 µg/ml.

Toxicity and therapeutic index of the pharmaceutical compositions of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

In various embodiments, single or multiple administrations of the pharmaceutical compositions are administered depending on the dosage and frequency as required and tolerated by the subject. In any event, the composition should provide a sufficient quantity of at least one of the antibodies or antigen-binding fragments thereof disclosed herein to effectively treat the subject. The dosage can be administered once but may be applied periodically until either a therapeutic result is achieved or until side effects warrant discontinuation of therapy.

The dosing frequency of the administration of the antibody or antigen-binding fragment thereof pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the antibodies or antigen-binding fragments thereof of the disclosure and one or more other therapeutic agents, is intended to mean, and does refer to and include the following: simultaneous administration of such combination of antibodies or antigen-binding fragments thereof of the disclosure and therapeutic agent(s) to a subject in need of treatment, when such components are formulated together into a single dosage form which releases said components at substantially the same time to said subject; substantially simultaneous administration of such combination of antibodies or antigen-binding fragments thereof of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of antibodies or antigen-binding fragments thereof of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of antibodies or antigen-binding fragments thereof of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present invention relates to combination therapies designed to treat a cancer in an subject, comprising administering to the subject a therapeutically effective amount of an isolated antibody or antigen-binding fragment of the present invention, and b) one or more additional therapies selected from the group consisting of immunotherapy, chemotherapy, small molecule kinase inhibitor targeted therapy, surgery, radiation therapy, and stem cell transplantation, wherein the combination therapy provides increased cell killing of tumor cells, i.e., a synergy exists between the isolated antibody or antigen-binding fragment and the additional therapies when co-administered.

In various embodiments, the immunotherapy is selected from the group consisting of: treatment using agonistic, antagonistic, or blocking antibodies to co-stimulatory or co-inhibitory molecules (immune checkpoints) such as PD-1, PD-L1, OX-40, CD137, GITR, LAG3, TIM-3, and VISTA; treatment using bispecific T cell engaging antibodies (BiTE®) such as blinatumomab: treatment involving administration of biological response modifiers such as IL-2, IL-12, IL-15, IL-21, GM-CSF and IFN-α, IFN-β and IFN-γ; treatment using therapeutic vaccines such as sipuleucel-T; treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

A wide array of conventional compounds have been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments When the antibody or antigen-binding fragment disclosed herein is administered in combination with another conventional anti-neoplastic agent, either concomitantly or sequentially, such antibody or antigen-binding fragment may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant T-cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In various embodiments, the chemotherapy comprises a chemotherapeutic agent selected from the group consisting of: daunorubicin, dactinomycin, doxorubicin, bleomycin, mitomycin, nitrogen mustard, chlorambucil, melphalan, cyclophosphamide, 6-mercaptopurine, 6-thioguanine, bendamustine, cytarabine (CA), 5-fluorouracil (5-FU), floxuridine (5-FUdR), methotrexate (MTX), colchicine, vincristine, vinblastine, etoposide, teniposide, cisplatin, carboplatin, oxaliplatin, pentostatin, cladribine, cytarabine, gemcitabine, pralatrexate, mitoxantrone, diethylstilbestrol (DES), fluradabine, ifosfamide, hydroxyureataxanes (such as paclitaxel and doxetaxel) and/or anthracycline antibiotics, as well as combinations of agents such as, but not limited to, DA-EPOCH, CHOP, CVP or FOLFOX.

In various embodiments, the small molecule kinase inhibitor targeted therapy comprises a small molecule kinase inhibitor selected from the group consisting of Bruton's tyrosine kinase (BTK) inhibitor, phosphatidylinositol-3-kinase (P3K) inhibitor, SYK inhibitor (e.g., entospletinib), AKT inhibitor, mTOR inhibitor, Src inhibitor, JAK/STAT inhibitor, Ras/Raf/MEK/ERK inhibitor, and Aurora inhibitor (see, D'Cruz et al, Expert Opin Pharmacother, 14(6): 707-21, 2013).

In various embodiments, the combination therapy comprises administering the antibody or antigen-binding fragment thereof and the one or more additional therapies simultaneously. In various embodiments, antibody or antigen-binding fragment thereof composition and the one or more additional therapies are administered sequentially, i.e., the antibody or antigen-binding fragment thereof composition is administered either prior to or after the administration of the one or more additional therapies.

In various embodiments, the administrations of the antibody or antigen-binding fragment thereof composition and the one or more additional therapies are concurrent, i.e., the administration period of the antibody or antigen-binding fragment thereof composition and the one or more additional therapies overlap with each other.

In various embodiments, the administrations of the antibody or antigen-binding fragment thereof composition and the one or more additional therapies are non-concurrent. For example, in various embodiments, the administration of the antibody or antigen-binding fragment thereof composition is terminated before the one or more additional therapies is administered. In various embodiments, the administration of the one or more additional therapies is terminated before the antibody or antigen-binding fragment thereof composition is administered.

When the antibody or antigen-binding fragment thereof disclosed herein is administered in combination with one or more additional therapies, either concomitantly or sequentially, such antibody or antigen-binding fragment thereof may enhance the therapeutic effect of the one or more additional therapies or overcome cellular resistance to the one or more additional therapies. This allows for decreased dosage or duration of the one or more additional therapies, thereby reducing the undesirable side effects, or restores the effectiveness of the one or more additional therapies.

Immunoconjugates

The application further provides immunoconjugates comprising an antibody or antigen-binding fragment thereof of the present invention conjugated (or linked) directly or indirectly to an effector molecule. In this regard, the term "conjugated" or "linked" refers to making two polypeptides into one contiguous polypeptide molecule. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. In various embodiments, an antibody or antigen-binding fragment is joined to an effector molecule. In other embodiments, an antibody or antigen-binding fragment joined to an effector molecule is further joined to a lipid, a protein or peptide to increase its half-life in the body. Accordingly in various embodiments, the antibodies of the present disclosure may be used to deliver a variety of effector molecules.

The effector molecule can be a detectable label, an immunotoxin, cytokine, chemokine, therapeutic agent, or chemotherapeutic agent.

Specific, non-limiting examples of immunotoxins include, but are not limited to, abrin, ricin, Pseudomonas exotoxin (PE, such as PE35, PE37, PE38, and PE40), diphtheria toxin (DT), botulinum toxin, cholix toxin, or modified toxins thereof, or other toxic agents that directly or indirectly inhibit cell growth or kill cells.

A "cytokine" is class of proteins or peptides released by one cell population which act on another cell as intercellular mediators. Cytokines can act as an immune-modulating agent. Examples of cytokines include lymphokines, monokines, growth factors and traditional polypeptide hormones. Thus, embodiments may utilize an interferon (e.g., IFN-α, IFN-β, and IFN-γ); tumor necrosis factor super family (TNFSF) member; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; TNF-α; TNF-β; integrin; thrombopoietin (TPO); a nerve growth factor such as NGF-β; platelet-growth factor; TGF-α; TGF-β; insulin-like growth factor-I and —II; erythropoietin (EPO); colony stimulating factors (CSFs) such as macrophage-CSF (M-CSF); granulocyte-macrophage-CSF (GM-CSF); and granulocyte-CSF (G-CSF); an interleukin (IL-1 to IL-21), kit-ligand or FLT-3, angiostatin, thrombospondin, or endostatin. These cytokine include proteins from natural sources or from recombinant cell culture and biologically active equivalents of the native sequence cytokines.

Chemokines can also be conjugated to the antibodies disclosed herein. Chemokines are a superfamily of small (approximately about 4 to about 14 kDa), inducible and secreted pro-inflammatory cytokines that act primarily as chemoattractants and activators of specific leukocyte cell subtypes. Chemokine production is induced by inflammatory cytokines, growth factors and pathogenic stimuli. The chemokine proteins are divided into subfamilies (alpha, beta, and delta) based on conserved amino acid sequence motifs and are classified into four highly conserved groups—CXC, CC, C and CX3C, based on the position of the first two cysteines that are adjacent to the amino terminus. To date, more than 50 chemokines have been discovered and there are at least 18 human seven-transmembrane-domain (7TM) chemokine receptors. Chemokines of use include, but are not limited to, RANTES, MCAF, MCP-1, and fractalkine.

The therapeutic agent can be a chemotherapeutic agent. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRIGHT. 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Useful chemotherapeutic agents for the preparation of immunoconjugates include auristatin, dolastatin, MMAE, MMAF, AFP, DM1, AEB, doxorubicin, daunorubicin, methotrexate, melphalan, chlorambucil, vinca alkaloids, 5-fluorouridine, mitomycin-C, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbazine, topotecan, nitrogen mustards, cytoxan, etoposide, BCNU, irinotecan, camptothecins, bleomycin, idarubicin, dactinomycin, plicamycin, mitoxantrone, asparaginase, vinblastine, vincristine, vinorelbine, paclitaxel, and docetaxel and salts, solvents and derivatives thereof. In various embodiments, the chemotherapeutic agent is auristatin E (also known in the art as dolastatin-10) or a derivative thereof as well as pharmaceutically salts or solvates thereof. Typical auristatin derivatives include DM1, AEB, AEVB, AFP, MMAF, and MMAE. The synthesis and structure of auristatin E and its derivatives, as well as linkers, are described in, e.g., U.S. Patent Application Publication No. 20030083263; U.S. Patent Application Publication No. 20050238629; and U.S. Pat. No. 6,884,869 (each of which is incorporated by reference herein in its entirety). In various embodiments, the therapeutic agent is an auristatin or an auristatin derivative. In various embodiments, the auristatin derivative is dovaline-valine-dolaisoleunine-dolaproine-phenylalanine (MMAF) or monomethyauristatin E (MMAE). In various embodiments, the therapeutic agent is a maytansinoid or a maytansinol analogue. In various embodiments, the maytansinoid is DM1.

The effector molecules can be linked to an antibody or antigen-binding fragment of the present invention using any number of means known to those of skill in the art. Both covalent and noncovalent attachment means may be used. The procedure for attaching an effector molecule to an antibody varies according to the chemical structure of the effector molecule. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

Procedures for conjugating the antibodies with the effector molecules have been previously described and are within the purview of one skilled in the art. For example, procedures for preparing enzymatically active polypeptides of the immunotoxins are described in WO84/03508 and WO85/03508, which are hereby incorporated by reference for purposes of their specific teachings thereof. Other techniques are described in Shih et al., Int. J. Cancer 41:832-839 (1988); Shih et al., Int. J. Cancer 46:1101-1106 (1990); Shih et al., U.S. Pat. No. 5,057,313; Shih Cancer Res. 51:4192, International Publication WO 02/088172; U.S. Pat. No. 6,884,869; International Patent Publication WO 2005/081711; U.S. Published Application 2003-0130189 A; and US Patent Application No. 20080305044, each of which is incorporated by reference herein for the purpose of teaching such techniques.

An immunoconjugate of the present invention retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate is also referred to as an antibody drug conjugate (ADC).

Diagnostic Uses

In another aspect, the present invention provides a method for detecting in vitro or in vivo the presence of human OX40 antigen in a sample, e.g., for diagnosing a human OX40-related disease. In some methods, this is achieved by contacting a sample to be tested, along with a control sample, with a human sequence antibody or a human monoclonal antibody of the invention, or an antigen-binding portion thereof (or a bispecific or multispecific molecule), under conditions that allow for formation of a complex between the antibody and human OX40. Complex formation is then detected (e.g., using an ELISA) in both samples, and any statistically significant difference in the formation of complexes between the samples is indicative the presence of human OX40 antigen in the test sample.

In various embodiments, methods are provided for detecting cancer or confirming the diagnosis of cancer in a subject. The method includes contacting a biological sample from the subject with an isolated antibody or antigen-biding fragment thereof of the invention and detecting binding of the isolated human monoclonal antibody or antigen-binding fragment thereof to the sample. An increase in binding of the isolated human monoclonal antibody or antigen-binding fragment thereof to the sample as compared to binding of the isolated human monoclonal antibody or antigen-binding fragment thereof to a control sample detects cancer in the subject or confirms the diagnosis of cancer in the subject. The control can be a sample from a subject known not to have cancer, or a standard value. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, and spinal fluid.

In one embodiment, a kit is provided for detecting OX40 in a biological sample, such as a blood sample. Kits for detecting a polypeptide will typically comprise a human antibody that specifically binds OX40, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds OX40. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting OX40 in a biological sample generally includes the steps of contacting the biological sample with an antibody which specifically reacts, under immunologically reactive conditions, to OX40. The antibody is allowed to specifically bind under immunologically reactive conditions to form an immune complex, and the presence of the immune complex (bound antibody) is detected directly or indirectly.

In various embodiments, the antibodies or antigen-binding fragments can be labeled or unlabeled for diagnostic purposes. Typically, diagnostic assays entail detecting the formation of a complex resulting from the binding of an antibody to OX40. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

The antibody or antigen-binding fragment provided herein may also be used in a method of detecting the susceptibility of a mammal to certain diseases. To illustrate, the method can be used to detect the susceptibility of a mammal to diseases which progress based on the amount of OX40 present on cells and/or the number of OX40-positive cells in a mammal. In one embodiment, the application provides a method of detecting susceptibility of a mammal to a tumor. In this embodiment, a sample to be tested is contacted with an antibody which binds to OX40 or portion thereof under conditions appropriate for binding of said antibody thereto, wherein the sample comprises cells which express OX40 in normal individuals. The binding of antibody and/or amount of binding is detected, which indicates the susceptibility of the individual to a tumor, wherein higher levels of receptor correlate with increased susceptibility of the individual to a tumor.

In various embodiments, the antibodies or antigen-binding fragments are attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using antibodies or antigen-binding fragments directed at OX40 may be used to detect and/or diagnose cancers and vasculature. For example, monoclonal antibodies against the OX40 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, or 1-10 millicuries, or 2-5 millicuries are administered. Thus, the compositions disclosed are useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

Bispecific Molecules

In another aspect, the present invention features bispecific molecules comprising an OX40 antibody, or antigen-binding fragment thereof, of the invention. An antibody of the invention, or antigen-binding fragment thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results. In various embodiments, the invention includes bispecific molecules capable of binding both to FcγR or FcαR expressing effector cells (e.g., monocytes, macrophages or polymorphonuclear cells (PMNs)), and to target cells expressing PD. In such embodiments, the bispecific molecules target OX40 expressing cells to effector cell and trigger Fc receptor-mediated effector cell activities, e.g., phagocytosis of an OX40 expressing cells, antibody dependent cell-mediated cytotoxicity (ADCC), cytokine release, or generation of superoxide anion. Methods of preparing the bispecific molecules of the present invention are well known in the art.

Polynucleotides and Antibody Expression

The application further provides polynucleotides comprising a nucleotide sequence encoding an OX40 antibody or antigen-binding fragment thereof. Because of the degeneracy of the genetic code, a variety of nucleic acid sequences encode each antibody amino acid sequence. The application further provides polynucleotides that hybridize under stringent or lower stringency hybridization conditions, e.g., as defined herein, to polynucleotides that encode an antibody that binds to human OX40.

Stringent hybridization conditions include, but are not limited to, hybridization to filter-bound DNA in 6×SSC at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292 (2000)).

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention is also directed to host cells that express a OX40 polypeptide and/or the OX40 antibodies of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors one expressing the heavy chain and one expressing the light chain.

Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably-linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding alight chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may carry additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NS0) for selection/amplification.

For expression of the light and/or heavy chains, the expression vector(s) encoding the heavy and/or light chains is introduced into a host cell by standard techniques e.g. electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g. as described in Kaufman and Sharp, J. Mol. Biol. 159:601-21, 1982], NS0 myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

The invention provides a host cell comprising a nucleic acid molecule of the present invention. Preferably a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably-linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxyapatite chromatography, gel electrophoresis, and the like. Standard procedures for purification of therapeutic antibodies are described, for example, by Feng L1, Joe X. Zhou, Xiaoming Yang, Tim Tressel, and Brian Lee in an article entitled "Current Therapeutic Antibody Production and Process Optimization" (BioProcessing Journal, September/October 2005)(incorporated by reference in its entirety for purposes of teaching purification of therapeutic antibodies). Additionally, standard techniques for removing viruses from recombinantly expressed antibody preparations are also known in the art (see, for example, Gerd Kern and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to an antibody obtainable by a process comprising the steps of culturing a host cell including, but not limited to a mammalian, plant, bacterial, transgenic animal, or transgenic plant cell which has been transformed by a polynucleotide or a vector comprising nucleic acid molecules encoding antibodies of the invention so that the nucleic acid is expressed and, optionally, recovering the antibody from the host cell culture medium.

In certain aspects, the present application provides hybridoma cell lines, as well as to the monoclonal antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the OX40 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged OX40 light or heavy chain can be isolated (e.g., by PCR) or cDNA libraries can be prepared from mRNA isolated from the cell lines, and cDNA clones encoding an OX40 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host T-cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host T-cell by an appropriate method (e.g., transformation, transfection, electroporation, infection), such that the nucleic acid is operably linked to one or more expression control elements (e.g., in the vector or integrated into the host T-cell genome). For production, host T-cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host T-cells or medium). It will be appreciated that the method of production encompasses expression in a host T-cell of a transgenic animal (see e.g., WO 92/03918, GenPharm International, published Mar. 19, 1992)(incorporated by reference in its entirety).

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human OX40. The molecules expressed from such truncated DNA molecules are also encompassed by the antibodies of the invention.

Methods for expression of single chain antibodies and/or refolding to an appropriate active form, including single chain antibodies, from bacteria such as E. coli have been described and are well-known and are applicable to the antibodies disclosed herein (see, e.g., Buchner et al., Anal. Biochem. 205:263-270, 1992; Pluckthun, Biotechnology 9:545, 1991; Huse et al., Science 246:1275, 1989 and Ward et al., Nature 341:544, 1989, all incorporated by reference herein).

Often, functional heterologous proteins from E. coli or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and antigen-binding fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

The following examples are offered to more fully illustrate the invention but are not construed as limiting the scope thereof.

Example 1

Generation of Monoclonal Antibodies Targeting Specifically to Human OX40

Male mice (C57BL/6, BALB/c, SJL) were each immunized subcutaneously at Day 0 with 50 µg of human OX40 (NP_003318) mixed with Complete Freund's Adjuvant (Sigma, St. Louis, Mo.). The primary immunization was followed by two boosts with 25 µg of human OX40 per mouse mixed with Incomplete Freund's Adjuvant (Sigma, St. Louis, Mo.) intraperitoneally or subcutaneously at Day 14 and Day 28. The mice were given a final boost with 25 ug of human OX40 alone intraperitoneally at Day 56, and splenocytes were harvested 4 days later for fusion with myeloma cell line NSO from ATCC (Allendale, N.J.). Electric fusion methods are used to obtain hybridoma cells and then hybridoma supernatants are screened for antigen binding, ligand blocking, IgG binning, reference antibody binding, and FACS binding.

15 MAbs were ultimately selected from the initial screens for subcloning (limited dilution method) and further evaluation. BD Cell MAb Medium was used to grow hybridomas in roller bottles for the collection of supernatants for antibody production. MAbs were purified with Protein A affinity chromatography. Estimated purity of MAbs was higher than 90% based on SDS-PAGE Coomassie staining. The secondary screening of the 15 purified MAbs comprised: human OX40 binding assays (ELISA), murine OX40 binding assays (ELISA), cyno OX40 binding assays (ELISA), OX40/OX40L ligand blocking assays by ELISA and by ForteBio, and epitope binning screening. None of the purified MAbs showed mouse crossreactivity but the lead antibodies crossreact with cyno OX40.

Based on the cumulative results of the secondary assays, purified murine monoclonal antibodies MAbs A1-A6 were selected for further analysis. MAbs A1-A6 comprise the heavy chain variable region sequences set forth in SEQ ID NOs: 30, 32, 34, 36, 38 and 40, respectively, and the light chain variable region sequences set forth in SEQ ID NOs: 42, 44, 46, 48, 50 and 52, respectively. The heavy chain variable regions of MAbs A1-A6 are encoded by the nucleic acid sequences set forth in SEQ ID NOs: 29, 31, 33, 35, 37 and 39, respectively, and the light chain variable regions of MAbs A1-A6 are encoded by the nucleic acid sequences set forth in SEQ ID NOs: 41, 43, 45, 47, 49 and 51, respectively.

The binding assay and blocking assay data for MAbs A1-A6 are summarized in Tables 3 and 4:

Example 2

In vitro cell-based OX40 functional assays were performed to evaluate the agonist potencies of the 15 hybridoma supernatants. Briefly, stable OX40 cells were incubated with 40 µL hybridoma supernatant for 24 hours. The potency of samples was measured by the concentration of interleukin 8 (IL-8) (HTRF Kit, Cisbio Cat #62IL8PEB) secreted by HT1080 OX40 stable cell lines. The internal control 200 ng/ml OX40L (Sino Biological, 13127-H04H) was used to monitor the assay performance.

In vitro cell-based OX40 functional assays were performed to evaluate the antagonist potencies of 24 hybridoma supernatants. Briefly, stable OX40 cells were incubated with 40 µL hybridoma supernatant for 30 minutes and then 10 µL 5×200 ng/mL OX40L was added followed by a 24-hour incubation. The potency of samples was measured by the concentration of interleukin 8 (IL-8) (HTRF Kit, Cisbio Cat #621L8PEB) secreted by HT1080 OX40 stable cell lines.

The assay data for MAbs A1-A6 are summarized in Table 4:

TABLE 4

| MAb (clone) | HT1080 Agonist Assay EC50 (nM) | HT1080 Agonist Assay nBMAX | HT1080 + OX4OL/IL-8 Antagonist Assay IC50 (nM) |
|---|---|---|---|
| A1 (5A8G11B11) | 2.22 | 1.00 | 1.30 |
| A2 (4B12C9D9) | 3.46 | 2.87 | No Effect |
| A3 (14F2C2D7) | 6.74 | 4.49 | No Effect |
| A4 (13C2G10F10) | 8.08 | 1.52 | 1.35 |
| A5 (40H11C2F5) | 2.80 | 3.20 | No Effect |
| A6 (2G2E2D8) | 1.56 | 4.54 | No Effect |

The functional assays identified three distinct mechanisms: Class 1 Agonist which exhibit a bell-shape [Ab] vs effect curve typical of cytokine, growth factors and hormones and do not block OX40L (MAb A3 and MAb A6), Class 2 Agonist which activate OX40 at a lower IC50, and inhibit OX40L binding to receptor (MAb A2 and MAb A5), and Class 3 Antagonist/Weak Agonist which inhibit OX40 activation (MAb A1 and MAb A4).

Example 3

Using the HCVR sequence (SEQ ID NO: 40) and LCVR sequence (SEQ ID NO: 52) of murine MAb A6, a chimeric antibody with human IgG1 (hereinafter "chimeric IgG") was prepared, expressed and purified. The heavy chain sequence of the chimeric IgG is set forth in SEQ ID NO: 84 and the light chain sequence of chimeric IgG is set forth in SEQ ID NO: 85.

TABLE 3

| MAb (clone) | Isotype | Epitope | HuOX40 Binding EC50 (pM) | MuOX40 Binding EC50 (pM) | CyOX40 Binding EC50 (pM) | OX40L/OX40 ELISA Blocking IC50 (pM) |
|---|---|---|---|---|---|---|
| A1 (5A8G11B11) | IgG1, κ | 2, 3 | 17.6, 17.7 | No Binding | 24.65 | 27.24 |
| A2 (4B12C9D9) | IgG1, κ | 2, 3 | 21.8, 22.8 | No Binding | 31.38 | 51.62 |
| A3 (14F2C2D7) | IgG1, κ | 3 | 12.8, 13.6 | No Binding | 17.10 | 29.28 |
| A4 (13C2G10F10) | IgG1, κ | 1 | 15.7, 15.1 | No Binding | 30.48 | 68.31 |
| A5 (40H11C2F5) | IgG1, κ | 4 | 8.1, 7.9 | No Binding | 14.28 | 38.19 |
| A6 (2G2E2D8) | IgG1, κ | 1 | 27.5, 27.2 | No Binding | 44.62 | No Inhibition |

** the IC50 for blocking OX40L to OX40 was obtained with purified proteins, and the ratio of these IC50 was calculated (blocking ratio)

The DNA sequences encoding the chimeric IgG heavy and light chains were synthesized and inserted into pTT5 vector to construct the expression plasmids of full-length IgGs. Expression of chimeric IgG was conducted in HEK293 cell culture and the supernatants were purified with protein A affinity column. The purified antibody was buffer-exchanged into PBS using PD-10 desalting column. The concentration and purity of the purified protein were determined by $OD_{280}$ and SDS-PAGE, respectively. The purified chimeric IgG migrated as 170 kDa band in SDS-PAGE under non-reducing conditions. Evaluating by the SDS-PAGE result, the purity of the IgGs was >95%.

Binding confirmation and the affinity of antibody to Ag OX40-Fc was determined using a Surface Plasmon Resonance (SPR) biosensor, Biacore T200 (GE Healthcare). Antigen OX40-Fc was immobilized on the sensor chip through amine coupling method. Antibody was used as the analyte. The data of dissociation ($k_d$) and association ($k_a$) rate constants were obtained using Biacore T200 evaluation software. The apparent equilibrium dissociation constants ($K_D$) were calculated from the ratio of $k_d$ over $k_a$.

Example 4

The structure of the parental antibody, murine MAb A6, was modelled by computer-aided homology modelling program and humanized IgG1 antibodies were designed using CDR grafting and subsequent replaced putative back mutation sites of grafted antibody. The CDRs of parental antibody were grafted into the human acceptors to obtain humanized light chains and humanized heavy chains for each parental antibody. The sequences of seven humanized heavy chains (referred to as VH1, VH2, VH3, VH4, VH5BM, VH2-1 and VH2-2) are set forth in SEQ ID NOs: 86-92, and the sequences of the variable domains of VH1, VH2, VH3, VH4, VH5BM, VH2-1 and VH2-2 are set forth in SEQ ID NOs: 56-62, respectively. The sequences of seven humanized light chains (referred to as VL1, VL2, VL3, VL4, VL5BM, VL2-1 and VL2-2) are set forth in SEQ ID NOs: 93-99, and the sequences of the variable domains of VL1, VL2, VL3, VL4, VL5BM, VL2-1 and VL2-2 are set forth in SEQ ID NOs: 63-69, respectively.

The DNA sequences encoding the various humanized IgG heavy and light chains were synthesized and inserted into pTT5 vector to construct the expression plasmids of full-length IgGs. Fifteen full-length humanized antibodies were expressed in HEK 293 cell culture, and then the cells were spun down. The supernatants were filtered and conducted with Western-blot and SDS-PAGE analysis. The purified chimeric IgG and humanized IgGs migrated as 170 kDa band in SDS-PAGE under non-reducing conditions. Evaluating by the SDS-PAGE result, the purity of the IgGs was >95%.

Affinity ranking of the humanized antibodies was determined using a Surface Plasmon Resonance (SPR) biosensor, Biacore T200 (GE Healthcare). Anti-human Fc gamma specific antibody was immobilized onto the sensor chip using amine coupling method. Fifteen humanized antibodies secreted to the culture medium plus the parental antibody (murine MAb A6) were injected and captured by anti-human Fc antibody via Fc (capture phase) individually. After equilibration, Ag OX40-his was injected for 300 seconds (association phase) followed by the injection of running buffer for 600 s (dissociation phase). Responses of reference flow cell (flow cell 1) were subtracted from those of humanized antibodies flow cells during each cycle. The surface was regenerated before the injection of other humanized antibodies. The process was repeated until all antibodies are analyzed. The off-rates of humanized antibodies were obtained from fitting the experimental data locally to 1:1 interaction model using the Biacore 8K evaluation software. The antibodies were ranked by their dissociation rate constants (off-rates, $k_d$).

Humanized Ab REMD 277 (VH2-1/VL2-2), humanized Ab REMD 277.1 (VH2-1/VL2-1) and humanized Ab REMD 277.2 (VH2-1/VL5BM) were selected for further analysis. The amino acid sequences for the HCVR, LCVR, HC and LC of humanized Ab REMD 277, humanized Ab REMD 277.1, and humanized Ab REMD 277.2 are depicted in Table 5:

TABLE 5

| Humanized Antibody | HCVR | LCVR | HC | LC |
|---|---|---|---|---|
| REMD 277 (VH2-1/VL2-2) | SEQ ID NO: 61 | SEQ ID NO: 69 | SEQ ID NO: 91 | SEQ ID NO: 99 |
| REMD 277.1 (VH2-1/VL2-1) | SEQ ID NO: 61 | SEQ ID NO: 68 | SEQ ID NO: 91 | SEQ ID NO: 98 |
| REMD 277.2 (VH2-1/VL-5BM) | SEQ ID NO: 61 | SEQ ID NO: 67 | SEQ ID NO: 91 | SEQ ID NO: 97 |

The affinities of purified antibody binding to OX40-his was determined using a Surface Plasmon Resonance (SPR) biosensor, Biacore 8k. Antibodies were immobilized on the sensor chip through capture method. Antigen OX40-his was used as the analyte. The data of dissociation (kd) and association (ka) rate constants were obtained using Biacore 8k evaluation software. The equilibrium dissociation constants (KD) were calculated from the ratio of kd over ka. The results are summarized in Table 6.

TABLE 6

| Analyte | $k_a$ (1/Ms) | $k_d$ (1/s) | $K_D$ (M) | Rmax (RU) | Chi$^2$ (RU$^2$) |
|---|---|---|---|---|---|
| Chimeric | 9.42E+04 | 8.65E−04 | 9.18E−09 | 73.7 | 5.57E−01 |
| VH2-1 + VL2-1 | 6.14E+04 | 8.48E−04 | 1.38E−08 | 58.3 | 1.73E−01 |
| VH2-1 + VL-5BM | 2.00E+04 | 1.19E−04 | 5.94E−09 | 91.2 | 8.01E−02 |
| VH2-1 + VL2-2 | 2.82E+04 | 1.78E−04 | 6.30E−09 | 59.6 | 9.26E−02 |

Figure 1B:
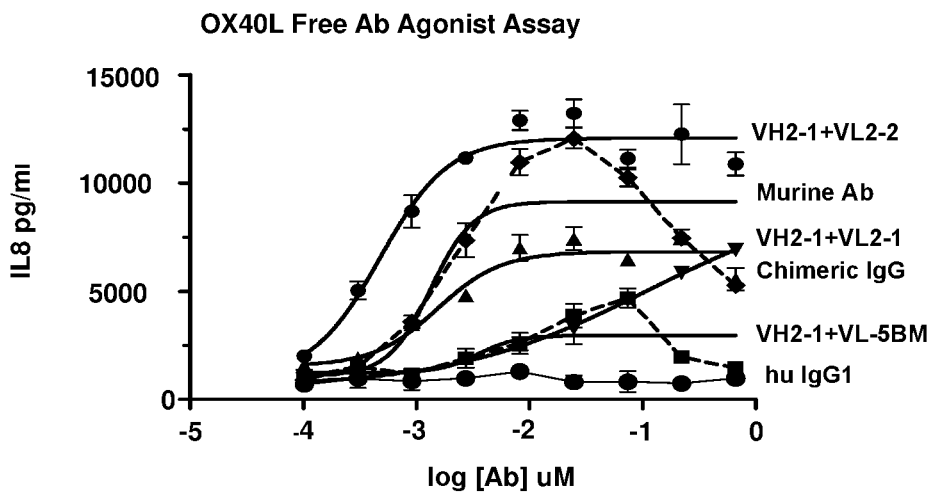
FIG. 1B is a line plot depicting agonist potencies of humanized OX40 Ab (VH2-1+VL2-1) (—●—), humanized OX40 Ab (VH2-1+VL-5BM) (—■—), humanized OX40 Ab (VH2-1+VL2-1) (—▲—), chimeric OX40 Ab (—▼—), murine OX40 MAb A6 (2G2E2D8) (—◆—) and human IgG1 (—●—). The potency of samples was measured by the concentration of interleukin 8 (IL-8) secreted by HT1080 OX40 stable cell lines.
Figure 1C:
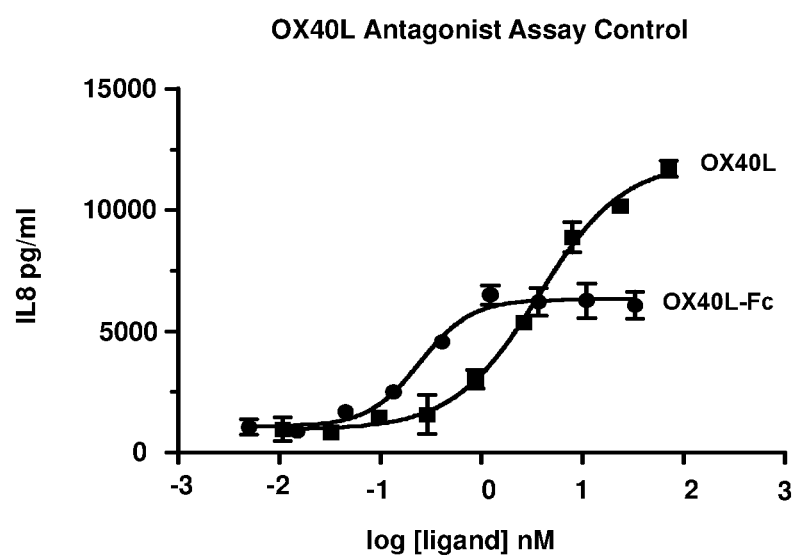
FIG. 1C is a line plot depicting the potency of OX40L antagonist assay controls OX40L-Fc (—●—) and OX40L (—■—) in an in vitro cell-based OX40 functional assay. The potency of samples was measured by the concentration of interleukin 8 (IL-8) secreted by HT1080 OX40 stable cell lines.
Figure 1D:
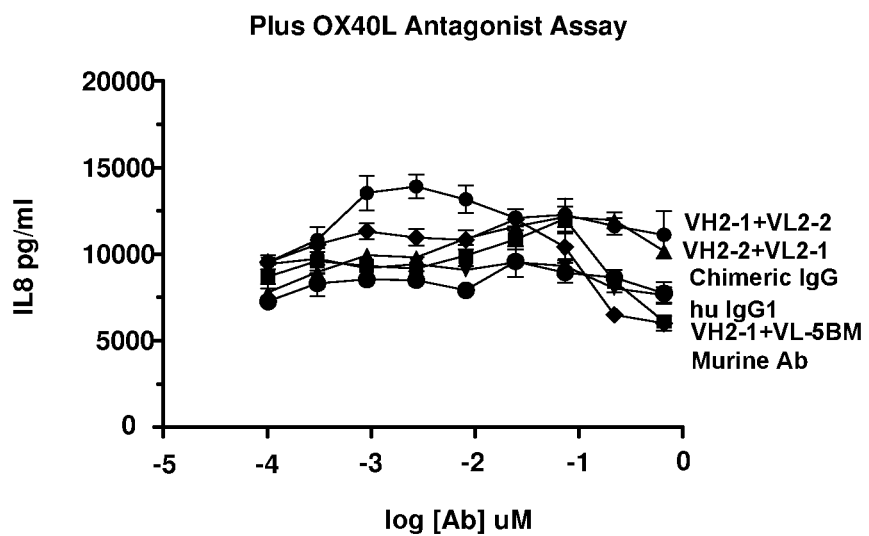
FIG. 1D is a line plot depicting antagonist potencies of humanized OX40 Ab (VH2-1+VL2-1) (—●—), humanized OX40 Ab (VH2-1+VL-5BM) (—■—), humanized OX40 Ab (VH2-1+VL2-1) (—▲—), chimeric OX40 Ab (—▼—), murine OX40 MAb A6 (2G2E2D8) (—◆—) and human IgG1 (—●—). The potency of samples was measured by the concentration of interleukin 8 (IL-8) secreted by HT1080 OX40 stable cell lines.

The in vitro cell-based OX40 functional assays of Example 2 were performed to evaluate the agonist potencies and antagonist potencies of humanized OX40 Ab (VH2-1+VL2-1), humanized OX40 Ab (VH2-1+VL-5BM), humanized OX40 Ab (VH2-1+VL2-1), chimeric OX40 Ab, murine OX40 MAb A6 (2G2E2D8) and human IgG1. The potency of samples was measured by the concentration of interleukin 8 (IL-8) secreted by HT1080 OX40 stable cell lines. The results are summarized in FIG. 1. A summary of the humanization of murine MAb A6 (2G2E2D8) is summarized in Table 7.

TABLE 7

| Antibody | Human Isotype | Epitope | HuOX40 ELISA Binding EC50 (pM) | Biacore KD (M) | HT1080 + OX40L Antagonist Assay IC50 (NM) |
|---|---|---|---|---|---|
| Murine A6 (2G2E2D8) | parental | 1 | 27.5 | | 1.341 |

TABLE 7-continued

| Antibody | Human Isotype | Epitope | HuOX40 ELISA Binding EC50 (pM) | Biacore KD (M) | HT1080 + OX40L Antagonist Assay IC50 (NM) |
|---|---|---|---|---|---|
| Chimeric | IgG4, κ | 1 | 28 | 9.18E−09 | 108.8 |
| VH2-1 + VL2-1 (REMD 277.1) | IgG4, κ | 1 | 960 | 1.38E−08 | 1.534 |
| VH2-1 + VL-5BM (REMD 277.2) | IgG4, κ | 1 | 3100 | 5.94E−09 | 3.515 |
| VH2-1 + VL2-2 (REMD 277) | IgG4, κ | 1 | 600 | 6.30E−09 | 0.479 |

The data described in Examples 1-4 establishes, among other things, that humanized Ab REMD 277 activates OX40 in an cell-based functional assay in the absence of OX40L (EC50 1.56 nM) and exhibits no OX40L/OX40 binding interference or OX40L inhibition in an OX40 functional assay.

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

SEQUENCE LISTINGS

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is the amino acid sequence of a human OX40 polypeptide.

SEQ ID NOs: 2-7 are the amino acid sequences of a heavy chain CDR1 in a monoclonal antibody which specifically binds OX40.

SEQ ID NOs: 8-12 are the amino acid sequences of a heavy chain CDR2 in a monoclonal antibody which specifically binds OX40.

SEQ ID NOs: 13-17 are the amino acid sequences of a heavy chain CDR3 in a monoclonal antibody which specifically binds OX40.

SEQ ID NOs: 18-21 are the amino acid sequences of a light chain CDR1 in a monoclonal antibody which specifically binds OX40.

SEQ ID NOs: 22-25 are the amino acid sequences of a light chain CDR2 in a monoclonal antibody which specifically binds OX40.

SEQ ID NOs: 26-28 are the amino acid sequences of a light chain CDR3 in a monoclonal antibody which specifically binds OX40.

SEQ ID NOs: 29, 31, 33, 35, 37 and 39 are nucleic acid sequences encoding a heavy chain variable region of monoclonal antibodies which specifically bind OX40.

SEQ ID NOs: 30, 32, 34, 36, 38 and 40 are amino acid sequences of a heavy chain variable region of monoclonal antibodies which specifically bind OX40.

SEQ ID NOs: 41, 43, 45, 47, 49 and 51 are nucleic acid sequences encoding a light chain variable region of monoclonal antibodies which specifically bind OX40.

SEQ ID NOs: 42, 44, 46, 48, 50 and 52 are amino acid sequences of a light chain variable region of monoclonal antibodies which specifically bind OX40.

SEQ ID NOs: 53 and 54 are the amino acid sequences of a light chain constant region of a monoclonal antibody which specifically binds OX40.

SEQ ID NO: 55 is the amino acid sequence of a heavy chain constant region of a monoclonal antibody which specifically binds OX40.

SEQ ID NOs: 56-62 are the amino acid sequences of a heavy chain variable region of humanized monoclonal antibodies which specifically binds OX40.

SEQ ID NOs: 63-69 are the amino acid sequence of a light chain variable region of humanized monoclonal antibodies which specifically binds OX40.

SEQ ID NOs: 70-76 are the nucleic acid sequences of a heavy chain variable region of humanized monoclonal antibodies which specifically binds OX40.

SEQ ID NOs: 77-83 are the nucleic acid sequence of a light chain variable region of humanized monoclonal antibodies which specifically binds OX40.

SEQ ID NO: 84 is the amino acid sequence of a heavy chain of a murine-human chimeric antibody which specifically binds OX40.

SEQ ID NO: 85 is the amino acid sequence of a light chain of a murine-human chimeric antibody which specifically binds OX40.

SEQ ID NOs: 86-92 are amino acid sequences of a heavy chain of humanized monoclonal antibodies which specifically binds OX40.

SEQ ID NOs: 93-99 are amino acid sequences of a light chain of humanized monoclonal antibodies which specifically binds OX40.

SEQ ID NOs: 100-106 are nucleic acid sequences of a heavy chain of humanized monoclonal antibodies which specifically binds OX40.

SEQ ID NOs: 107-113 are nucleic acid sequences of a light chain of humanized monoclonal antibodies which specifically binds OX40.

```
SEQUENCE LISTINGS
OX40 antigen amino acid sequence
                                                          SEQ ID NO: 1
LHCVGDTYPSNDRCCHECRPGNGMVSRCSRSQNTVCRPCGPGFYNDVVSSKPCKPCTWCN

LRSGSERKQLCTATQDTVCRCRAGTQPLDSYKPGVDCAPCPPGHFSPGDNQACKPWTNCTL
```

-continued

AGKHTLQPASNSSDAICEDRDPPATQPQETQGPPARPITVQPTEAWPRTSQGPSTRPVEVPG
GRAVAAILGLVLGLLGPLAILLALYLLRRDQRLPPDAHKPPGGGSFRTPIQEEQADAHSTLAKI

| | |
|---|---|
| Murine monoclonal antibody heavy chain CDR1 amino acid sequence DYAIH | SEQ ID NO: 2 |
| Murine monoclonal antibody heavy chain CDR1 amino acid sequence DYAMH | SEQ ID NO: 3 |
| Murine monoclonal antibody heavy chain CDR1 amino acid sequence SYGVH | SEQ ID NO: 4 |
| Murine monoclonal antibody heavy chain CDR1 amino acid sequence SYIMH | SEQ ID NO: 5 |
| Murine monoclonal antibody heavy chain CDR1 amino acid sequence ENYMN | SEQ ID NO: 6 |
| Murine monoclonal antibody heavy chain CDR1 amino acid sequence SYVMH | SEQ ID NO: 7 |
| Murine monoclonal antibody heavy chain CDR2 amino acid sequence VINTYYGDAAYNQKFQG | SEQ ID NO: 8 |
| Murine monoclonal antibody heavy chain CDR2 amino acid sequence VISTYYGDAAYNQKFKD | SEQ ID NO: 9 |
| Murine monoclonal antibody heavy chain CDR2 amino acid sequence VIWAGGSTDYNSALMS | SEQ ID NO: 10 |
| Murine monoclonal antibody heavy chain CDR2 amino acid sequence YINPYNDGTKYNEKFKG | SEQ ID NO: 11 |
| Murine monoclonal antibody heavy chain CDR2 amino acid sequence DINRNNGGTRYNQKFKG | SEQ ID NO: 12 |
| Murine monoclonal antibody heavy chain CDR3 amino acid sequence LDDFVY | SEQ ID NO: 13 |
| Murine monoclonal antibody heavy chain CDR3 amino acid sequence EEVWD | SEQ ID NO: 14 |
| Murine monoclonal antibody heavy chain CDR3 amino acid sequence YYGSSYTMDY | SEQ ID NO: 15 |
| Murine monoclonal antibody heavy chain CDR3 amino acid sequence TVVGYFDV | SEQ ID NO: 16 |
| Murine monoclonal antibody heavy chain CDR3 amino acid sequence YYGSNYAMDY | SEQ ID NO: 17 |
| Murine monoclonal antibody light chain CDR1 amino acid sequence KSSQSLLDSDGKTYLN | SEQ ID NO: 18 |
| Murine monoclonal antibody light chain CDR1 amino acid sequence RASQDISNYLN | SEQ ID NO: 19 |
| Murine monoclonal antibody light chain CDR1 amino acid sequence RASQDIRNYLN | SEQ ID NO: 20 |
| Murine monoclonal antibody light chain CDR1 amino acid sequence | |

-continued

Murine monoclonal antibody light chain CDR2 amino acid sequence
SEQ ID NO: 21
RSSQDISNYLN Murine monoclonal antibody light chain CDR2 amino acid sequence
SEQ ID NO: 22
LVSKLDS Murine monoclonal antibody light chain CDR2 amino acid sequence
SEQ ID NO: 23
YTSRLQS Murine monoclonal antibody light chain CDR2 amino acid sequence
SEQ ID NO: 24
YTSRLHS Murine monoclonal antibody light chain CDR2 amino acid sequence
SEQ ID NO: 25
YTSRLKS Murine monoclonal antibody light chain CDR3 amino acid sequence
SEQ ID NO: 26
WQGTHFPRT Murine monoclonal antibody light chain CDR3 amino acid sequence
SEQ ID NO: 27
QQGNTLPLT Murine monoclonal antibody light chain CDR3 amino acid sequence
SEQ ID NO: 28
QQGNTLPWT Murine monoclonal antibody heavy chain variable region nucleic acid sequence
SEQ ID NO: 29
atgggttggagctgtatcatcttctttctggtagcaacagctacaggtgtgcactcccaggtccagctgcaacagtctggggctgagctg gtgaggcctggggtctcagtgaagatttcctgcaaggggttctgactacacattcactgattatgctatacactgggaagcagagtcct gcaaagagtctagagtggattggagttattaatacttactatggtgatgctgcctacaaccagaagttccagggcaaggccacaatga ctgtagacaaatcctccagcgcagcctatatggaacttgccagactgacatctgaggattctgccatctattactgtgcaagattagacg attttgtttactggggccaagggactctggtcactgtctctgca Murine monoclonal heavy chain variable region amino acid sequence
SEQ ID NO: 30
MGWSCIIFFLVATATGVHSQVQLQQSGAELVRPGVSVKISCKGSDYTFTDYAIHWVKQSPAKSL

EWIGVINTYYGDAAYNQKFQGKATMTVDKSSSAAYMELARLTSEDSAIYYCARLDDFVYWGQG

TLVTVSA

Murine monoclonal antibody heavy chain variable region nucleic acid sequence
SEQ ID NO: 31
atgggttggagctgtatcatcttctttctggtagcaacagctacaggtgtgcactcccaggtccagctgcagcagtctggggctgagctg gtgaggcctggggtctcagtgaagatttactgcaaggggttctggctacacattcactgattacgctatgcactgggaagcagagtcat gcaaagagtctagagtggattggagttattagtacttactatggtgatgctgcttacaaccagaaattcaaggacaaggccacaatgac tgtagacaaatcctccagcacagcctatatggaacttgccagactgacatctgaggattctgccatctattactgtgcaagattagacga ttttgtttactggggccaagggactctggtcactgtctctgca Murine monoclonal heavy chain variable region amino acid sequence
SEQ ID NO: 32
MGWSCIIFFLVATATGVHSQVQLQQSGAELVRPGVSVKIYCKGSGYTFTDYAMHWVKQSHAK

SLEWIGVISTYYGDAAYNQKFKDKATMTVDKSSSTAYMELARLTSEDSAIYYCARLDDFVYWG

QGILVTVSA

Murine monoclonal antibody heavy chain variable region nucleic acid sequence
SEQ ID NO: 33
atggctgtcctggtgctgttcctctgcctggttgcatttccaagctgtgtcctgtcccaggtgcagctgaaggagtcaggacctggcctggt ggcgccctcacagagcctgtccatcacctgcactgtctctggttttcattaagcagctatggtgtacactgggttcgccagcctccagg aaagggtctggaatggctgggagtaatatgggctggtggaagcacagattataattcggctctcatgtccagactgagcatcagcaaa

```
gacaactccaagagccaagttgtcttaaaaatgaacagcctgcaaactgatgacacagccatgtactactgtgccagagaagaggt ctgggactggggccaagggactctggtcactgtctctgca
```

Murine monoclonal heavy chain variable region amino acid sequence
SEQ ID NO: 34

```
MAVLVLFLCLVAFPSCVLSQVQLKESGPGLVAPSQSLSITCTVSGFSLSSYGVHWVRQPPGKG

LEWLGVIWAGGSTDYNSALMSRLSISKDNSKSQVVLKMNSLQTDDTAMYYCAREEVWDWGQ

GTLVTVSA
```

Murine monoclonal antibody heavy chain variable region nucleic acid sequence
SEQ ID NO: 35

```
atggaatggagttggatatttctcttctcctgtcaggaactgcaggtgtccactctgaggtccagctgcagcagtctggacctgagctggt aaagcctggggcttcagtgaagatgtcctgcaaggcttctggatacacattcactagctatattatgcactgggtgaagcagaagcctg ggcagggccttgagtggattggatatattaatccttacaatgatggtactaagtacaatgaaaagttcaaaggcaaggccacactgact tcagacaaatcctccagcacagcctacatggagctcagcagcctgacctctgaggactctgcggtctattactgtgcaaattactacgg tagtagctatactatggactactgggtcaaggaacctcagtcaccgtctcctca
```

Murine monoclonal heavy chain variable region amino acid sequence
SEQ ID NO: 36

```
MEWSWIFLFLLSGTAGVHSEVQLQQSGPELVKPGASVKMSCKASGYTFTSYIMHWVKQKPGQ

GLEWIGYINPYNDGTKYNEKFKGKATLTSDKSSSTAYMELSSLTSEDSAVYYCANYYGSSYTM

DYWGQGTSVTVSS
```

Murine monoclonal antibody heavy chain variable region nucleic acid sequence
SEQ ID NO: 37

```
atgggatggagctggatctttctcttctcctgtcaggaactgcaggtgtcctctctgaggtccagctgcaacaatctggacctgagctggt gaagcctggggcttcagtgaagatatcctgtaaggcttctggatacacgttcactgaaaactacatgaactgggtgaagcagagccat ggaaagagccttgagtggattggagatattaatcgtaataatggtggtactagatacaaccagaagttcaagggcaaggccacattg actgtagacaagtcctccagcacagactacatggagctccgcagcctgacatctgaggactctgcagtctattactgtgggggcacgg tagtagggtacttcgatgtctggggcacagggaccacggtcaccgtctcctca
```

Murine monoclonal heavy chain variable region amino acid sequence
SEQ ID NO: 38

```
MGWSWIFLFLLSGTAGVLSEVQLQQSGPELVKPGASVKISCKASGYTFTENYMNWVKQSHGK

SLEWIGDINRNNGGTRYNQKFKGKATLTVDKSSSTDYMELRSLTSEDSAVYYCGGTVVGYFDV

WGTGTTVTVSS
```

Murine monoclonal antibody heavy chain variable region nucleic acid sequence
SEQ ID NO: 39

```
atggaatggagttggatatttctcttctcctgtcaggaactgcaggtgtccactctgaggtccagctgcagcagtctggacctgagctggt aaagcctggggcttcagtgaagatgtcctgcaaggcttctggatacacattcactagctatgttatgcactgggtgaagcagaagcctg ggcagggccttgagtggattggatatattaatccttacaatgatggtactaagtacaatgagaagttcaaaggcaaggccacactgact tcagacaaatcctccagcacagcctacatggagctcagcagcctgacctctgaggactctgcggtctattactgtgcaaattactacgg tagtaactatgctatggactactgggtcaaggaacctcagtcaccgtctcctca
```

Murine monoclonal heavy chain variable region amino acid sequence
SEQ ID NO: 40

```
MEWSWIFLFLLSGTAGVHSEVQLQQSGPELVKPGASVKMSCKASGYTFTSYVMHWVKQKPG

QGLEWIGYINPYNDGTKYNEKFKGKATLTSDKSSSTAYMELSSLTSEDSAVYYCANYYGSNYA

MDYWGQGTSVTVSS
```

Murine monoclonal antibody light chain variable region nucleic acid sequence
SEQ ID NO: 41

```
atgatgagtcctgcccagttcctgtttctgttagtgctctgattcgggaaaccaacggtgatgttgtgatgacccagactccactcactttg tcggttaccattggtcaaccggcctccatctcttgcaagtcaagtcagagcctcttagatagtgatggaaagacatatttgaattggttgtt
```

```
acagaggccaggccagtctccaaagcgcctaatctatctggtgtctaaactggactctggagtccctgacaggttcactggcagtgga tcagggacagatttcacactgaaaatcagcagagtggaggctgaggatttgggagtttattattgctggcaaggtacacattttcctcgg acgttcggtggaggcaccaagctggaaatcaaa
```

Murine monoclonal light chain variable region amino acid sequence  
SEQ ID NO: 42

```
MMSPAQFLFLLVLWIRETNGDVVMTQTPLTLSVTIGQPASISCKSSQSLLDSDGKTYLNWLLQR

PGQSPKRLIYLVSKLDSGVPDRFTGSGSGTDFTLKISRVEAEDLGVYYCWQGTHFPRTFGGGT

KLEIK
```

Murine monoclonal antibody light chain variable region nucleic acid sequence  
SEQ ID NO: 43

```
atgatgagtcctgcccagttcctgtttctgttagtgctctggattcgggaaatcaacggtgatgttgtgatgacccagactccactcactttgt cggttaccattggacaaccagcctccatctcttgcaagtcaagtcagagcctcttagatagtgatggaaagacatatttgaattggttgtt acagaggccaggccagtctccaaagcgcctaatctatctggtgtctaaactggactctggagtccctgacaggttcactggcagtgga tcagggacagatttcacactgaaaatcagcagagtggaggctgaggatttgggagtttattattgctggcaaggtacacattttcctcgg acgttcggtggaggcaccaagctggaaatcaaa
```

Murine monoclonal light chain variable region amino acid sequence  
SEQ ID NO: 44

```
MMSPAQFLFLLVLWIREINGDVVMTQTPLTLSVTIGQPASISCKSSQSLLDSDGKTYLNWLLQR

PGQSPKRLIYLVSKLDSGVPDRFTGSGSGTDFTLKISRVEAEDLGVYYCWQGTHFPRTFGGGT

KLEIK
```

Murine monoclonal antibody light chain variable region nucleic acid sequence  
SEQ ID NO: 45

```
atgatgtcctctgctcagttccttggtctcctgttgctctgttttcaagtcctaggtatcagatgtgatatccagatgacacagactacatcctc cctgtctgcctctctgggagacagagtcaccatcagttgcagggcaagtcaggacattagcaattatttaaaactggtatcagcagaaac cagatggaactgttaaaactcctgatctactacacatcaagattacagtcaggagtcccatcaaggttcagtggcagtgggtctggaaca gattattctctcaccattagcaacctggagcaagaagatattgccacttacttttgccaacagggtaatacgcttcctctcacgttcggtgct gggaccaagctggagctgaaa
```

Murine monoclonal light chain variable region amino acid sequence  
SEQ ID NO: 46

```
MMSSAQFLGLLLLCFQVLGIRCDIQMTQTTSSLSASLGDRVTISCRASQDISNYLNWYQQKPDG

TVKLLIYYTSRLQSGVPSRFSGSGSGTDYSLTISNLEQEDIATYFCQQGNTLPLTFGAGTKLELK
```

Murine monoclonal antibody light chain variable region nucleic acid sequence  
SEQ ID NO: 47

```
atgatgtcctctgctcagttccttggtctcctgttgctctgttttcaaggtaccagatgtgatatccagatgacacagactacatcctccctgtc tgcctctctgggagacagagtcaccatcagttgcagggcaagtcaggacattagaaatttatttaaactggtatcagcagaaaccagat ggaagtgttaaactcctgatctactacacatcaagattacactcaggagtcccatcaaggttcagtggcagtgggtctggaacagatta ttctctcaccattagcaacctggagcaagaagatattgccacttacttttgccaacagggtaatacgcttccgtggacgttcggtggagg caccaagctggaaatcaaa
```

Murine monoclonal light chain variable region amino acid sequence  
SEQ ID NO: 48

```
MMSSAQFLGLLLLCFQGTRCDIQMTQTTSSLSASLGDRVTISCRASQDIRNYLNWYQQKPDGS

VKLLIYYTSRLHSGVPSRFSGSGSGTDYSLTISNLEQEDIATYFCQQGNTLPWTFGGGTKLEIK
```

Murine monoclonal antibody light chain variable region nucleic acid sequence  
SEQ ID NO: 49

```
atgatgtcctctgctcagttccttggtctcctgttgctctgttttcaaggtaccagatgtgatatccagatgacacagattataacctccctgtct gcctctctgggagacagagtcaccatcagttgcaggtcaagtcaggacattagtaattatttaaattggtatcagcagaaaccagatgg aactgttaaactcctgatctactacacatcaagattaaaatcaggagtcccatcaaggttcagtggcagtgggtctggaacagattattc tctcaccattagcaacctggagcaagaagatattgccacttacttttgccaacagggtaatacgcttccgtggacgttcggtggaggca
``` ccaagctggaaatcaaa

Murine monoclonal light chain variable region amino acid sequence  SEQ ID NO: 50
MMSSAQFLGLLLLCFQGTRCDIQMTQIITSLSASLGDRVTISCRSSQDISNYLNWYQQKPDGTV
KLLIYYTSRLKSGVPSRFSGSGSGTDYSLTISNLEQEDIATYFCQQGNTLPWTFGGGTKLEIK Murine monoclonal antibody light chain variable region nucleic acid sequence  SEQ ID NO: 51
atgatgtcctctgctcagttccttggtctcctgttgctctgttttcaaggtaccagatgtgatatccagatgacacagactacatcctccctgtc
tgcctctctgggagacagagtcaccatcagttgcagggcaagtcaggacattaggaattatttaaactggtatcagcagaaaccaga
cggaactgttaaactcctgatctactacacatcaagattacactcaggagtcccatcaaggttcagtggcagtgggtctggaacagatt
attctctcaccatcagcaacctggagcaagaagatattgccacttacttttgccaacagggtaatacgcttccgtggacgttcggtggag
gcaccaagctggaaatcaaa Murine monoclonal light chain variable region amino acid sequence  SEQ ID NO: 52
MMSSAQFLGLLLLCFQGTRCDIQMTQTTSSLSASLGDRVTISCRASQDIRNYLNWYQQKPDGT
VKLLIYYTSRLHSGVPSRFSGSGSGTDYSLTISNLEQEDIATYFCQQGNTLPWTFGGGTKLEIK Light chain constant region amino acid sequence  SEQ ID NO: 53
TVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC Light chain constant region amino acid sequence  SEQ ID NO: 54
QPKAAPSVTLFPPSSEELQANKATLVCLISDFYPGAVTVAWKADSSPVKAGVETTTPSKQSNN
KYAASSYLSLTPEQWKSHRSYSCQVTHEGSTVEKTVAPTECS Heavy chain constant region amino acid sequence  SEQ ID NO: 55
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPGK Humanized heavy chain variable region amino acid sequence  SEQ ID NO: 56
QVQLVQSGAEVKKPGASVKVSCKASGYTFTSYVMHWVRQAPGQRLEWMGYINPYNDGTKYN
EKFKGRVTITRDTSASTAYMELSSLRSEDTAVYYCARYYGSNYAMDYWGQGTLVTVSS Humanized heavy chain variable region amino acid sequence  SEQ ID NO: 57
QVQLVQSGAEVKKPGASVKVSCKASGYTFTSYVMHWVRQAPGQRLEWIGYINPYNDGTKYNE
KFKGRVTITSDTSASTAYMELSSLRSEDTAVYYCANYYGSNYAMDYWGQGTLVTVSS Humanized heavy chain variable region amino acid sequence  SEQ ID NO: 58
QVQLVQSGAEVKKPGASVKMSCKASGYTFTSYVMHWVKQAPGQRLEWIGYINPYNDGTKYN
EKFKGRVTITSDTSASTAYMELSSLRSEDTAVYYCANYYGSNYAMDYWGQGTLVTVSS Humanized heavy chain variable region amino acid sequence  SEQ ID NO: 59
QVQLVQSGAEVKKPGASVKMSCKASGYTFTSYVMHWVKQAPGQRLEWIGYINPYNDGTKYN
EKFKGRATLTSDTSASTAYMELSSLRSEDTAVYYCANYYGSNYAMDYWGQGTLVTVSS Humanized heavy chain variable region amino acid sequence  SEQ ID NO: 60
QVQLVQSGAEVKKPGASVKVSCKASGYTFTSYVMHWVKQAPGQRLEWIGYINPYNDGTKYNE
KFKGKATLTSDTSASTAYMELSSLRSEDTAVYYCANYYGSNYAMDYWGQGTLVTVSS -continued

| | |
|---|---|
| Humanized heavy chain variable region amino acid sequence<br>EVQLVQSGAEVKKPGESLKISCKGSGYTFTSYVMHWVRQMPGKGLEWMGYINPYNDGTKYN<br>EKFKGQVTISADKSISTAYLQWSSLKASDTAMYYCARYYGSNYAMDYWGQGTMVTVSS | SEQ ID NO: 61 |
| Humanized heavy chain variable region amino acid sequence<br>EVQLVQSGAEVKKPGESVKMSCKGSGYTFTSYVMHWVKQMPGKGLEWIGYINPYNDGTKYN<br>EKFKGQATLSSDKSISTAYMQLSSLKASDTAMYYCANYYGSNYAMDYWGQGTMVTVSS | SEQ ID NO: 62 |
| Humanized light chain variable region amino acid sequence<br>QMTQSPSSLSASVGDRVTITCRASQDIRNYLNWYQQKPGKAPKLLIYYTSRLHSGVPSRFSGS<br>GSGTDFTFTISSLQPEDIATYYCQQGNTLPWTFGGGTKLEIK | SEQ ID NO: 63 |
| Humanized light chain variable region amino acid sequence<br>QMTQSPSSLSASVGDRVTITCRASQDIRNYLNWYQQKPGKAVKLLIYYTSRLHSGVPSRFSGS<br>GSGTDFTFTISSLQPEDIATYFCQQGNTLPWTFGGGTKLEIK | SEQ ID NO: 64 |
| Humanized light chain variable region amino acid sequence<br>QMTQSPSSLSASVGDRVTITCRASQDIRNYLNWYQQKPGGAVKLLIYYTSRLHSGVPSRFSGS<br>GSGTDFTLTISSLQPEDIATYFCQQGNTLPWTFGGGTKLEIK | SEQ ID NO: 65 |
| Humanized light chain variable region amino acid sequence<br>DIQMTQSPSSLSASVGDRVTITCRASQDIRNYLNWYQQKPGGAVKLLIYYTSRLHSGVPSRFSG<br>SGSGTDYTLTISSLQPEDIATYFCQQGNTLPWTFGGGTKLEIK | SEQ ID NO: 66 |
| Humanized light chain variable region amino acid sequence<br>QMTQSPSSLSASVGDRVTISCRASQDIRNYLNWYQQKPGKTVKLLIYYTSRLHSGVPSRFSGS<br>GSGTDYTFTISSLQPEDIATYFCQQGNTLPWTFGGGTKLEIK | SEQ ID NO: 67 |
| Humanized light chain variable region amino acid sequence<br>EIVLTQSPATLSLSPGERATLSCRASQDIRNYLNWYQQKPGQAPRLLIYYTSRLHSGIPARFSGS<br>GSGTDFTLTISSLEPEDFAVYYCQQGNTLPWTFGQGTKVEIK | SEQ ID NO: 68 |
| Humanized light chain variable region amino acid sequence<br>EIVMTQSPATLSASPGERVTLSCRASQDIRNYLNWYQQKPGGAVRLLIYYTSRLHSGVPARFS<br>GSGSGTDYTLTISSLEPEDYAVYFCQQGNTLPWTFGQGTKVEIK | SEQ ID NO: 69 |
| Humanized heavy chain variable region nucleic acid sequence<br>caggtgcagctggtccagagcggagcagaggtgaagaaaccggagcaagcgtgaaggtgtcctgtaaggcaagcggctatact<br>ttcacaagctacgtgatgcactgggtcaggcaggctccaggacagcgcctggagtggatgggatacatcaaccccttacaacgacgg<br>aactaagtacaacgaaaagttcaaaggccgggtgaccattacaagagatacttctgccagtaccgcttacatggagctgagctccct<br>gcgatctgaagacaccgcagtctactattgcgccagatattatgggagcaactacgctatggattattggggcaggggactctggtc<br>actgtctcttca | SEQ ID NO: 70 |
| Humanized heavy chain variable region nucleic acid sequence<br>caggtgcagctggtgcagtctggggccgaagtgaagaaaccggagcatcagtcaaagtcagttgtaaggcatcaggctatacatt<br>cacatcttacgtgatgcactgggtccggcaggctccaggacagagactggagtggatcgggtacattaaccccttacaacgacggaa<br>ctaagtacaacgaaaagttcaaaggcagggtgaccatcacatcagatacttctgccagtaccgcttacatggagctgagctccctgc<br>ggagcgaagacaccgcagtctactattgcgccaattattatggctcaaactacgctatggactattggggcaggggacactggtgac<br>cgtctcctca | SEQ ID NO: 71 |
| Humanized heavy chain variable region nucleic acid sequence | SEQ ID NO: 72 |

-continued aggtgcagctggtccagagcggagcagaagtcaagaaacccggcgcaagtgtgaagatgagttgtaaggcaagcggctatacatt
cacatcttacgtgatgcactgggtcaagcaggctccaggacagaggctggagtggatcgggtacatcaacccttacaacgacgaa
ctaagtacaacgaaaagttcaaaggccgggtgaccatcacatcagatacttctgccagtaccgcttacatggagctgagctccctga
gaagcgaagacaccgcagtctactattgcgccaattattatggctctaactatgctatggattattgggggcagggcactctggtcaccg
tgtcaagc Humanized heavy chain variable region nucleic acid sequence

SEQ ID NO: 73 aggtgcagctggtccagagcggagcagaggtgaagaaacccggagcatcagtcaaaatgtcctgtaaggcaagcggctatactttt
cacatcttacgtgatgcactgggtcaagcaggctccaggacagaggctggagtggatcgggtacatcaacccttacaacgacgaa
ctaagtacaacgaaaagttcaaaggccgggccaccctgacatcagatacttctgccagtaccgcttacatggagctgagctccctga
gaagcgaagacaccgcagtgtactattgcgccaattattatgggtcaaactacgctatggactattgggggcagggcactctggtcact
gtcagcagc Humanized heavy chain variable region nucleic acid sequence

SEQ ID NO: 74 aggtgcagctggtccagagcggagcagaggtgaagaaacccggagcatcagtcaaaatgtcctgtaaggcaagcggctatactttt
cacatcttacgtgatgcactgggtcaagcaggctccaggacagaggctggagtggatcgggtacatcaacccttacaacgacggaa
ctaagtacaacgaaaagttcaaaggccgggccaccctgacatcagatacttctgccagtaccgcttacatggagctgagctccctga
gaagcgaagacaccgcagtgtactattgcgccaattattatgggtcaaactacgctatggactattgggggcagggcactctggtcact
gtcagcagc Humanized heavy chain variable region nucleic acid sequence

SEQ ID NO: 75 gaagtgcagctggtgcagagcggggcagaagtgaagaagcctggggaaagcctgaagattagttgtaaagggagcggatataca
ttcacttcttacgtgatgcactgggtccggcagatgccaggcaagggactggagtggatgggatacatcaacccttataatgacggca
ccaaatataacgaaaagttcaaagggcaggtgaccatctcagcagacaagtctattagtacagcctacctgcagtggagctccctga
aagccagcgacacagctatgtactattgcgctagatattatggctcaaactacgctatggactactggggacaggggactatggtcac
cgtctcaagc Humanized heavy chain variable region nucleic acid sequence

SEQ ID NO: 76 gaggtccagctggtgcagagcggagcagaggtcaagaagcccggcgaatcagtgaagatgtcctgtaagggaagcggatatactt
tcacttcctacgtgatgcactgggtcaagcagatgcccggcaaagggctggagtggatcggatacattaacccttataatgacggcac
caagtataacgaaaagttcaaagggcaggcaaccctgagctccgataagtcaatcagcacagcctacatgcagctgtctagtctga
aagccagtgacacagctatgtactattgcgctaattattatgggtcaaactacgcaatggattactgggggcagggaacaatggtcact
gtctcttca Humanized light chain variable region nucleic acid sequence

SEQ ID NO: 77 gacattcagatgacccagagcccttccagcctgagtgccagcgtcggagatagagtgacaattacttgccgcgccagccaggacatt
aggaactacctgaattggtatcagcagaagcccggcaaagcccctaagctgctgatctactatacaagccggctgcactccggggtg
ccaagtagattctctggcagtgggtcaggaactgacttcaccttacaatcagctccctgcagcccgaggatattgctacctactattgtc
agcagggaaatacactgccttggaccttcggcggggggactaaactggaaatcaaa Humanized light chain variable region nucleic acid sequence

SEQ ID NO: 78 gacattcagatgacccagagcccttccagcctgagcgccagcgtcggagacagagtgactattacttgtagagccagccaggacatt
aggaactacctgaattggtatcagcagaagcccggcaaagccgtgaagctgctgatctactatacaagccggctgcactccggggt
ccctagtagattctctggcagtgggtcaggaactgacttcacctttacaatcagctccctgcagcccgaggatattgctacctacttttgtc
agcagggaaatacactgccttggaccttcggagggggactaaactggaaatcaaa Humanized light chain variable region nucleic acid sequence

SEQ ID NO: 79 gatattcagatgacccagtcaccttccagtctgagtgccagcgtcggggatagagtcaccattacttgccgcgccagccaggacatta -continued

```
ggaactacctgaattggtatcagcagaagcccggcggggccgtgaaactgctgatctactatacaagccggctgcactccggcgtcc
ctagtagattctctggaagtggctcagggactgactttaccctgacaatcagctccctgcagcccgaggatattgctacctacttctgtca
gcagggaaatacactgccttggaccttcggagggggactaaactggaaatcaaa
```

Humanized light chain variable region nucleic acid sequence
SEQ ID NO: 80

```
gacattcagatgacccagagccccagcagcctgagcgccagcgtcggagatagagtgaccattacttgtagagccagccaggaca
ttaggaactacctgaattggtatcagcagaagcccggcggggccgtgaaactgctgatctactatacaagccggctgcactccggcg
tccctagtagattctctggaagtggctcagggactgactacaccctgacaatcagctccctgcagcccgaggatattgctacctattttgt
cagcagggaaatactctgccttggaccttcggcggagggactaaactggaaatcaaa
```

Humanized light chain variable region nucleic acid sequence
SEQ ID NO: 81

```
gacattcagatgacccagagccttccagcctgagtgcttccgtcggggatagagtgacaattagttgcagagccagccaggacatt
aggaactacctgaattggtatcagcagaagcccggcaaaactgtgaagctgctgatctactataccagccggctgcactccggggtc
cctagtagattctctggcagtgggtcaggaacagactacacctttacaatcagctccctgcagcccgaggatattgccacctatttctgtc
agcagggaaatactctgccttggaccttcggcggcggaactaaactggaaatcaaa
```

Humanized light chain variable region nucleic acid sequence
SEQ ID NO: 82

```
gaaatcgtgctgacccagtcccccgccacactgagtctgtccccggagaaagagccaccctgagctgtagggcaagccaggata
ttcggaactacctgaattggtatcagcagaagccaggacaggcacctcgactgctgatctactatactagcagactgcactctgggatt
ccagctaggttctctggcagtgggtcaggaaccgactttaccctgacaatcagctccctggagcccgaagatttcgccgtgtactattgc
cagcaggggaatactctgccttggaccttcggccaggggactaaagtggaaatcaaa
```

Humanized light chain variable region nucleic acid sequence
SEQ ID NO: 83

```
gaaatcgtgatgacccagagcccagccacactgtccgccagcccaggcgagagagtcacactgtcttgccgagccagccaggat
attcggaactacctgaattggtatcagcagaagccaggaggagccgtgcggctgctgatctactatactagcagactgcactctggcg
tccctgctaggttctctggaagtggctcagggaccgactacaccctgacaattagctccctggagcccgaagattacgccgtgtattttg
ccagcagggaaatactctgccttggacattcggcaggggactaaagtggaaatcaaa
```

Heavy chain amino acid sequence of a murine-human chimeric antibody
SEQ ID NO: 84

```
MGWSWILLFLLSVTAGVHSEVQLQQSGPELVKPGASVKMSCKASGYTFTSYVMHWVKQKPG
QGLEWIGYINPYNDGTKYNEKFKGKATLTSDKSSSTAYMELSSLTSEDSAVYYCANYYGSNYA
MDYWGQGTSVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

Light chain amino acid sequence of a murine-human chimeric antibody
SEQ ID NO: 85

```
MGWSWILLFLLSVTAGVHSDIQMTQTTSSLSASLGDRVTISCRASQDIRNYLNWYQQKPDGTV
KLLIYYTSRLHSGVPSRFSGSGSGTDYSLTISNLEQEDIATYFCQQGNTLPWTFGGGTKLEIKRT
VAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC
```

Humanized heavy chain amino acid sequence - 19 aa leader sequence
SEQ ID NO: 86

```
MGWSWILLFLLSVTAGVHSQVQLVQSGAEVKKPGASVKVSCKASGYTFTSYVMHWVRQAPG
QRLEWMGYINPYNDGTKYNEKFKGRVTITRDTSASTAYMELSSLRSEDTAVYYCARYYGSNYA
```

-continued

```
MDYWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

| Humanized heavy chain amino acid sequence - 19 aa leader sequence | SEQ ID NO: 87 |
|---|---|

```
MGWSWILLFLLSVTAGVHSQVQLVQSGAEVKKPGASVKVSCKASGYTFTSYVMHWVRQAPG

QRLEWIGYINPYNDGTKYNEKFKGRVTITSDTSASTAYMELSSLRSEDTAVYYCANYYGSNYA

MDYWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

| Humanized heavy chain amino acid sequence - 19 aa leader sequence | SEQ ID NO: 88 |
|---|---|

```
MGWSWILLFLLSVTAGVHSQVQLVQSGAEVKKPGASVKMSCKASGYTFTSYVMHWVKQAPG

QRLEWIGYINPYNDGTKYNEKFKGRVTITSDTSASTAYMELSSLRSEDTAVYYCANYYGSNYA

MDYWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

| Humanized heavy chain amino acid sequence - 19 aa leader sequence | SEQ ID NO: 89 |
|---|---|

```
MGWSWILLFLLSVTAGVHSQVQLVQSGAEVKKPGASVKMSCKASGYTFTSYVMHWVKQAPG

QRLEWIGYINPYNDGTKYNEKFKGRATLTSDTSASTAYMELSSLRSEDTAVYYCANYYGSNYA

MDYWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSRW

QQGNVFSCSVMHEALHNHYTQKSLSLSPGK
```

| Humanized heavy chain amino acid sequence - 19 aa leader sequence | SEQ ID NO: 90 |
|---|---|

```
MGWSWILLFLLSVTAGVHSQVQLVQSGAEVKKPGASVKVSCKASGYTFTSYVMHWVKQAPG

QRLEWIGYINPYNDGTKYNEKFKGKATLTSDTSASTAYMELSSLRSEDTAVYYCANYYGSNYA

MDYWGQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSRW
```

QQGNVFSCSVMHEALHNHYTQKSLSLSPGK

Humanized heavy chain amino acid sequence - 19 aa leader sequence SEQ ID NO: 91

MGWSWILLFLLSVTAGVHSEVQLVQSGAEVKKPGESLKISCKGSGYTFTSYVMHWVRQMPGK
GLEWMGYINPYNDGTKYNEKFKGQVTISADKSISTAYLQWSSLKASDTAMYYCARYYGSNYA
MDYWGQGTMVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRW
QQGNVFSCSVMHEALHNHYTQKSLSLSPGK

Humanized heavy chain amino acid sequence - 19 aa leader sequence SEQ ID NO: 92

MGWSWILLFLLSVTAGVHSEVQLVQSGAEVKKPGESVKMSCKGSGYTFTSYVMHWVKQMPG
KGLEWIGYINPYNDGTKYNEKFKGQATLSSDKSISTAYMQLSSLKASDTAMYYCANYYGSNYA
MDYWGQGTMVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSKLTVDKSRW
QQGNVFSCSVMHEALHNHYTQKSLSLSPGK

Humanized light chain amino acid sequence - 19 aa leader sequence SEQ ID NO: 93

MGWSWILLFLLSVTAGVHSDIQMTQSPSSLSASVGDRVTITCRASQDIRNYLNWYQQKPGKAP
KLLIYYTSRLHSGVPSRFSGSGSGTDFTFTISSLQPEDIATYYCQQGNTLPWTFGGGTKLEIKRT
VAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

Humanized light chain amino acid sequence - 19 aa leader sequence SEQ ID NO: 94

MGWSWILLFLLSVTAGVHSDIQMTQSPSSLSASVGDRVTITCRASQDIRNYLNWYQQKPGKAV
KLLIYYTSRLHSGVPSRFSGSGSGTDFTFTISSLQPEDIATYFCQQGNTLPWTFGGGTKLEIKRT
VAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

Humanized light chain amino acid sequence - 19 aa leader sequence SEQ ID NO: 95

MGWSWILLFLLSVTAGVHSDIQMTQSPSSLSASVGDRVTITCRASQDIRNYLNWYQQKPGGAV
KLLIYYTSRLHSGVPSRFSGSGSGTDFTLTISSLQPEDIATYFCQQGNTLPWTFGGGTKLEIKRT
VAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

Humanized light chain amino acid sequence - 19 aa leader sequence SEQ ID NO: 96

MGWSWILLFLLSVTAGVHSDIQMTQSPSSLSASVGDRVTITCRASQDIRNYLNWYQQKPGGAV
KLLIYYTSRLHSGVPSRFSGSGSGTDYTLTISSLQPEDIATYFCQQGNTLPWTFGGGTKLEIKRT
VAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

Humanized light chain amino acid sequence - 19 aa leader sequence SEQ ID NO: 97

```
                                                                                                  SEQ ID NO: 98
MGWSWILLFLLSVTAGVHSDIQMTQSPSSLSASVGDRVTISCRASQDIRNYLNWYQQKPGKTV

KLLIYYTSRLHSGVPSRFSGSGSGTDYTFTISSLQPEDIATYFCQQGNTLPWTFGGGTKLEIKRT

VAAPSVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC
```

Humanized light chain amino acid sequence - 19 aa leader sequence

SEQ ID NO: 98

```
MGWSWILLFLLSVTAGVHSEIVLIQSPATLSLSPGERATLSCRASQDIRNYLNWYQQKPGQAP

RLLIYYTSRLHSGIPARFSGSGSGTDFTLTISSLEPEDFAVYYCQQGNTLPWTFGQGTKVEIKRT

VAAPSVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC
```

Humanized light chain amino acid sequence - 19 aa leader sequence

SEQ ID NO: 99

```
MGWSWILLFLLSVTAGVHSEIVMTQSPATLSASPGERVTLSCRASQDIRNYLNWYQQKPGGAV

RLLIYYTSRLHSGVPARFSGSGSGTDYTLTISSLEPEDYAVYFCQQGNTLPWTFGQGTKVEIKR

TVAAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC
```

Humanized heavy chain nucleic acid sequence - 19 aa leader sequence

SEQ ID NO: 100

```
atgggctggagctggatcctgctgttcctcctgagcgtgacagcaggagtgcacagccaggtgcagctggtccagagcggagcaga ggtgaagaaacccggagcaagcgtgaaggtgtcctgtaaggcaagcggctatactttcacaagctacgtgatgcactgggtcaggc aggctccaggacagcgcctggagtggatgggatacatcaaccctracaacgacggaactaagtacaacgaaaagttcaaaggcc gggtgaccattacaagagatacttctgccagtaccgcttacatggagctgagctccctgcgatctgaagacaccgcagtctactattgc gccagatattatgggagcaactacgctatggattattgggggcaggggactctggtcactgtctcttcagctagcaccaagggcccatc ggtcttccccctggcaccctcctccaagagcacctctgggggcacagcggccctgggctgcctggtcaaggactacttccccgaacc ggtgacggtgtcgtggaactcaggcgccctgaccagcggcgtgcacaccttcccggctgtcctacagtcctcaggactctactccctc agcagcgtggtgaccgtgccctccagcagcttgggcacccagacctacatctgcaacgtgaatcacaagcccagcaacaccaagg tggacaagaaagttgagcccaaatcttgtgacaaaactcacacatgcccaccgtgcccagcacctgaactcctggggggaccgtca gtcttcctcttccccccaaaacccaaggacaccctcatgatctcccggacccctgaggtcacatgcgtggtggtggacgtgagccacg aagaccctgaggtcaagttcaactggtacgtggacggcgtggaggtgcataatgccaagacaaagccgcgggaggagcagtaca acagcacgtaccgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacaccctgccccc atcccgggatgagctgaccaagaaccaggtcagcctgacctgcctggtcaaaggcttctatcccagcgacatcgccgtggagtggg agagcaatgggcagccggagaacaactacaagaccacgcctcccgtgctggactccgacggctccttcttcctctacagcaagctc accgtggacaagagcaggtggcagcaggggaacgtcttctcatgctccgtgatgcatgaggctctgcacaaccactacacgcaga agagcctctccctgtctccgggtaaatga
```

Humanized heavy chain nucleic acid sequence - 19 aa leader sequence

SEQ ID NO: 101

```
atgggctggagctggatcctgctgttcctcctgagcgtgacagcaggagtgcacagccaggtgcagctggtgcagtctggggccgaa gtgaagaaacccggagcatcagtcaaagtcagttgtaaggcatcaggctatacattcacatcttacgtgatgcactgggtccggcagg ctccaggacagagactggagtggatcgggtacattaaccctracaacgacggaactaagtacaacgaaaagttcaaaggcagggt gaccatcacatcagatacttctgccagtaccgcttacatggagctgagctccctgcggagcgaagacaccgcagtctactattgcgcc aattattatgggctcaaactacgctatggactattgggggcaggggacactggtgaccgtctcctcagctagcaccaagggcccatcgg tcttccccctggcaccctcctccaagagcacctctgggggcacagcggccctgggctgcctggtcaaggactacttccccgaaccggt gacggtgtcgtggaactcaggcgccctgaccagcggcgtgcacaccttcccggctgtcctacagtcctcaggactctactccctcagc agcgtggtgaccgtgccctccagcagcttgggcacccagacctacatctgcaacgtgaatcacaagcccagcaacaccaaggtgg
```

-continued acaagaaagttgagcccaaatcttgtgacaaaactcacacatgcccaccgtgcccagcacctgaactcctggggggaccgtcagtc
ttcctcttccccccaaaacccaaggacaccctcatgatctcccggacccctgaggtcacatgcgtggtggtggacgtgagccacgaa
gaccctgaggtcaagttcaactggtacgtggacggcgtggaggtgcataatgccaagacaaagccgcgggaggagcagtacaac
agcacgtaccgtgtggtcagcgtcctcaccgtcctgcaccaggactggctgaatggcaaggagtacaagtgcaaggtctccaacaa
agcccctcccagcccccatcgagaaaaccatctccaaagccaaagggcagccccgagaaccacaggtgtacaccctgcccccatc
ccgggatgagctgaccaagaaccaggtcagcctgacctgcctggtcaaaggcttctatcccagcgacatcgccgtggagtgggaga
gcaatgggcagccggagaacaactacaagaccacgcctcccgtgctggactccgacggctccttcttcctctacagcaagctcacc
gtggacaagagcaggtggcagcaggggaacgtcttctcatgctccgtgatgcatgaggctctgcacaaccactacacgcagaaga
gcctctccctgtctccgggtaaatga Humanized heavy chain nucleic acid sequence - 19 aa leader sequence

SEQ ID NO: 102 atgggctggagctggatcctgctgttcctcctgagcgtgacagcaggagtgcacagccaggtgcagctggtccagagcggagcaga
agtcaagaaacccggcgcaagtgtgaagatgagttgtaaggcaagcggctatacattcacatcttacgtgatgcactgggtcaagca
ggctccaggacagaggctggagtggatcgggtacatcaaccct tacaacgacggaactaagtacaacgaaaagttcaaaggccg
ggtgaccatcacatcagatacttctgccagtaccgcttacatggagctgagctccctgagaagcgaagacaccgcagtctactattgc
gccaattattatggctctaactatgctatggattattggggcagggcactctggtcaccgtgtcaagcgctagcaccaagggcccatc
ggtcttccccctggcaccctcctccaagagcacctctggggg cacagcggccctgggctgcctggtcaaggactacttccccgaacc
ggtgacggtgtcgtggaactcaggcgccctgaccagcggcgtgcacaccttcccggctgtcctacagtcctcaggactctactccctc
agcagcgtggtgaccgtgccctccagcagcttgggcacccagacctacatctgcaacgtgaatcacaagcccagcaacaccaagg
tggacaagaaagttgagcccaaatcttgtgacaaaactcacacatgcccaccgtgcccagcacctgaactcctggggggaccgtca
gtcttcctcttccccccaaaacccaaggacaccctcatgatctcccggacccctgaggtcacatgcgtggtggtggacgtgagccacg
aagaccctgaggtcaagttcaactggtacgtggacggcgtggaggtgcataatgccaagacaaagccgcgggaggagcagtaca
acagcacgtaccgtgtggtcagcgtcctcaccgtcctgcaccaggactggctgaatggcaaggagtacaagtgcaaggtctccaac
aaagcccctcccagcccccatcgagaaaaccatctccaaagccaaagggcagccccgagaaccacaggtgtacaccctgccccc
atcccgggatgagctgaccaagaaccaggtcagcctgacctgcctggtcaaaggcttctatcccagcgacatcgccgtggagtggg
agagcaatgggcagccggagaacaactacaagaccacgcctcccgtgctggactccgacggctccttcttcctctacagcaagctc
accgtggacaagagcaggtggcagcaggggaacgtcttctcatgctccgtgatgcatgaggctctgcacaaccactacacgcaga
agagcctctccctgtctccgggtaaatga Humanized heavy chain nucleic acid sequence - 19 aa leader sequence

SEQ ID NO: 103 atgggctggagctggatcctgctgttcctcctgagcgtgacagcaggagtgcacagccaggtgcagctggtccagagcggagcaga
ggtgaagaaaccccggagcatcagtcaaaatgtcctgtaaggcaagcggctatactttcacatcttacgtgatgcactgggtcaagcag
gctccaggacagaggctggagtggatcgggtacatcaaccct tacaacgacggaactaagtacaacgaaaagttcaaaggccgg
gccaccctgacatcagatacttctgccagtaccgcttacatggagctgagctccctgagaagcgaagacaccgcagtgtactattgcg
ccaattattatgggtcaaactacgctatggactattggggcagggcactctggtcactgtcagcagcgctagcaccaagggcccatc
ggtcttccccctggcaccctcctccaagagcacctctggggg cacagcggccctgggctgcctggtcaaggactacttccccgaacc
ggtgacggtgtcgtggaactcaggcgccctgaccagcggcgtgcacaccttcccggctgtcctacagtcctcaggactctactccctc
agcagcgtggtgaccgtgccctccagcagcttgggcacccagacctacatctgcaacgtgaatcacaagcccagcaacaccaagg
tggacaagaaagttgagcccaaatcttgtgacaaaactcacacatgcccaccgtgcccagcacctgaactcctggggggaccgtca
gtcttcctcttccccccaaaacccaaggacaccctcatgatctcccggacccctgaggtcacatgcgtggtggtggacgtgagccacg
aagaccctgaggtcaagttcaactggtacgtggacggcgtggaggtgcataatgccaagacaaagccgcgggaggagcagtaca
acagcacgtaccgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacaccctgccccc atcccgggatgagctgaccaagaaccaggtcagcctgacctgcctggtcaaaggcttctatcccagcgacatcgccgtggagtggg agagcaatgggcagccggagaacaactacaagaccacgcctcccgtgctggactccgacggctccttcttcctctacagcaagctc accgtggacaagagcaggtggcagcaggggaacgtcttctcatgctccgtgatgcatgaggctctgcacaaccactacacgcaga agagcctctccctgtctccgggtaaatga Humanized heavy chain nucleic acid sequence - 19 aa leader sequence

SEQ ID NO: 104 atgggctggagctggatcctgctgttcctcctgagcgtgacagcaggagtgcacagccaggtccagctggtgcagagcggagcaga ggtgaagaaacccggcgcaagcgtcaaggtgtcctgtaaggcaagcggctatacttttacatcttacgtgatgcactgggtcaaacag gctccaggacagcggctggagtggatcggatacattaaccctttacaacgacggaactaagtacaacgaaaagttcaaaggcaag gccaccctgacatcagatacttctgccagtaccgcttacatggagctgagctccctgagaagcgaagacaccgcagtgtactattgcg ccaattattatggctcaaactatgctatggattattgggggcagggaacactggtcaccgtctcatcagctagcaccaagggcccatcg gtcttccccctggcaccctcctccaagagcacctctggggcacagcggccctgggctgcctggtcaaggactacttccccgaaccg gtgacggtgtcgtggaactcaggcgccctgaccagcggcgtgcacaccttcccggctgtcctacagtcctcaggactctactccctca gcagcgtggtgaccgtgccctccagcagcttgggcacccagacctacatctgcaacgtgaatcacaagcccagcaacaccaaggt ggacaagaaagttgagcccaaatcttgtgacaaaactcacacatgcccaccgtgcccagcacctgaactcctggggggaccgtca gtcttcctcttccccccaaaacccaaggacaccctcatgatctcccggacccctgaggtcacatgcgtggtggtggacgtgagccacg aagaccctgaggtcaagttcaactggtacgtggacggcgtggaggtgcataatgccaagacaaagccgcgggaggagcagtaca acagcacgtaccgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacaccctgccccc atcccgggatgagctgaccaagaaccaggtcagcctgacctgcctggtcaaaggcttctatcccagcgacatcgccgtggagtggg agagcaatgggcagccggagaacaactacaagaccacgcctcccgtgctggactccgacggctccttcttcctctacagcaagctc accgtggacaagagcaggtggcagcaggggaacgtcttctcatgctccgtgatgcatgaggctctgcacaaccactacacgcaga agagcctctccctgtctccgggtaaatga Humanized heavy chain nucleic acid sequence - 19 aa leader sequence

SEQ ID NO: 105 atgggctggagctggatcctgctgttcctcctgagcgtgacagcaggagtgcacagcgaagtgcagctggtgcagagcggggcaga agtgaagaagcctggggaaagcctgaagattagttgtaaagggagcggatatacattcacttcttacgtgatgcactgggtccggcag atgccaggcaagggactggagtggatgggatacatcaaccctttataatgacggcaccaaatataacgaaaagttcaaagggcagg tgaccatctcagcagacaagtctattagtacagcctacctgcagtggagctccctgaaagccagcgacacagctatgtactattgcgct agatattatggctcaaactacgctatggactactggggacagggggactatggtcaccgtctcaagcgctagcaccaagggcccatcg gtcttccccctggcaccctcctccaagagcacctctggggcacagcggccctgggctgcctggtcaaggactacttccccgaaccg gtgacggtgtcgtggaactcaggcgccctgaccagcggcgtgcacaccttcccggctgtcctacagtcctcaggactctactccctca gcagcgtggtgaccgtgccctccagcagcttgggcacccagacctacatctgcaacgtgaatcacaagcccagcaacaccaaggt ggacaagaaagttgagcccaaatcttgtgacaaaactcacacatgcccaccgtgcccagcacctgaactcctggggggaccgtca gtcttcctcttccccccaaaacccaaggacaccctcatgatctcccggacccctgaggtcacatgcgtggtggtggacgtgagccacg aagaccctgaggtcaagttcaactggtacgtggacggcgtggaggtgcataatgccaagacaaagccgcgggaggagcagtaca acagcacgtaccgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacaccctgccccc atcccgggatgagctgaccaagaaccaggtcagcctgacctgcctggtcaaaggcttctatcccagcgacatcgccgtggagtggg agagcaatgggcagccggagaacaactacaagaccacgcctcccgtgctggactccgacggctccttcttcctctacagcaagctc accgtggacaagagcaggtggcagcaggggaacgtcttctcatgctccgtgatgcatgaggctctgcacaaccactacacgcag a agagcctctccctgtctccgggtaaatga Humanized heavy chain nucleic acid sequence - 19 aa leader sequence

SEQ ID NO: 106 atgggctggagctggatcctgctgttcctcctgagcgtgacagcaggagtgcacagcgaggtccagctggtgcagagcggagcaga
ggtcaagaagcccggcgaatcagtgaagatgtcctgtaagggaagcggatatactttcacttcctacgtgatgcactgggtcaagca
gatgcccggcaaagggctggagtggatcggatacattaacccttataatgacggcaccaagtataacgaaaagttcaaagggcag
gcaaccctgagctccgataagtcaatcagcacagcctacatgcagctgtctagtctgaaagccagtgacacagctatgtactattgcg
ctaattattatgggtcaaactacgcaatggattactgggggcagggaacaatggtcactgtctcttcagctagcaccaagggcccatcg
gtcttccccctggcaccctcctccaagagcacctctgggggcacagcggccctgggctgcctggtcaaggactacttccccgaaccg
gtgacggtgtcgtggaactcaggcgccctgaccagcggcgtgcacaccttcccggctgtcctacagtcctcaggactctactccctca
gcagcgtggtgaccgtgccctccagcagcttgggcacccagacctacatctgcaacgtgaatcacaagcccagcaacaccaaggt
ggacaagaaagttgagcccaaatcttgtgacaaaactcacacatgcccaccgtgcccagcacctgaactcctggggggaccgtca
gtcttcctcttccccccaaaacccaaggacaccctcatgatctcccggacccctgaggtcacatgcgtggtggtggacgtgagccacg
aagaccctgaggtcaagttcaactggtacgtggacggcgtggaggtgcataatgccaagacaaagccgcgggaggagcagtaca
acagcacgtaccgtgtggtcagcgtcctcaccgtcctgcaccaggactggctgaatggcaaggagtacaagtgcaaggtctccaac
aaagccctcccagcccccatcgagaaaaccatctccaaagccaaagggcagccccgagaaccacaggtgtacaccctgcccccc
atcccgggatgagctgaccaagaaccaggtcagcctgacctgcctggtcaaaggcttctatcccagcgacatcgccgtggagtggg
agagcaatgggcagccggagaacaactacaagaccacgcctcccgtgctggactccgacggctccttcttcctctacagcaagctc
accgtggacaagagcaggtggcagcaggggaacgtcttctcatgctccgtgatgcatgaggctctgcacaaccactacacgcaga
agagcctctccctgtctccgggtaaatga Humanized light chain nucleic acid sequence - 19 aa leader sequence

SEQ ID NO: 107 atgggctggagctggatcctgctgttcctcctgagcgtgacagcaggagtgcacagcgacattcagatgacccagagccttccagc
ctgagtgccagcgtcggagatagagtgacaattacttgccgcgccagccaggacattaggaactacctgaattggtatcagcagaag
cccggcaaagcccctaagctgctgatctactatacaagccggctgcactccggggtgccaagtagattctctggcagtgggtcagga
actgacttcaccttttacaatcagctccctgcagcccgaggatattgctacctactattgtcagcagggaaatacactgccttggaccttcg
gcggggggactaaactggaaatcaaacgaacggtggctgcaccatctgtcttcatcttcccgccatctgatgagcagttgaaatctgg
aactgcctctgttgtgtgcctgctgaataacttctatcccagagaggccaaagtacagtggaaggtggataacgccctccaatcgggta
actcccaggagagtgtcacagagcaggacagcaaggacagcacctacagcctcagcagcaccctgacgctgagcaaagcaga
ctacgagaaacacaaagtctacgcctgcgaagtcacccatcagggcctgagctcgcccgtcacaaagagcttcaacaggggaga
gtgttag Humanizedlight chain nucleic acid sequence - 19 aa leader sequence

SEQ ID NO: 108 atgggctggagctggatcctgctgttcctcctgagcgtgacagcaggagtgcacagcgacattcagatgacccagagccttccagc
ctgagcgccagcgtcggagacagagtgactattacttgtagagccagccaggacattaggaactacctgaattggtatcagcagaa
gcccggcaaagccgtgaagctgctgatctactatacaagccggctgcactccggggtccctagtagattctctggcagtgggtcagga
actgacttcaccttttacaatcagctccctgcagcccgaggatattgctacctactttgtcagcagggaaatacactgccttggaccttcg
gaggggggactaaactggaaatcaaacgaacggtggctgcaccatctgtcttcatcttcccgccatctgatgagcagttgaaatctgg
aactgcctctgttgtgtgcctgctgaataacttctatcccagagaggccaaagtacagtggaaggtggataacgccctccaatcgggta
actcccaggagagtgtcacagagcaggacagcaaggacagcacctacagcctcagcagcaccctgacgctgagcaaagcaga
ctacgagaaacacaaagtctacgcctgcgaagtcacccatcagggcctgagctcgcccgtcacaaagagcttcaacaggggaga
gtgttag Humanized light chain nucleic acid sequence - 19 aa leader sequence

SEQ ID NO: 109 atgggctggagctggatcctgctgttcctcctgagcgtgacagcaggagtgcacagcgatattcagatgacccagtcaccttccagtct -continued

```
gagtgccagcgtcggggatagagtcaccattacttgccgcgccagccaggacattaggaactacctgaattggtatcagcagaagc ccggcggggccgtgaaactgctgatctactatacaagccggctgcactccggcgtccctagtagattctctggaagtggctcagggac tgactttaccctgacaatcagctccctgcagcccgaggatattgctacctacttctgtcagcagggaaatacactgccttggaccttcgg agggggactaaactggaaatcaaacgaacggtggctgcaccatctgtcttcatcttcccgccatctgatgagcagttgaaatctgga actgcctctgttgtgtgcctgctgaataacttctatcccagagaggccaaagtacagtggaaggtggataacgccctccaatcgggtaa ctcccaggagagtgtcacagagcaggacagcaaggacagcacctacagcctcagcagcaccctgacgctgagcaaagcagact acgagaaacacaaagtctacgcctgcgaagtcacccatcagggcctgagctcgcccgtcacaaagagcttcaacaggggagagt gttag
```

Humanized light chain nucleic acid sequence - 19 aa leader sequence

SEQ ID NO: 110

```
atgggctggagctggatcctgctgttcctcctgagcgtgacagcaggagtgcacagcgacattcagatgacccagagccccagcag cctgagcgccagcgtcggagatagagtgaccattacttgtagagccagccaggacattaggaactacctgaattggtatcagcagaa gcccggcggggccgtgaaactgctgatctactatacaagccggctgcactccggcgtccctagtagattctctggaagtggctcaggg actgactacaccctgacaatcagctccctgcagcccgaggatattgctacctatttttgtcagcagggaaatactctgccttggaccttcg gcggagggactaaactggaaatcaaacgaacggtggctgcaccatctgtcttcatcttcccgccatctgatgagcagttgaaatctgg aactgcctctgttgtgtgcctgctgaataacttctatcccagagaggccaaagtacagtggaaggtggataacgccctccaatcgggta actcccaggagagtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagcttcaacaggggaga gtgttag
```

Humanized light chain nucleic acid sequence - 19 aa leader sequence

SEQ ID NO: 111

```
atgggctggagctggatcctgctgttcctcctgagcgtgacagcaggagtgcacagcgacattcagatgacccagagcccttccagc ctgagtgcttccgtcggggatagagtgacaattagttgcagagccagccaggacattaggaactacctgaattggtatcagcagaag cccggcaaaactgtgaagctgctgatctactataccagccggctgcactccggggtccctagtagattctctggcagtgggtcaggaa cagactacaccctttacaatcagctccctgcagcccgaggatattgccacctatttctgtcagcagggaaatactctgccttggaccttcg gcggcggaactaaactggaaatcaaacgaacggtggctgcaccatctgtcttcatcttcccgccatctgatgagcagttgaaatctgg aactgcctctgttgtgtgcctgctgaataacttctatcccagagaggccaaagtacagtggaaggtggataacgccctccaatcgggta actcccaggagagtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagcttcaacaggggaga gtgttag
```

Humanized light chain nucleic acid sequence - 19 aa leader sequence

SEQ ID NO: 112

```
atgggctggagctggatcctgctgttcctcctgagcgtgacagcaggagtgcacagcgaaatcgtgctgacccagtcccccgccaca ctgagtctgtcccccggagaaagagccaccctgagctgtagggcaagccaggatattcggaactacctgaattggtatcagcagaa gccaggacaggcacctcgactgctgatctactatactagcagactgcactctgggattccagctaggttctctggcagtgggtcagga accgactttaccctgacaatcagctccctggagcccgaagatttcgccgtgtactattgccagcaggggaatactctgccttggaccttc ggccaggggactaaagtggaaatcaaacgaacggtggctgcaccatctgtcttcatcttcccgccatctgatgagcagttgaaatctg gaactgcctctgttgtgtgcctgctgaataacttctatcccagagaggccaaagtacagtggaaggtggataacgccctccaatcgggt aactcccaggagagtgtcacagagcaggacagcaaggacagcacctacagcctcagcagcaccctgacgctgagcaaagcag actacgagaaacacaaagtctacgcctgcgaagtcacccatcagggcctgagctcgcccgtcacaaagagcttcaacaggggag agtgttag
```

Humanized light chain nucleic acid sequence - 19 aa leader sequence

SEQ ID NO: 113

```
atgggctggagctggatcctgctgttcctcctgagcgtgacagcaggagtgcacagcgaaatcgtgatgacccagagcccagccac actgtccgccagcccaggcgagagagtcacactgtcttgccgagccagccaggatattcggaactacctgaattggtatcagcagaa
```

```
gccaggaggagccgtgcggctgctgatctactatactagcagactgcactctggcgtccctgctaggttctctggaagtggctcaggg accgactacaccctgacaattagctccctggagcccgaagattacgccgtgtattttgccagcagggaaatactctgccttggacattc ggacaggggactaaagtggaaatcaaacgaacggtggctgcaccatctgtcttcatcttcccgccatctgatgagcagttgaaatctg gaactgcctctgttgtgtgcctgctgaataacttctatcccagagaggccaaagtacagtggaaggtggataacgccctccaatcgggt aactcccaggagagtgtcacagagcaggacagcaaggacagcacctacagcctcagcagcaccctgacgctgagcaaagcag actacgagaaacacaaagtctacgcctgcgaagtcacccatcagggcctgagctcgcccgtcacaaagagcttcaacaggggag agtgttag
```

---

What is claimed is:

1. An isolated antibody, or antigen-binding fragment thereof, which specifically binds human OX40 and comprises: (a) the light chain CDR1, CDR2, and CDR3 sequences set forth in SEQ ID NO: 18, SEQ ID NO: 22, and SEQ ID NO: 26 and the heavy chain CDR1, CDR2, and CDR3 sequences set forth in SEQ ID NO: 2, SEQ ID NO: 8, and SEQ ID NO: 13; (b) the light chain CDR1, CDR2, and CDR3 sequences set forth in SEQ ID NO: 18, SEQ ID NO: 22, and SEQ ID NO: 26 and the heavy chain CDR1, CDR2, and CDR3 sequences set forth in SEQ ID NO: 3, SEQ ID NO: 9, and SEQ ID NO: 13; (c) the light chain CDR1, CDR2, and CDR3 sequences set forth in SEQ ID NO: 19, SEQ ID NO: 23, and SEQ ID NO: 27 and the heavy chain CDR1, CDR2, and CDR3 sequences set forth in SEQ ID NO: 4, SEQ ID NO: 10, and SEQ ID NO: 14; (d) the light chain CDR1, CDR2, and CDR3 sequences set forth in SEQ ID NO: 20, SEQ ID NO: 24, and SEQ ID NO: 28 and the heavy chain CDR1, CDR2, and CDR3 sequences set forth in SEQ ID NO: 5, SEQ ID NO: 11, and SEQ ID NO: 15; (e) the light chain CDR1, CDR2, and CDR3 sequences set forth in SEQ ID NO: 21, SEQ ID NO: 25, and SEQ ID NO: 28 and the heavy chain CDR1, CDR2, and CDR3 sequences set forth in SEQ ID NO: 6, SEQ ID NO: 12, and SEQ ID NO: 16; (f) the light chain CDR1, CDR2, and CDR3 sequences set forth in SEQ ID NO: 20, SEQ ID NO: 24, and SEQ ID NO: 28 and the heavy chain CDR1, CDR2, and CDR3 sequences set forth in SEQ ID NO: 7, SEQ ID NO: 11, and SEQ ID NO: 17.

2. An isolated antibody or antigen-binding fragment thereof according to claim 1, which comprises: (a) a light chain CDR1 sequence set forth in SEQ ID NO: 20; (b) a light chain CDR2 sequence set forth in SEQ ID NO: 24; (c) a light chain CDR3 sequence set forth in SEQ ID NO: 28; (d) a heavy chain CDR1 set forth in SEQ ID NO: 7; (e) a heavy chain CDR2 sequence set forth in SEQ ID NO: 11; and (f) a heavy chain CDR3 sequence set forth in SEQ ID NO: 17.

3. The isolated antibody or antigen-binding fragment thereof according to claim 1 that binds to OX40 with a dissociation constant ($K_D$) of at least about $1 \times 10^{-6}$ M, at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, or at least about $1 \times 10^{-12}$ M.

4. An isolated antibody or antigen-binding fragment thereof according to claim 1 wherein the antibody or antigen-binding fragment is selected from a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, a Fab' fragment, a $Fab_2$ fragment, a $F(ab)'_2$ fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region that alleviates a tendency to form intra H-chain disulfide bonds.

5. An isolated humanized antibody or antigen-binding fragment thereof according to claim 4 which comprises (a) a heavy chain variable region comprising amino acids having the sequence set forth in SEQ ID NO: 61, and a light chain variable region comprising amino acids having the sequence set forth in SEQ ID NO: 67; (b) a heavy chain variable region comprising amino acids having the sequence set forth in SEQ ID NO: 61, and a light chain variable region comprising amino acids having the sequence set forth in SEQ ID NO: 68; and (c) a heavy chain variable region comprising amino acids having the sequence set forth in SEQ ID NO: 61, and a light chain variable region comprising amino acids having the sequence set forth in SEQ ID NO: 69.

6. An isolated humanized antibody or antigen-binding fragment thereof according to claim 5, which comprises the heavy chain variable region sequence of SEQ ID NO: 61, and the light chain variable region sequence of SEQ ID NO: 67.

7. An isolated humanized antibody or antigen-binding fragment thereof according to claim 5, which comprises the heavy chain variable region sequence of SEQ ID NO: 61, and the light chain variable region sequence of SEQ ID NO: 68.

8. An isolated humanized antibody or antigen-binding fragment thereof according to claim 5, which comprises the heavy chain variable region sequence of SEQ ID NO: 61, and the light chain variable region sequence of SEQ ID NO: 69.

9. An isolated humanized antibody or antigen-binding fragment thereof according to claim 4 which comprises a comprises (a) a heavy chain comprising amino acids having the sequence set forth in SEQ ID NO: 91, and a light chain comprising amino acids having the sequence set forth in SEQ ID NO: 97; (b) a heavy chain comprising amino acids having the sequence set forth in SEQ ID NO: 91, and a light chain comprising amino acids having the sequence set forth in SEQ ID NO: 98; (c) a heavy chain comprising amino acids having the sequence set forth in SEQ ID NO: 91, and a light chain comprising amino acids having the sequence set forth in SEQ ID NO: 99.

10. An isolated humanized antibody or antigen-binding fragment thereof according to claim 9, which comprises the heavy chain sequence of SEQ ID NO: 91, and the light chain sequence of SEQ ID NO: 97.

11. An isolated humanized antibody or antigen-binding fragment thereof according to claim 9, which comprises the heavy chain sequence of SEQ ID NO: 91, and the light chain sequence of SEQ ID NO: 98.

12. An isolated humanized antibody or antigen-binding fragment thereof according to claim 9, which comprises the heavy chain sequence of SEQ ID NO: 91, and the light chain sequence of SEQ ID NO: 99.

13. A pharmaceutical composition comprising an isolated antibody or antigen-binding fragment thereof according to claim 1 in admixture with a pharmaceutically acceptable carrier.

14. A method of activating OX40 in a subject, comprising administering to said subject a therapeutically effective amount of an isolated humanized antibody or antigen-binding fragment thereof according to claim 5.

15. A method according to claim 14, wherein said subject is suffering from a cancer, and selected from a method comprising: a) administering to said subject effective amount of an isolated humanized antibody or antigen-binding fragment thereof according to claim 5; and b) a method further comprising one or more additional therapies selected from the group consisting of immunotherapy, chemotherapy, small molecule kinase inhibitor targeted therapy, surgery, radiation therapy, vaccination protocols, and stem cell transplantation, wherein the combination therapy provides increased cell killing of tumor cells.

16. An isolated immunoconjugate or fusion protein comprising an antibody or antigen-binding fragment thereof according to claim 1 coupled to an effector molecule.

* * * * *

SEQUENCE LISTING

<160> NUMBER OF SEQ ID NOS: 113

<210> SEQ ID NO 1
<211> LENGTH: 249
<212> TYPE: PRT
<213> ORGANISM: Homo sapiens

<400> SEQUENCE: 1

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

<210> SEQ ID NO 2
<211> LENGTH: 5

```
<212> TYPE: PRT
<213> ORGANISM: Mus musculus

<400> SEQUENCE: 2

Asp Tyr Ala Ile His
1               5

<210> SEQ ID NO 3
<211> LENGTH: 5
<212> TYPE: PRT
<213> ORGANISM: Mus musculus

<400> SEQUENCE: 3

Asp Tyr Ala Met His
1               5

<210> SEQ ID NO 4
<211> LENGTH: 5
<212> TYPE: PRT
<213> ORGANISM: Mus musculus

<400> SEQUENCE: 4

Ser Tyr Gly Val His
1               5

<210> SEQ ID NO 5
<211> LENGTH: 5
<212> TYPE: PRT
<213> ORGANISM: Mus musculus

<400> SEQUENCE: 5

Ser Tyr Ile Met His
1               5

<210> SEQ ID NO 6
<211> LENGTH: 5
<212> TYPE: PRT
<213> ORGANISM: Mus musculus

<400> SEQUENCE: 6

Glu Asn Tyr Met Asn
1               5

<210> SEQ ID NO 7
<211> LENGTH: 5
<212> TYPE: PRT
<213> ORGANISM: Mus musculus

<400> SEQUENCE: 7

Ser Tyr Val Met His
1               5

<210> SEQ ID NO 8
<211> LENGTH: 17
<212> TYPE: PRT
<213> ORGANISM: Mus musculus

<400> SEQUENCE: 8

Val Ile Asn Thr Tyr Tyr Gly Asp Ala Ala Tyr Asn Gln Lys Phe Gln
1               5                   10                  15

Gly

<210> SEQ ID NO 9
<211> LENGTH: 17
```

```
<212> TYPE: PRT
<213> ORGANISM: Mus musculus

<400> SEQUENCE: 9

Val Ile Ser Thr Tyr Tyr Gly Asp Ala Ala Tyr Asn Gln Lys Phe Lys
1               5                   10                  15
Asp

<210> SEQ ID NO 10
<211> LENGTH: 16
<212> TYPE: PRT
<213> ORGANISM: Mus musculus

<400> SEQUENCE: 10

Val Ile Trp Ala Gly Gly Ser Thr Asp Tyr Asn Ser Ala Leu Met Ser
1               5                   10                  15

<210> SEQ ID NO 11
<211> LENGTH: 17
<212> TYPE: PRT
<213> ORGANISM: Mus musculus

<400> SEQUENCE: 11

Tyr Ile Asn Pro Tyr Asn Asp Gly Thr Lys Tyr Asn Glu Lys Phe Lys
1               5                   10                  15
Gly

<210> SEQ ID NO 12
<211> LENGTH: 17
<212> TYPE: PRT
<213> ORGANISM: Mus musculus

<400> SEQUENCE: 12

Asp Ile Asn Arg Asn Asn Gly Gly Thr Arg Tyr Asn Gln Lys Phe Lys
1               5                   10                  15
Gly

<210> SEQ ID NO 13
<211> LENGTH: 6
<212> TYPE: PRT
<213> ORGANISM: Mus musculus

<400> SEQUENCE: 13

Leu Asp Asp Phe Val Tyr
1               5

<210> SEQ ID NO 14
<211> LENGTH: 5
<212> TYPE: PRT
<213> ORGANISM: Mus musculus

<400> SEQUENCE: 14

Glu Glu Val Trp Asp
1               5

<210> SEQ ID NO 15
<211> LENGTH: 10
<212> TYPE: PRT
<213> ORGANISM: Mus musculus

<400> SEQUENCE: 15

Tyr Tyr Gly Ser Ser Tyr Thr Met Asp Tyr
1               5                   10
```

<210> SEQ ID NO 16
<211> LENGTH: 8
<212> TYPE: PRT
<213> ORGANISM: Mus musculus

<400> SEQUENCE: 16

Thr Val Val Gly Tyr Phe Asp Val
1               5

<210> SEQ ID NO 17
<211> LENGTH: 10
<212> TYPE: PRT
<213> ORGANISM: Mus musculus

<400> SEQUENCE: 17

Tyr Tyr Gly Ser Asn Tyr Ala Met Asp Tyr
1               5                   10

<210> SEQ ID NO 18
<211> LENGTH: 16
<212> TYPE: PRT
<213> ORGANISM: Mus musculus

<400> SEQUENCE: 18

Lys Ser Ser Gln Ser Leu Leu Asp Ser Asp Gly Lys Thr Tyr Leu Asn
1               5                   10                  15

<210> SEQ ID NO 19
<211> LENGTH: 11
<212> TYPE: PRT
<213> ORGANISM: Mus musculus

<400> SEQUENCE: 19

Arg Ala Ser Gln Asp Ile Ser Asn Tyr Leu Asn
1               5                   10

<210> SEQ ID NO 20
<211> LENGTH: 11
<212> TYPE: PRT
<213> ORGANISM: Mus musculus

<400> SEQUENCE: 20

Arg Ala Ser Gln Asp Ile Arg Asn Tyr Leu Asn
1               5                   10

<210> SEQ ID NO 21
<211> LENGTH: 11
<212> TYPE: PRT
<213> ORGANISM: Mus musculus

<400> SEQUENCE: 21

Arg Ser Ser Gln Asp Ile Ser Asn Tyr Leu Asn
1               5                   10

<210> SEQ ID NO 22
<211> LENGTH: 7
<212> TYPE: PRT
<213> ORGANISM: Mus musculus

<400> SEQUENCE: 22

Leu Val Ser Lys Leu Asp Ser
1               5

```
<210> SEQ ID NO 23
<211> LENGTH: 7
<212> TYPE: PRT
<213> ORGANISM: Mus musculus

<400> SEQUENCE: 23

Tyr Thr Ser Arg Leu Gln Ser
1               5

<210> SEQ ID NO 24
<211> LENGTH: 7
<212> TYPE: PRT
<213> ORGANISM: Mus musculus

<400> SEQUENCE: 24

Tyr Thr Ser Arg Leu His Ser
1               5

<210> SEQ ID NO 25
<211> LENGTH: 7
<212> TYPE: PRT
<213> ORGANISM: Mus musculus

<400> SEQUENCE: 25

Tyr Thr Ser Arg Leu Lys Ser
1               5

<210> SEQ ID NO 26
<211> LENGTH: 9
<212> TYPE: PRT
<213> ORGANISM: Mus musculus

<400> SEQUENCE: 26

Trp Gln Gly Thr His Phe Pro Arg Thr
1               5

<210> SEQ ID NO 27
<211> LENGTH: 9
<212> TYPE: PRT
<213> ORGANISM: Mus musculus

<400> SEQUENCE: 27

Gln Gln Gly Asn Thr Leu Pro Leu Thr
1               5

<210> SEQ ID NO 28
<211> LENGTH: 9
<212> TYPE: PRT
<213> ORGANISM: Mus musculus

<400> SEQUENCE: 28

Gln Gln Gly Asn Thr Leu Pro Trp Thr
1               5

<210> SEQ ID NO 29
<211> LENGTH: 402
<212> TYPE: DNA
<213> ORGANISM: Mus musculus

<400> SEQUENCE: 29
atgggttgga gctgtatcat cttctttctg gtagcaacag ctacaggtgt gcactcccag      60
gtccagctgc aacagtctgg ggctgagctg gtgaggcctg ggtctcagt gaagatttcc      120 tgcaagggtt ctgactacac attcactgat tatgctatac actgggtgaa gcagagtcct    180
```

-continued

```
gcaaagagtc tagagtggat tggagttatt aatacttact atggtgatgc tgcctacaac    240
cagaagttcc agggcaaggc cacaatgact gtagacaaat cctccagcgc agcctatatg    300
gaacttgcca gactgacatc tgaggattct gccatctatt actgtgcaag attagacgat    360 tttgttact ggggccaagg gactctggtc actgtctctg ca                        402
```

<210> SEQ ID NO 30
<211> LENGTH: 134
<212> TYPE: PRT
<213> ORGANISM: Mus musculus

<400> SEQUENCE: 30

```
Met Gly Trp Ser Cys Ile Ile Phe Phe Leu Val Ala Thr Ala Thr Gly
1               5                   10                  15

Val His Ser Gln Val Gln Leu Gln Gln Ser Gly Ala Glu Leu Val Arg
            20                  25                  30

Pro Gly Val Ser Val Lys Ile Ser Cys Lys Gly Ser Asp Tyr Thr Phe
        35                  40                  45

Thr Asp Tyr Ala Ile His Trp Val Lys Gln Ser Pro Ala Lys Ser Leu
    50                  55                  60

Glu Trp Ile Gly Val Ile Asn Thr Tyr Tyr Gly Asp Ala Ala Tyr Asn
65                  70                  75                  80

Gln Lys Phe Gln Gly Lys Ala Thr Met Thr Val Asp Lys Ser Ser Ser
                85                  90                  95

Ala Ala Tyr Met Glu Leu Ala Arg Leu Thr Ser Glu Asp Ser Ala Ile
            100                 105                 110

Tyr Tyr Cys Ala Arg Leu Asp Asp Phe Val Tyr Trp Gly Gln Gly Thr
        115                 120                 125

Leu Val Thr Val Ser Ala
    130
```

<210> SEQ ID NO 31
<211> LENGTH: 402
<212> TYPE: DNA
<213> ORGANISM: Mus musculus

<400> SEQUENCE: 31

```
atgggttgga gctgtatcat cttctttctg gtagcaacag ctacaggtgt gcactcccag    60
gtccagctgc agcagtctgg ggctgagctg gtgaggcctg ggtctcagt gaagatttac     120 tgcaagggtt ctggctacac attcactgat tacgctatgc actgggtgaa gcagagtcat    180
gcaaagagtc tagagtggat tggagttatt agtacttact atggtgatgc tgcttacaac    240
cagaaattca aggacaaggc cacaatgact gtagacaaat cctccagcac agcctatatg    300
gaacttgcca gactgacatc tgaggattct gccatctatt actgtgcaag attagacgat    360 tttgttact ggggccaagg gactctggtc actgtctctg ca                        402
```

<210> SEQ ID NO 32
<211> LENGTH: 134
<212> TYPE: PRT
<213> ORGANISM: Mus musculus

<400> SEQUENCE: 32

```
Met Gly Trp Ser Cys Ile Ile Phe Phe Leu Val Ala Thr Ala Thr Gly
1               5                   10                  15

Val His Ser Gln Val Gln Leu Gln Gln Ser Gly Ala Glu Leu Val Arg
            20                  25                  30
```

Pro Gly Val Ser Val Lys Ile Tyr Cys Lys Gly Ser Gly Tyr Thr Phe
            35                  40                  45

Thr Asp Tyr Ala Met His Trp Val Lys Gln Ser His Ala Lys Ser Leu
 50                  55                  60

Glu Trp Ile Gly Val Ile Ser Thr Tyr Gly Asp Ala Ala Tyr Asn
65                   70                  75                  80

Gln Lys Phe Lys Asp Lys Ala Thr Met Thr Val Asp Lys Ser Ser Ser
                85                  90                  95

Thr Ala Tyr Met Glu Leu Ala Arg Leu Thr Ser Glu Asp Ser Ala Ile
                100                 105                 110

Tyr Tyr Cys Ala Arg Leu Asp Asp Phe Val Tyr Trp Gly Gln Gly Thr
            115                 120                 125

Leu Val Thr Val Ser Ala
    130

<210> SEQ ID NO 33
<211> LENGTH: 396
<212> TYPE: DNA
<213> ORGANISM: Mus musculus

<400> SEQUENCE: 33
atggctgtcc tggtgctgtt cctctgcctg gttgcatttc caagctgtgt cctgtcccag      60
gtgcagctga aggagtcagg acctggcctg gtggcgccct cacagagcct gtccatcacc     120
tgcactgtct ctgggttttc attaagcagc tatggtgtac actgggttcg ccagcctcca     180
ggaaagggtc tggaatggct gggagtaata tgggctggtg aagcacaga ttataattcg      240 gctctcatgt ccagactgag catcagcaaa gacaactcca agagccaagt tgtcttaaaa     300
atgaacagcc tgcaaactga tgacacagcc atgtactact gtgccagaga agaggtctgg     360
gactggggcc aagggactct ggtcactgtc tctgca                                396

<210> SEQ ID NO 34
<211> LENGTH: 132
<212> TYPE: PRT
<213> ORGANISM: Mus musculus

<400> SEQUENCE: 34

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ser Ser Tyr Gly Val His Trp Val Arg Gln Pro Pro Gly Lys Gly Leu
    50                  55                  60

Glu Trp Leu Gly Val Ile Trp Ala Gly Gly Ser Thr Asp Tyr Asn Ser
65                  70                  75                  80

Ala Leu Met Ser Arg Leu Ser Ile Ser Lys Asp Asn Ser Lys Ser Gln
                85                  90                  95

Val Val Leu Lys Met Asn Ser Leu Gln Thr Asp Asp Thr Ala Met Tyr
                100                 105                 110

Tyr Cys Ala Arg Glu Glu Val Trp Asp Trp Gly Gln Gly Thr Leu Val
            115                 120                 125

Thr Val Ser Ala
    130

<210> SEQ ID NO 35
<211> LENGTH: 414
<212> TYPE: DNA
<213> ORGANISM: Mus musculus

<400> SEQUENCE: 35

```
atggaatgga gttggatatt tctctttctc ctgtcaggaa ctgcaggtgt ccactctgag    60
gtccagctgc agcagtctgg acctgagctg gtaaagcctg ggcttcagt gaagatgtcc    120
tgcaaggctt ctggatacac attcactagc tatattatgc actgggtgaa gcagaagcct    180
gggcagggcc ttgagtggat tggatatatt aatccttaca tgatggtac taagtacaat    240
gaaaagttca aggcaaggc cacactgact tcagacaaat cctccagcac agcctacatg    300
gagctcagca gcctgaccctc tgaggactct gcggtctatt actgtgcaaa ttactacggt    360
agtagctata ctatggacta ctggggtcaa ggaacctcag tcaccgtctc ctca         414
```

<210> SEQ ID NO 36
<211> LENGTH: 138
<212> TYPE: PRT
<213> ORGANISM: Mus musculus

<400> SEQUENCE: 36

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Ile Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Ser Tyr Thr Met Asp Tyr Trp
        115                 120                 125

Gly Gln Gly Thr Ser Val Thr Val Ser Ser
    130                 135
```

<210> SEQ ID NO 37
<211> LENGTH: 408
<212> TYPE: DNA
<213> ORGANISM: Mus musculus

<400> SEQUENCE: 37

```
atgggatgga gctggatctt tctctttctc ctgtcaggaa ctgcaggtgt cctctctgag    60
gtccagctgc aacaatctgg acctgagctg gtgaagcctg ggcttcagt gaagatatcc    120
tgtaaggctt ctggatacac gttcactgaa aactacatga actgggtgaa gcagagccat    180
ggaaagagcc ttgagtggat tggagatatt aatcgtaata tggtggtac tagatacaac    240
cagaagttca agggcaaggc cacattgact gtagacaagt cctccagcac agactacatg    300
gagctccgca gcctgacatc tgaggactct gcagtctatt actgtggggg cacggtagta    360
gggtacttcg atgtctgggg cacagggacc acggtcaccg tctcctca               408
```

<210> SEQ ID NO 38
<211> LENGTH: 136
<212> TYPE: PRT
<213> ORGANISM: Mus musculus

<400> SEQUENCE: 38

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Glu Asn Tyr Met Asn Trp Val Lys Gln Ser His Gly Lys Ser Leu
    50                  55                  60

Glu Trp Ile Gly Asp Ile Asn Arg Asn Asn Gly Gly Thr Arg Tyr Asn
65                  70                  75                  80

Gln Lys Phe Lys Gly Lys Ala Thr Leu Thr Val Asp Lys Ser Ser Ser
                85                  90                  95

Thr Asp Tyr Met Glu Leu Arg Ser Leu Thr Ser Glu Asp Ser Ala Val
            100                 105                 110

Tyr Tyr Cys Gly Gly Thr Val Val Gly Tyr Phe Asp Val Trp Gly Thr
        115                 120                 125

Gly Thr Thr Val Thr Val Ser Ser
    130                 135

<210> SEQ ID NO 39
<211> LENGTH: 414
<212> TYPE: DNA
<213> ORGANISM: Mus musculus

<400> SEQUENCE: 39
atggaatgga gttggatatt tctctttctc ctgtcaggaa ctgcaggtgt ccactctgag      60
gtccagctgc agcagtctgg acctgagctg gtaaagcctg ggcttcagt gaagatgtcc     120 tgcaaggctt ctggatacac attcactagc tatgttatgc actgggtgaa gcagaagcct    180
gggcagggcc ttgagtggat tggatatatt aatccttaca atgatggtac taagtacaat    240
gagaagttca aggcaaggc cacactgact tcagacaaat cctccagcac agcctacatg     300
gagctcagca gcctgacctc tgaggactct gcggtctatt actgtgcaaa ttactacggt    360
agtaactatg ctatggacta ctggggtcaa ggaacctcag tcaccgtctc ctca          414

<210> SEQ ID NO 40
<211> LENGTH: 138
<212> TYPE: PRT
<213> ORGANISM: Mus musculus

<400> SEQUENCE: 40

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

```
Glu Lys Phe Lys Gly Lys Ala Thr Leu Thr Ser Asp Lys Ser Ser
                85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Ser Val Thr Val Ser Ser
130                 135

<210> SEQ ID NO 41
<211> LENGTH: 396
<212> TYPE: DNA
<213> ORGANISM: Mus musculus

<400> SEQUENCE: 41
atgatgagtc ctgcccagtt cctgtttctg ttagtgctct ggattcggga aaccaacggt      60
gatgttgtga tgacccagac tccactcact ttgtcggtta ccattggtca accggcctcc    120
atctcttgca agtcaagtca gagcctctta gatagtgatg gaaagacata tttgaattgg    180
ttgttacaga ggccaggcca gtctccaaag cgcctaatct atctggtgtc taaactggac    240
tctggagtcc ctgacaggtt cactggcagt ggatcaggga cagatttcac actgaaaatc    300
agcagagtgg aggctgagga tttgggagtt tattattgct ggcaaggtac acatttcct     360 cggacgttcg gtggaggcac caagctggaa atcaaa                              396

<210> SEQ ID NO 42
<211> LENGTH: 132
<212> TYPE: PRT
<213> ORGANISM: Mus musculus

<400> SEQUENCE: 42

Met Met Ser Pro Ala Gln Phe Leu Phe Leu Val Leu Trp Ile Arg
1               5                   10                  15

Glu Thr Asn Gly Asp Val Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys
    130

<210> SEQ ID NO 43
<211> LENGTH: 396
<212> TYPE: DNA
<213> ORGANISM: Mus musculus

<400> SEQUENCE: 43
atgatgagtc ctgcccagtt cctgtttctg ttagtgctct ggattcggga aatcaacggt      60
```

```
gatgttgtga tgacccagac tccactcact tgtcggtta ccattggaca accagcctcc      120
atctcttgca agtcaagtca gagcctctta gatagtgatg aaagacata tttgaattgg      180 ttgttacaga ggccaggcca gtctccaaag cgcctaatct atctggtgtc taaactggac    240
tctggagtcc ctgacaggtt cactggcagt ggatcaggga cagatttcac actgaaaatc   300
agcagagtgg aggctgagga tttgggagtt tattattgct ggcaaggtac acattttcct   360
cggacgttcg gtggaggcac caagctggaa atcaaa                              396
```

<210> SEQ ID NO 44
<211> LENGTH: 132
<212> TYPE: PRT
<213> ORGANISM: Mus musculus

<400> SEQUENCE: 44

```
Met Met Ser Pro Ala Gln Phe Leu Phe Leu Leu Val Leu Trp Ile Arg
1               5                   10                  15

Glu Ile Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Arg Thr Phe Gly Gly Gly Thr Lys
        115                 120                 125

Leu Glu Ile Lys
    130
```

<210> SEQ ID NO 45
<211> LENGTH: 387
<212> TYPE: DNA
<213> ORGANISM: Mus musculus

<400> SEQUENCE: 45

```
atgatgtcct ctgctcagtt cctttggtctc ctgttgctct gttttcaagt cctaggtatc      60
agatgtgata tccagatgac acagactaca tcctccctgt ctgcctctct gggagacaga   120
gtcaccatca gttgcagggc aagtcaggac attagcaatt atttaaactg gtatcagcag    180
aaaccagatg gaactgttaa actcctgatc tactacacat caagattaca gtcaggagtc    240
ccatcaaggt tcagtggcag tgggtctgga acagattatt ctctcaccat tagcaacctg    300
gagcaagaag atattgccac ttactttgc caacaggta atacgcttcc tctcacgttc      360
ggtgctggga ccaagctgga gctgaaa                                         387
```

<210> SEQ ID NO 46
<211> LENGTH: 129
<212> TYPE: PRT
<213> ORGANISM: Mus musculus

<400> SEQUENCE: 46

```
Met Met Ser Ser Ala Gln Phe Leu Gly Leu Leu Leu Leu Cys Phe Gln
1               5                   10                  15
```

Val Leu Gly Ile Arg Cys Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Asn Tyr Leu Asn Trp Tyr Gln Gln Lys Pro Asp Gly
    50                  55                  60

Thr Val Lys Leu Leu Ile Tyr Tyr Thr Ser Arg Leu Gln Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Leu Thr Phe Gly Ala Gly Thr Lys Leu Glu Leu
        115                 120                 125

Lys

<210> SEQ ID NO 47
<211> LENGTH: 381
<212> TYPE: DNA
<213> ORGANISM: Mus musculus

<400> SEQUENCE: 47
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca gggcaagtca ggacattaga aattatttaa actggtatca gcagaaacca     180
gatggaagtg ttaaactcct gatctactac acatcaagat tacactcagg agtcccatca     240
aggttcagtg gcagtgggtc tggaacagat tattctctca ccattagcaa cctggagcaa     300
gaagatattg ccacttactt ttgccaacag gtaatacgc ttccgtggac gttcggtgga     360
ggcaccaagc tggaaatcaa a                                                381

<210> SEQ ID NO 48
<211> LENGTH: 127
<212> TYPE: PRT
<213> ORGANISM: Mus musculus

<400> SEQUENCE: 48

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Arg Asn Tyr Leu Asn Trp Tyr Gln Gln Lys Pro Asp Gly Ser Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys
        115                 120                 125

<210> SEQ ID NO 49
<211> LENGTH: 381
<212> TYPE: DNA
<213> ORGANISM: Mus musculus

<400> SEQUENCE: 49

```
atgatgtcct ctgctcagtt ccttggtctc ctgttgctct gttttcaagg taccagatgt     60
gatatccaga tgacacagat tataacctcc ctgtctgcct ctctgggaga cagagtcacc    120
atcagttgca ggtcaagtca ggacattagt aattatttaa attggtatca gcagaaacca    180
gatggaactg ttaaactcct gatctactac acatcaagat aaaatcagg agtcccatca     240
aggttcagtg gcagtgggtc tggaacagat tattctctca ccattagcaa cctggagcaa    300
gaagatattg ccacttactt ttgccaacag gtaatacgc ttccgtggac gttcggtgga     360
ggcaccaagc tggaaatcaa a                                              381
```

<210> SEQ ID NO 50
<211> LENGTH: 127
<212> TYPE: PRT
<213> ORGANISM: Mus musculus

<400> SEQUENCE: 50

Met Met Ser Ser Ala Gln Phe Leu Gly Leu Leu Leu Cys Phe Gln
1               5                   10                  15
Gly Thr Arg Cys Asp Ile Gln Met Thr Gln Ile Ile Thr Ser Leu Ser
            20                  25                  30
Ala Ser Leu Gly Asp Arg Val Thr Ile Ser Cys Arg Ser Ser Gln Asp
        35                  40                  45
Ile Ser Asn Tyr Leu Asn Trp Tyr Gln Gln Lys Pro Asp Gly Thr Val
    50                  55                  60
Lys Leu Leu Ile Tyr Tyr Thr Ser Arg Leu Lys Ser Gly Val Pro Ser
65                  70                  75                  80
Arg Phe Ser Gly Ser Gly Ser Gly Thr Asp Tyr Ser Leu Thr Ile Ser
                85                  90                  95
Asn Leu Glu Gln Glu Asp Ile Ala Thr Tyr Phe Cys Gln Gln Gly Asn
            100                 105                 110
Thr Leu Pro Trp Thr Phe Gly Gly Gly Thr Lys Leu Glu Ile Lys
        115                 120                 125

<210> SEQ ID NO 51
<211> LENGTH: 381
<212> TYPE: DNA
<213> ORGANISM: Mus musculus

<400> SEQUENCE: 51

```
atgatgtcct ctgctcagtt ccttggtctc ctgttgctct gttttcaagg taccagatgt     60
gatatccaga tgacacagac tacatcctcc ctgtctgcct ctctgggaga cagagtcacc    120
atcagttgca gggcaagtca ggacattagg aattatttaa actggtatca gcagaaacca    180
gacggaactg ttaaactcct gatctactac acatcaagat acactcagg agtcccatca     240
aggttcagtg gcagtgggtc tggaacagat tattctctca ccatcagcaa cctggagcaa    300
gaagatattg ccacttactt ttgccaacag ggtaatacgc ttccgtggac gttcggtgga    360
ggcaccaagc tggaaatcaa a                                              381
```

<210> SEQ ID NO 52
<211> LENGTH: 127
<212> TYPE: PRT

<213> ORGANISM: Mus musculus

<400> SEQUENCE: 52

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Arg Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys
        115                 120                 125

<210> SEQ ID NO 53
<211> LENGTH: 106
<212> TYPE: PRT
<213> ORGANISM: Homo sapiens

<400> SEQUENCE: 53

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 54
<211> LENGTH: 105
<212> TYPE: PRT
<213> ORGANISM: Homo sapiens

<400> SEQUENCE: 54

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
            85                  90                  95

Lys Thr Val Ala Pro Thr Glu Cys Ser
            100                 105

<210> SEQ ID NO 55
<211> LENGTH: 328
<212> TYPE: PRT
<213> ORGANISM: Homo sapiens

<400> SEQUENCE: 55

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Val
                85                  90                  95

Glu Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

```
<210> SEQ ID NO 56
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 56
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Gly Ser Asn Tyr Ala Met Asp Tyr Trp Gly Gln Gly
            100                 105                 110

Thr Leu Val Thr Val Ser Ser
        115

```
<210> SEQ ID NO 57
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 57
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Asn Tyr Ala Met Asp Tyr Trp Gly Gln Gly
            100                 105                 110

Thr Leu Val Thr Val Ser Ser
        115

```
<210> SEQ ID NO 58
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 58
```

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Asn Tyr Ala Met Asp Tyr Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 59

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Asn Tyr Ala Met Asp Tyr Trp Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
            50                  55                  60

Lys Gly Lys Ala Thr Leu Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Asn Tyr Ala Met Asp Tyr Trp Gly Gln Gly
                100                 105                 110

Thr Leu Val Thr Val Ser Ser
        115

<210> SEQ ID NO 61
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 61

Glu Val Gln Leu Val Gln Ser Gly Ala Glu Val Lys Lys Pro Gly Glu
 1               5                   10                  15

Ser Leu Lys Ile Ser Cys Lys Gly Ser Gly Tyr Thr Phe Thr Ser Tyr
                20                  25                  30

Val Met His Trp Val Arg Gln Met Pro Gly Lys Gly Leu Glu Trp Met
            35                  40                  45

Gly Tyr Ile Asn Pro Tyr Asn Asp Gly Thr Lys Tyr Asn Glu Lys Phe
            50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Tyr Tyr Gly Ser Asn Tyr Ala Met Asp Tyr Trp Gly Gln Gly
                100                 105                 110

Thr Met Val Thr Val Ser Ser
        115

<210> SEQ ID NO 62
<211> LENGTH: 119
<212> TYPE: PRT
<213> ORGANISM: Artificial
<220> FEATURE:
<223> OTHER INFORMATION: Heavy chain variable region of a humanized
      antibody that binds OX40

<400> SEQUENCE: 62

Glu Val Gln Leu Val Gln Ser Gly Ala Glu Val Lys Lys Pro Gly Glu
 1               5                   10                  15

Ser Val Lys Met Ser Cys Lys Gly Ser Gly Tyr Thr Phe Thr Ser Tyr
                20                  25                  30

Val Met His Trp Val Lys Gln Met Pro Gly Lys Gly Leu Glu Trp Ile
            35                  40                  45

Gly Tyr Ile Asn Pro Tyr Asn Asp Gly Thr Lys Tyr Asn Glu Lys Phe
            50                  55                  60

Lys Gly Gln Ala Thr Leu Ser Ser Asp Lys Ser Ile Ser Thr Ala Tyr
 65                  70                  75                  80

Met Gln Leu Ser Ser Leu Lys Ala Ser Asp Thr Ala Met Tyr Tyr Cys
                85                  90                  95

Ala Asn Tyr Tyr Gly Ser Asn Tyr Ala Met Asp Tyr Trp Gly Gln Gly
            100                 105                 110

Thr Met Val Thr Val Ser Ser
        115

<210> SEQ ID NO 63
<211> LENGTH: 105
<212> TYPE: PRT
<213> ORGANISM: Artificial
<220> FEATURE:
<223> OTHER INFORMATION: Light chain variable region of a humanized
      antibody that binds OX40

<400> SEQUENCE: 63

Gln Met Thr Gln Ser Pro Ser Ser Leu Ser Ala Ser Val Gly Asp Arg
1               5                   10                  15

Val Thr Ile Thr Cys Arg Ala Ser Gln Asp Ile Arg Asn Tyr Leu Asn
            20                  25                  30

Trp Tyr Gln Gln Lys Pro Gly Lys Ala Pro Lys Leu Leu Ile Tyr Tyr
        35                  40                  45

Thr Ser Arg Leu His Ser Gly Val Pro Ser Arg Phe Ser Gly Ser Gly
    50                  55                  60

Ser Gly Thr Asp Phe Thr Phe Thr Ile Ser Ser Leu Gln Pro Glu Asp
65                  70                  75                  80

Ile Ala Thr Tyr Tyr Cys Gln Gln Gly Asn Thr Leu Pro Trp Thr Phe
                85                  90                  95

Gly Gly Gly Thr Lys Leu Glu Ile Lys
            100                 105

<210> SEQ ID NO 64
<211> LENGTH: 105
<212> TYPE: PRT
<213> ORGANISM: Artificial
<220> FEATURE:
<223> OTHER INFORMATION: Light chain variable region of a humanized
      antibody that binds OX40

<400> SEQUENCE: 64

Gln Met Thr Gln Ser Pro Ser Ser Leu Ser Ala Ser Val Gly Asp Arg
1               5                   10                  15

Val Thr Ile Thr Cys Arg Ala Ser Gln Asp Ile Arg Asn Tyr Leu Asn
            20                  25                  30

Trp Tyr Gln Gln Lys Pro Gly Lys Ala Val Lys Leu Leu Ile Tyr Tyr
        35                  40                  45

Thr Ser Arg Leu His Ser Gly Val Pro Ser Arg Phe Ser Gly Ser Gly
    50                  55                  60

Ser Gly Thr Asp Phe Thr Phe Thr Ile Ser Ser Leu Gln Pro Glu Asp
65                  70                  75                  80

Ile Ala Thr Tyr Phe Cys Gln Gln Gly Asn Thr Leu Pro Trp Thr Phe
                85                  90                  95

Gly Gly Gly Thr Lys Leu Glu Ile Lys
            100                 105

<210> SEQ ID NO 65
<211> LENGTH: 105
<212> TYPE: PRT
<213> ORGANISM: Artificial
<220> FEATURE:
<223> OTHER INFORMATION: Light chain variable region of a humanized
      antibody that binds OX40

-continued

<400> SEQUENCE: 65

Gln Met Thr Gln Ser Pro Ser Ser Leu Ser Ala Ser Val Gly Asp Arg
1               5                   10                  15

Val Thr Ile Thr Cys Arg Ala Ser Gln Asp Ile Arg Asn Tyr Leu Asn
            20                  25                  30

Trp Tyr Gln Gln Lys Pro Gly Gly Ala Val Lys Leu Leu Ile Tyr Tyr
        35                  40                  45

Thr Ser Arg Leu His Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Ile Ala Thr Tyr Phe Cys Gln Gln Gly Asn Thr Leu Pro Trp Thr Phe
                85                  90                  95

Gly Gly Gly Thr Lys Leu Glu Ile Lys
            100                 105

<210> SEQ ID NO 66
<211> LENGTH: 107
<212> TYPE: PRT
<213> ORGANISM: Artificial
<220> FEATURE:
<223> OTHER INFORMATION: Light chain variable region of a humanized
      antibody that binds OX40

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 67
<211> LENGTH: 105
<212> TYPE: PRT
<213> ORGANISM: Artificial
<220> FEATURE:
<223> OTHER INFORMATION: Light chain variable region of a humanized
      antibody that binds OX40

<400> SEQUENCE: 67

Gln Met Thr Gln Ser Pro Ser Ser Leu Ser Ala Ser Val Gly Asp Arg
1               5                   10                  15

Val Thr Ile Ser Cys Arg Ala Ser Gln Asp Ile Arg Asn Tyr Leu Asn
            20                  25                  30

Trp Tyr Gln Gln Lys Pro Gly Lys Thr Val Lys Leu Leu Ile Tyr Tyr
        35                  40                  45

Thr Ser Arg Leu His Ser Gly Val Pro Ser Arg Phe Ser Gly Ser Gly
    50                  55                  60

```
Ser Gly Thr Asp Tyr Thr Phe Thr Ile Ser Ser Leu Gln Pro Glu Asp
 65                  70                  75                  80

Ile Ala Thr Tyr Phe Cys Gln Gln Gly Asn Thr Leu Pro Trp Thr Phe
                 85                  90                  95

Gly Gly Gly Thr Lys Leu Glu Ile Lys
            100                 105
```

<210> SEQ ID NO 68
<211> LENGTH: 107
<212> TYPE: PRT
<213> ORGANISM: Artificial
<220> FEATURE:
<223> OTHER INFORMATION: Light chain variable region of a humanized
      antibody that binds OX40

<400> SEQUENCE: 68

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Arg Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu His Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Asn Thr Leu Pro Trp
                 85                  90                  95

Thr Phe Gly Gln Gly Thr Lys Val Glu Ile Lys
            100                 105
```

<210> SEQ ID NO 69
<211> LENGTH: 107
<212> TYPE: PRT
<213> ORGANISM: Artificial
<220> FEATURE:
<223> OTHER INFORMATION: Light chain variable region of a humanized
      antibody that binds OX40

<400> SEQUENCE: 69

```
Glu Ile Val Met Thr Gln Ser Pro Ala Thr Leu Ser Ala Ser Pro Gly
1               5                   10                  15

Glu Arg Val Thr Leu Ser Cys Arg Ala Ser Gln Asp Ile Arg Asn Tyr
            20                  25                  30

Leu Asn Trp Tyr Gln Gln Lys Pro Gly Gly Ala Val Arg Leu Leu Ile
        35                  40                  45

Tyr Tyr Thr Ser Arg Leu His Ser Gly Val Pro Ala Arg Phe Ser Gly
 50                  55                  60

Ser Gly Ser Gly Thr Asp Tyr Thr Leu Thr Ile Ser Ser Leu Glu Pro
 65                  70                  75                  80

Glu Asp Tyr Ala Val Tyr Phe Cys Gln Gln Gly Asn Thr Leu Pro Trp
                 85                  90                  95

Thr Phe Gly Gln Gly Thr Lys Val Glu Ile Lys
            100                 105
```

<210> SEQ ID NO 70
<211> LENGTH: 357
<212> TYPE: DNA
<213> ORGANISM: Artificial
<220> FEATURE:

<223> OTHER INFORMATION: Heavy chain variable region of a humanized
     antibody that binds OX40

<400> SEQUENCE: 70
caggtgcagc tggtccagag cggagcagag gtgaagaaac ccggagcaag cgtgaaggtg    60
tcctgtaagg caagcggcta tactttcaca agctacgtga tgcactgggt caggcaggct   120
ccaggacagc gcctggagtg gatgggatac atcaacccct acaacgacgg aactaagtac   180
aacgaaaagt tcaaaggccg ggtgaccatt acaagagata cttctgccag taccgcttac   240
atggagctga gctccctgcg atctgaagac accgcagtct actattgcgc cagatattat   300
gggagcaact acgctatgga ttattggggg caggggactc tggtcactgt ctcttca      357

<210> SEQ ID NO 71
<211> LENGTH: 357
<212> TYPE: DNA
<213> ORGANISM: Artificial
<220> FEATURE:
<223> OTHER INFORMATION: Heavy chain variable region of a humanized
     antibody that binds OX40

<400> SEQUENCE: 71
caggtgcagc tggtgcagtc tggggccgaa gtgaagaaac ccggagcatc agtcaaagtc    60
agttgtaagg catcaggcta tacattcaca tcttacgtga tgcactgggt ccggcaggct   120
ccaggacaga gactggagtg gatcgggtac attaaccctt acaacgacgg aactaagtac   180
aacgaaaagt tcaaaggcag ggtgaccatc acatcagata cttctgccag taccgcttac   240
atggagctga gctccctgcg gagcgaagac accgcagtct actattgcgc caattattat   300
ggctcaaact acgctatgga ctattggggg caggggacac tggtgaccgt ctcctca      357

<210> SEQ ID NO 72
<211> LENGTH: 356
<212> TYPE: DNA
<213> ORGANISM: Artificial
<220> FEATURE:
<223> OTHER INFORMATION: Heavy chain variable region of a humanized
     antibody that binds OX40

<400> SEQUENCE: 72
aggtgcagct ggtccagagc ggagcagaag tcaagaaacc cggcgcaagt gtgaagatga    60
gttgtaaggc aagcggctat acattcacat cttacgtgat gcactgggtc aagcaggctc   120
caggacagag gctggagtgg atcgggtaca tcaaccctta caacgacgga actaagtaca   180
acgaaaagtt caaaggccgg gtgaccatca catcagatac ttctgccagt accgcttaca   240
tggagctgag ctccctgaga agcgaagaca ccgcagtcta ctattgcgcc aattattatg   300
gctctaacta tgctatggat tattggggc agggcactct ggtcaccgtg tcaagc        356

<210> SEQ ID NO 73
<211> LENGTH: 356
<212> TYPE: DNA
<213> ORGANISM: Artificial
<220> FEATURE:
<223> OTHER INFORMATION: Heavy chain variable region of a humanized
     antibody that binds OX40

<400> SEQUENCE: 73
aggtgcagct ggtccagagc ggagcagagg tgaagaaacc cggagcatca gtcaaaatgt    60
cctgtaaggc aagcggctat actttcacat cttacgtgat gcactgggtc aagcaggctc   120
caggacagag gctggagtgg atcgggtaca tcaaccctta caacgacgga actaagtaca   180

```
acgaaaagtt caaaggccgg gccaccctga catcagatac ttctgccagt accgcttaca    240
tggagctgag ctccctgaga agcgaagaca ccgcagtgta ctattgcgcc aattattatg    300
ggtcaaacta cgctatggac tattgggggc agggcactct ggtcactgtc agcagc       356
```

<210> SEQ ID NO 74
<211> LENGTH: 356
<212> TYPE: DNA
<213> ORGANISM: Artificial
<220> FEATURE:
<223> OTHER INFORMATION: Heavy chain variable region of a humanized
      antibody that binds OX40

<400> SEQUENCE: 74

```
aggtgcagct ggtccagagc ggagcagagg tgaagaaacc cggagcatca gtcaaaatgt    60
cctgtaaggc aagcggctat actttcacat cttacgtgat gcactggtc aagcaggctc    120 caggacagag gctggagtgg atcgggtaca tcaaccctta caacgacgga actaagtaca    180
acgaaaagtt caaaggccgg gccaccctga catcagatac ttctgccagt accgcttaca    240
tggagctgag ctccctgaga agcgaagaca ccgcagtgta ctattgcgcc aattattatg    300
ggtcaaacta cgctatggac tattgggggc agggcactct ggtcactgtc agcagc       356
```

<210> SEQ ID NO 75
<211> LENGTH: 357
<212> TYPE: DNA
<213> ORGANISM: Artificial
<220> FEATURE:
<223> OTHER INFORMATION: Heavy chain variable region of a humanized
      antibody that binds OX40

<400> SEQUENCE: 75

```
gaagtgcagc tggtgcagag cggggcagaa gtgaagaagc tggggaaag cctgaagatt    60 agttgtaaag ggagcggata tacattcact tcttacgtga tgcactgggt ccggcagatg    120
ccaggcaagg gactggagtg gatgggatac atcaacccctt ataatgacgg caccaaatat    180
aacgaaaagt tcaaagggca ggtgaccatc tcagcagaca agtctattag tacagcctac    240
ctgcagtgga gctccctgaa agccagcgac acagctatgt actattgcgc tagatattat    300
ggctcaaact acgctatgga ctactgggga caggggacta tggtcaccgt ctcaagc       357
```

<210> SEQ ID NO 76
<211> LENGTH: 357
<212> TYPE: DNA
<213> ORGANISM: Artificial
<220> FEATURE:
<223> OTHER INFORMATION: Heavy chain variable region of a humanized
      antibody that binds OX40

<400> SEQUENCE: 76

```
gaggtccagc tggtgcagag cggagcagag gtcaagaagc ccggcgaatc agtgaagatg    60
tcctgtaagg gaagcggata tactttcact tcctacgtga tgcactgggt caagcagatg    120
cccggcaaag gctggagtg gatcggatac attaacccctt ataatgacgg caccaagtat    180
aacgaaaagt tcaaagggca ggcaaccctg agctccgata agtcaatcag cacagcctac    240
atgcagctgt ctagtctgaa agccagtgac acagctatgt actattgcgc taattattat    300
gggtcaaact acgcaatgga ttactgggggg cagggaacaa tggtcactgt ctcttca      357
```

<210> SEQ ID NO 77
<211> LENGTH: 321

```
<212> TYPE: DNA
<213> ORGANISM: Artificial
<220> FEATURE:
<223> OTHER INFORMATION: Light chain variable region of a humanized
      antibody that binds OX40

<400> SEQUENCE: 77
gacattcaga tgacccagag cccttccagc ctgagtgcca gcgtcggaga tagagtgaca      60
attacttgcc gcgccagcca ggacattagg aactacctga attggtatca gcagaagccc     120
ggcaaagccc ctaagctgct gatctactat acaagccggc tgcactccgg ggtgccaagt     180
agattctctg gcagtgggtc aggaactgac ttcaccttta caatcagctc cctgcagccc     240
gaggatattg ctacctacta ttgtcagcag ggaaatacac tgccttggac cttcggcggg     300
gggactaaac tggaaatcaa a                                                321

<210> SEQ ID NO 78
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 78
gacattcaga tgacccagag cccttccagc ctgagcgcca gcgtcggaga cagagtgact      60
attacttgta gagccagcca ggacattagg aactacctga attggtatca gcagaagccc     120
ggcaaagccg tgaagctgct gatctactat acaagccggc tgcactccgg ggtccctagt     180
agattctctg gcagtgggtc aggaactgac ttcaccttta caatcagctc cctgcagccc     240
gaggatattg ctacctactt ttgtcagcag ggaaatacac tgccttggac cttcggaggg     300
gggactaaac tggaaatcaa a                                                321

<210> SEQ ID NO 79
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 79
gatattcaga tgacccagtc accttccagt ctgagtgcca gcgtcgggga tagagtcacc      60
attacttgcc gcgccagcca ggacattagg aactacctga attggtatca gcagaagccc     120
ggcggggccg tgaaactgct gatctactat acaagccggc tgcactccgg cgtccctagt     180
agattctctg gaagtggctc agggactgac tttaccctga caatcagctc cctgcagccc     240
gaggatattg ctacctactt ctgtcagcag ggaaatacac tgccttggac cttcggaggg     300
gggactaaac tggaaatcaa a                                                321

<210> SEQ ID NO 80
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 80
gacattcaga tgacccagag ccccagcagc ctgagcgcca gcgtcggaga tagagtgacc      60
```

```
attacttgta gagccagcca ggacattagg aactacctga attggtatca gcagaagccc    120
ggcggggccg tgaaactgct gatctactat acaagccggc tgcactccgg cgtccctagt    180
agattctctg gaagtggctc agggactgac tacaccctga caatcagctc cctgcagccc    240
gaggatattg ctacctattt ttgtcagcag ggaaatactc tgccttggac cttcggcgga    300
gggactaaac tggaaatcaa a                                              321

<210> SEQ ID NO 81
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 81
gacattcaga tgacccagag cccttccagc ctgagtgctt ccgtcgggga tagagtgaca     60
attagttgca gagccagcca ggacattagg aactacctga attggtatca gcagaagccc    120
ggcaaaactg tgaagctgct gatctactat accagccggc tgcactccgg ggtccctagt    180
agattctctg gcagtgggtc aggaacagac tacacccttta caatcagctc cctgcagccc   240
gaggatattg ccacctatttt ctgtcagcag ggaaatactc tgccttggac cttcggcggc   300
ggaactaaac tggaaatcaa a                                              321

<210> SEQ ID NO 82
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 82
gaaatcgtgc tgacccagtc ccccgccaca ctgagtctgt cccccggaga aagagccacc     60
ctgagctgta gggcaagcca ggatattcgg aactacctga attggtatca gcagaagcca    120
ggacaggcac ctcgactgct gatctactat actagcagac tgcactctgg gattccagct    180
aggttctctg gcagtgggtc aggaaccgac tttaccctga caatcagctc cctggagccc    240
gaagatttcg ccgtgtacta ttgccagcag gggaatactc tgccttggac cttcggccag    300
gggactaaag tggaaatcaa a                                              321

<210> SEQ ID NO 83
<211> LENGTH: 321
<212> TYPE: DNA
<213> ORGANISM: Artificial
<220> FEATURE:
<223> OTHER INFORMATION: Light chain variable region of a humanized
      antibody that binds OX40

<400> SEQUENCE: 83
gaaatcgtga tgacccagag cccagccaca ctgtccgcca gcccaggcga gagagtcaca     60
ctgtcttgcc gagccagcca ggatattcgg aactacctga attggtatca gcagaagcca    120
ggaggagccg tgcggctgct gatctactat actagcagac tgcactctgg cgtccctgct    180
aggttctctg gaagtggctc agggaccgac tacaccctga caattagctc cctggagccc    240
gaagattacg ccgtgtatttt ttgccagcag ggaaatactc tgccttggac attcggacag    300
gggactaaag tggaaatcaa a                                              321
```

-continued

```
<210> SEQ ID NO 84
<211> LENGTH: 468
<212> TYPE: PRT
<213> ORGANISM: Artificial
<220> FEATURE:
<223> OTHER INFORMATION: Heavy chain of a chimeric antibody that binds
      OX40 - 19 aa leader sequence

<400> SEQUENCE: 84

Met Gly Trp Ser Trp Ile Leu Leu Phe Leu Leu Ser Val Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Ser Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 85
<211> LENGTH: 233
<212> TYPE: PRT
<213> ORGANISM: Artificial
<220> FEATURE:
<223> OTHER INFORMATION: Light chain of a chimeric antibody that binds
      OX40 - 19 aa leader sequence

<400> SEQUENCE: 85

Met Gly Trp Ser Trp Ile Leu Leu Phe Leu Leu Ser Val Thr Ala Gly
1               5                   10                  15

Val His Ser Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Arg Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 86
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 86

```
Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Arg Gln Ala Pro Gly Gln Arg Leu
    50                  55                  60

Glu Trp Met Gly Tyr Ile Asn Pro Tyr Asn Asp Gly Thr Lys Tyr Asn
65                  70                  75                  80

Glu Lys Phe Lys Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Tyr Tyr Gly Ser Asn Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 87
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 87

Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Arg Gln Ala Pro Gly Gln Arg Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Arg Val Thr Ile Thr Ser Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255
```

```
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 88
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 88

Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Ala Pro Gly Gln Arg Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Arg Val Thr Ile Thr Ser Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Leu Val Thr Val Ser Ser Ala Ser Thr Lys Gly Pro
```

```
              130                 135                 140
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 89
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 89

Met Gly Trp Ser Trp Ile Leu Leu Phe Leu Leu Ser Val Thr Ala Gly
1               5                   10                  15
```

-continued

Val His Ser Gln Val Gln Leu Val Gln Ser Gly Ala Glu Val Lys Lys
          20                  25                  30

Pro Gly Ala Ser Val Lys Met Ser Cys Lys Ala Ser Gly Tyr Thr Phe
          35                  40                  45

Thr Ser Tyr Val Met His Trp Val Lys Gln Ala Pro Gly Gln Arg Leu
     50                  55                  60

Glu Trp Ile Gly Tyr Ile Asn Pro Tyr Asn Asp Gly Thr Lys Tyr Asn
65                  70                  75                  80

Glu Lys Phe Lys Gly Arg Ala Thr Leu Thr Ser Asp Thr Ser Ala Ser
              85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val

```
                435              440              445
Met His Glu Ala Leu His Asn His Tyr Thr Gln Lys Ser Leu Ser Leu
    450              455              460

Ser Pro Gly Lys
465

<210> SEQ ID NO 90
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 90

Met Gly Trp Ser Trp Ile Leu Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Met His Trp Val Lys Gln Ala Pro Gly Gln Arg Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Asn Tyr Tyr Gly Ser Asn Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320
```

```
Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465

<210> SEQ ID NO 91
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 91

Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Thr Phe
        35                  40                  45

Thr Ser Tyr Val Met His Trp Val Arg Gln Met Pro Gly Lys Gly Leu
    50                  55                  60

Glu Trp Met Gly Tyr Ile Asn Pro Tyr Asn Asp Gly Thr Lys Tyr Asn
65                  70                  75                  80

Glu Lys Phe Lys Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Tyr Tyr Gly Ser Asn Tyr Ala Met Asp Tyr Trp
        115                 120                 125

Gly Gln Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

-continued

Val Pro Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 92
<211> LENGTH: 468
<212> TYPE: PRT
<213> ORGANISM: Artificial
<220> FEATURE:
<223> OTHER INFORMATION: Heavy chain of a humanized antibody that binds
      OX40 - 19 aa leader sequence

<400> SEQUENCE: 92

Met Gly Trp Ser Trp Ile Leu Leu Phe Leu Leu Ser Val Thr Ala Gly
1               5                   10                  15

Val His Ser Glu Val Gln Leu Val Gln Ser Gly Ala Glu Val Lys Lys
            20                  25                  30

Pro Gly Glu Ser Val Lys Met Ser Cys Lys Gly Ser Gly Tyr Thr Phe
        35                  40                  45

Thr Ser Tyr Val Met His Trp Val Lys Gln Met Pro Gly Lys Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Gln Ala Thr Leu Ser Ser Asp Lys Ser Ile Ser

```
                        85                  90                  95

Thr Ala Tyr Met Gln Leu Ser Ser Leu Lys Ala Ser Asp Thr Ala Met
                100                 105                 110

Tyr Tyr Cys Ala Asn Tyr Tyr Gly Ser Asn Tyr Ala Met Asp Tyr Trp
                115                 120                 125

Gly Gln Gly Thr Met Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 93
<211> LENGTH: 233
<212> TYPE: PRT
<213> ORGANISM: Artificial
```

<220> FEATURE:
<223> OTHER INFORMATION: Light chain of a humanized antibody that binds
      OX40 - 19 aa leader sequence

<400> SEQUENCE: 93

Met Gly Trp Ser Trp Ile Leu Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Arg Asn Tyr Leu Asn Trp Tyr Gln Gln Lys Pro Gly Lys Ala Pro Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 94
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 94

Met Gly Trp Ser Trp Ile Leu Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Arg Asn Tyr Leu Asn Trp Tyr Gln Gln Lys Pro Gly Lys Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
                215                 220

Thr Lys Ser Phe Asn Arg Gly Glu Cys
225                 230

<210> SEQ ID NO 95
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 95

Met Gly Trp Ser Trp Ile Leu Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Arg Asn Tyr Leu Asn Trp Tyr Gln Gln Lys Pro Gly Gly Ala Val Lys
50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val

```
        210                 215                 220
Thr Lys Ser Phe Asn Arg Gly Glu Cys
225                 230

<210> SEQ ID NO 96
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 96

Met Gly Trp Ser Trp Ile Leu Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Arg Asn Tyr Leu Asn Trp Tyr Gln Gln Lys Pro Gly Ala Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Thr Leu Thr Ile Ser Ser
                85                  90                  95

Leu Gln Pro Glu Asp Ile Ala Thr Tyr Phe Cys Gln Gln Gly Asn Thr
            100                 105                 110

Leu Pro Trp Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 97
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 97

Met Gly Trp Ser Trp Ile Leu Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Ser Cys Arg Ala Ser Gln Asp Ile
```

```
                35                  40                  45
Arg Asn Tyr Leu Asn Trp Tyr Gln Gln Lys Pro Gly Lys Thr Val Lys
 50                  55                  60
Leu Leu Ile Tyr Tyr Thr Ser Arg Leu His Ser Gly Val Pro Ser Arg
 65                  70                  75                  80
Phe Ser Gly Ser Gly Ser Gly Thr Asp Tyr Thr Phe Thr Ile Ser Ser
                 85                  90                  95
Leu Gln Pro Glu Asp Ile Ala Thr Tyr Phe Cys Gln Gln Gly Asn Thr
            100                 105                 110
Leu Pro Trp Thr Phe Gly Gly Gly Thr Lys Leu Glu Ile Lys Arg Thr
            115                 120                 125
Val Ala Ala Pro Ser Val Phe Ile Phe Pro Pro Ser Asp Glu Gln Leu
            130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
            195                 200                 205
Lys Val Tyr Ala Cys Glu Val Thr His Gln Gly Leu Ser Ser Pro Val
210                 215                 220
Thr Lys Ser Phe Asn Arg Gly Glu Cys
225                 230

<210> SEQ ID NO 98
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 98

Met Gly Trp Ser Trp Ile Leu Leu Phe Leu Leu Ser Val Thr Ala Gly
  1               5                  10                  15
Val His Ser Glu Ile Val Leu Thr Gln Ser Pro Ala Thr Leu Ser Leu
             20                  25                  30
Ser Pro Gly Glu Arg Ala Thr Leu Ser Cys Arg Ala Ser Gln Asp Ile
             35                  40                  45
Arg Asn Tyr Leu Asn Trp Tyr Gln Gln Lys Pro Gly Gln Ala Pro Arg
 50                  55                  60
Leu Leu Ile Tyr Tyr Thr Ser Arg Leu His Ser Gly Ile Pro Ala Arg
 65                  70                  75                  80
Phe Ser Gly Ser Gly Ser Gly Thr Asp Phe Thr Leu Thr Ile Ser Ser
                 85                  90                  95
Leu Glu Pro Glu Asp Phe Ala Val Tyr Tyr Cys Gln Gln Gly Asn Thr
            100                 105                 110
Leu Pro Trp Thr Phe Gly Gln Gly Thr Lys Val Glu Ile Lys Arg Thr
            115                 120                 125
Val Ala Ala Pro Ser Val Phe Ile Phe Pro Pro Ser Asp Glu Gln Leu
            130                 135                 140
Lys Ser Gly Thr Ala Ser Val Val Cys Leu Leu Asn Asn Phe Tyr Pro
145                 150                 155                 160
```

```
Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
        180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 99
<211> LENGTH: 233
<212> TYPE: PRT
<213> ORGANISM: Artificial
<220> FEATURE:
<223> OTHER INFORMATION: Light chain of a humanized antibody that binds
      OX40 - 19 aa leader sequence

<400> SEQUENCE: 99

Met Gly Trp Ser Trp Ile Leu Leu Phe Leu Leu Ser Val Thr Ala Gly
1               5                   10                  15

Val His Ser Glu Ile Val Met Thr Gln Ser Pro Ala Thr Leu Ser Ala
            20                  25                  30

Ser Pro Gly Glu Arg Val Thr Leu Ser Cys Arg Ala Ser Gln Asp Ile
        35                  40                  45

Arg Asn Tyr Leu Asn Trp Tyr Gln Gln Lys Pro Gly Gly Ala Val Arg
    50                  55                  60

Leu Leu Ile Tyr Tyr Thr Ser Arg Leu His Ser Gly Val Pro Ala Arg
65                  70                  75                  80

Phe Ser Gly Ser Gly Ser Gly Thr Asp Tyr Thr Leu Thr Ile Ser Ser
                85                  90                  95

Leu Glu Pro Glu Asp Tyr Ala Val Tyr Phe Cys Gln Gln Gly Asn Thr
            100                 105                 110

Leu Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
        180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 100
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence
```

<400> SEQUENCE: 100

```
atgggctgga gctggatcct gctgttcctc ctgagcgtga cagcaggagt gcacagccag    60
gtgcagctgg tccagagcgg agcagaggtg aagaaacccg agcaagcgt gaaggtgtcc   120
tgtaaggcaa gcggctatac tttcacaagc tacgtgatgc actgggtcag gcaggctcca   180
ggacagcgcc tggagtggat gggatacatc aaccttaca cgacggaac taagtacaac   240
gaaaagttca aggccgggt gaccattaca agagatactt ctgccagtac cgcttacatg   300
gagctgagct ccctgcgatc tgaagacacc gcagtctact attgcgccag atattatggg   360
agcaactacg ctatggatta ttgggggcag gggactctgg tcactgtctc ttcagctagc   420
accaagggcc catcggtctt ccccctggca ccctcctcca gagcacctc tggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca gaaagttga gcccaaatct   720
tgtgacaaaa ctcacacatg cccaccgtgc ccagcacctg aactcctggg gggaccgtca   780
gtcttcctct ccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca agccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaatga                                      1407
```

<210> SEQ ID NO 101
<211> LENGTH: 1407
<212> TYPE: DNA
<213> ORGANISM: Artificial
<220> FEATURE:
<223> OTHER INFORMATION: Heavy chain of a humanized antibody that binds OX40 - 19 aa leader sequence

<400> SEQUENCE: 101

```
atgggctgga gctggatcct gctgttcctc ctgagcgtga cagcaggagt gcacagccag    60
gtgcagctgg tgcagtctgg ggccgaagtg aagaaacccg agcatcagt caaagtcagt   120
tgtaaggcat caggctatac attcacatct tacgtgatgc actgggtccg gcaggctcca   180
ggacagagac tggagtggat cgggtacatt aaccttaca cgacggaac taagtacaac   240
gaaaagttca aggcagggt gaccatcaca tcagatactt ctgccagtac cgcttacatg   300
gagctgagct ccctgcggag cgaagacacc gcagtctact attgcgccaa ttattatggc   360
tcaaactacg ctatggacta ttgggggcag gggacactgg tgaccgtctc ctcagctagc   420
accaagggcc catcggtctt ccccctggca ccctcctcca gagcacctc tggggcaca   480
gcggccctgg gctgcctggt caaggactac ttccccgaac cggtgacggt gtcgtggaac   540
```

```
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660 tgcaacgtga atcacaagcc cagcaacacc aaggtggaca gaaagttga gcccaaatct    720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                      1407
```

<210> SEQ ID NO 102
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence

<400> SEQUENCE: 102

```
atgggctgga gctggatcct gctgttcctc ctgagcgtga cagcaggagt gcacagccag     60
gtgcagctgg tccagagcgg agcagaagtc aagaaacccg gcgcaagtgt gaagatgagt    120
tgtaaggcaa gcggctatac attcacatct acgtgatgc actgggtcaa gcaggctcca    180
ggacagaggc tggagtggat cgggtacatc aaccccttaca acgacggaac taagtacaac    240
gaaaagttca aggccgggt gaccatcaca tcagatactt ctgccagtac cgcttacatg    300
gagctgagct ccctgagaag cgaagacacc gcagtctact attgcgccaa ttattatggc    360
tctaactatg ctatggatta ttggggggcag ggcactctgg tcaccgtgtc aagcgctagc    420
accaagggcc catcggtctt ccccctggca ccctcctcca agagcacctc tggggggcaca    480 gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660 tgcaacgtga atcacaagcc cagcaacacc aaggtggaca gaaagttga gcccaaatct    720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca agccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
```

-continued

```
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407
```

<210> SEQ ID NO 103
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence

<400> SEQUENCE: 103

```
atgggctgga gctggatcct gctgttcctc ctgagcgtga cagcaggagt gcacagccag     60
gtgcagctgg tccagagcgg agcagaggtg aagaaacccg gagcatcagt caaaatgtcc    120
tgtaaggcaa gcggctatac tttcacatct tacgtgatgc actgggtcaa gcaggctcca    180
ggacagaggc tggagtggat cgggtacatc aacccttaca cgacggaac taagtacaac     240 gaaaagttca aggccgggc accctgaca tcagatactt ctgccagtac cgcttacatg      300
gagctgagct ccctgagaag cgaagacacc gcagtgtact attgcgccaa ttattatggg    360
tcaaactacg ctatggacta ttgggggcag ggcactctgg tcactgtcag cagcgctagc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttccccggctg tcctacagtc ctcaggactc    600
tactccctca gcagcgtggt gaccgtgccc tccagcagct gggcaccca gacctacatc     660 tgcaacgtga atcacaagcc cagcaacacc aaggtggaca gaaagttga gcccaaatct    720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc ccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag    1380
agcctctccc tgtctccggg taaatga                                        1407
```

<210> SEQ ID NO 104
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence

<400> SEQUENCE: 104

```
atgggctgga gctggatcct gctgttcctc ctgagcgtga cagcaggagt gcacagccag      60
gtccagctgg tgcagagcgg agcagaggtg aagaaacccg gcgcaagcgt caaggtgtcc     120
tgtaaggcaa gcggctatac ttttacatct tacgtgatgc actgggtcaa acaggctcca     180
ggacagcggc tggagtggat cggatacatt aacccttaca cgacggaac taagtacaac      240
gaaaagttca aggcaaggc caccctgaca tcagatactt ctgccagtac cgcttacatg      300
gagctgagct ccctgagaag cgaagacacc gcagtgtact attgcgccaa ttattatggc     360
tcaaactatg ctatggatta ttgggggcag ggaacactgg tcaccgtctc atcagctagc     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcaccca gacctacatc      660
tgcaacgtga atcacaagcc cagcaacacc aaggtggaca agaaagttga gcccaaatct     720
tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca agccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                          1407
```

<210> SEQ ID NO 105
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence

<400> SEQUENCE: 105

```
atgggctgga gctggatcct gctgttcctc ctgagcgtga cagcaggagt gcacagcgaa      60
gtgcagctgg tgcagagcgg ggcagaagtg aagaagcctg gggaaagcct gaagattagt     120
tgtaaaggga gcggatatac attcacttct tacgtgatgc actgggtccg gcagatgcca     180
ggcaagggac tggagtggat gggatacatc aacccttata tgacggcac caaatataac      240
gaaaagttca agggcaggt gaccatctca gcagacaagt ctattagtac agcctacctg     300
cagtggagct ccctgaaagc cagcgacaca gctatgtact attgcgctag atattatggc     360
tcaaactacg ctatggacta ctggggacag gggactatgg tcaccgtctc aagcgctagc     420
accaagggcc catcggtctt ccccctggca ccctcctcca agagcacctc tgggggcaca     480
gcggccctgg gctgcctggt caaggactac ttccccgaac cggtgacggt gtcgtggaac     540
```

-continued

```
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca agaaagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta acagcacg    960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaatga                                      1407
```

<210> SEQ ID NO 106
<211> LENGTH: 1407
<212> TYPE: DNA
<213> ORGANISM: Artificial
<220> FEATURE:
<223> OTHER INFORMATION: Heavy chain of a humanized antibody that binds
      OX40 - 19 aa leader sequence

<400> SEQUENCE: 106

```
atgggctgga gctggatcct gctgttcctc ctgagcgtga cagcaggagt gcacagcgag   60
gtccagctgg tgcagagcgg agcagaggtc aagaagcccg gcgaatcagt gaagatgtcc  120
tgtaagggaa gcggatatac tttcacttcc tacgtgatgc actgggtcaa gcagatgccc  180
ggcaaagggc tggagtggat cggatacatt aaccttata atgacggcac caagtataac   240
gaaaagttca agggcaggc aaccctgagc tccgataagt caatcagcac agcctacatg   300
cagctgtcta gtctgaaagc cagtgacaca gctatgtact attgcgctaa ttattatggg  360
tcaaactacg caatggatta ctgggggcag ggaacaatgg tcactgtctc ttcagctagc  420
accaagggcc catcggtctt ccccctggca ccctcctcca gagcacctc tgggggcaca  480
gcggccctgg gctgcctggt caaggactac ttccccgaac cggtgacggt gtcgtggaac  540
tcaggcgccc tgaccagcgg cgtgcacacc ttcccggctg tcctacagtc ctcaggactc  600
tactccctca gcagcgtggt gaccgtgccc tccagcagct gggcaccca gacctacatc   660
tgcaacgtga atcacaagcc cagcaacacc aaggtggaca agaaagttga gcccaaatct  720
tgtgacaaaa ctcacacatg cccaccgtgc ccagcacctg aactcctggg gggaccgtca  780
gtcttcctct tccccccaaa acccaaggac accctcatga tctcccggac ccctgaggtc  840
acatgcgtgg tggtggacgt gagccacgaa gaccctgagg tcaagttcaa ctggtacgtg  900
gacggcgtgg aggtgcataa tgccaagaca aagccgcggg aggagcagta acagcacg   960
taccgtgtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc cccgagaacc acaggtgtac accctgcccc catcccggga tgagctgacc 1140
```

```
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407
```

<210> SEQ ID NO 107
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 107

```
atgggctgga gctggatcct gctgttcctc ctgagcgtga cagcaggagt gcacagcgac     60
attcagatga cccagagccc ttccagcctg agtgccagcg tcggagatag agtgacaatt    120
acttgccgcg ccagccagga cattaggaac tacctgaatt ggtatcagca gaagcccggc    180
aaagccccta gctgctgat ctactataca gccggctgc actccggggt gccaagtaga     240
ttctctggca gtgggtcagg aactgacttc acctttacaa tcagctccct gcagcccgag    300
gatattgcta cctactattg tcagcaggga aatacactgc cttggacctt cggcggggga    360
actaaactgg aaatcaaacg aacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                       702
```

<210> SEQ ID NO 108
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 108

```
atgggctgga gctggatcct gctgttcctc ctgagcgtga cagcaggagt gcacagcgac     60
attcagatga cccagagccc ttccagcctg agcgccagcg tcggagacag agtgactatt    120
acttgtagag ccagccagga cattaggaac tacctgaatt ggtatcagca gaagcccggc    180
aaagccgtga agctgctgat ctactataca gccggctgc actccggggt ccctagtaga     240
ttctctggca gtgggtcagg aactgacttc acctttacaa tcagctccct gcagcccgag    300
gatattgcta cctactttttg tcagcaggga aatacactgc cttggacctt cggaggggga   360
actaaactgg aaatcaaacg aacggtggct gcaccatctg tcttcatctt cccgccatct    420
gatgagcagt tgaaatctgg aactgcctct gttgtgtgcc tgctgaataa cttctatccc    480
agagaggcca agtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                       702
```

<210> SEQ ID NO 109
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 109

```
atgggctgga gctggatcct gctgttcctc ctgagcgtga cagcaggagt gcacagcgat    60
attcagatga cccagtcacc ttccagtctg agtgccagcg tcggggatag agtcaccatt   120
acttgccgcg ccagccagga cattaggaac tacctgaatt ggtatcagca gaagcccggc   180
ggggccgtga aactgctgat ctactataca agccggctgc actccggcgt ccctagtaga   240
ttctctggaa gtggctcagg gactgacttt accctgacaa tcagctccct gcagcccgag   300
gatattgcta cctacttctg tcagcaggga aatacactgc cttggacctt cggagggggg   360
actaaactgg aaatcaaacg aacggtggct gcaccatctg tcttcatctt cccgccatct   420
gatgagcagt tgaaatctgg aactgcctct gttgtgtgcc tgctgaataa cttctatccc   480
agagaggcca aagtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ag                      702
```

<210> SEQ ID NO 110
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 110

```
atgggctgga gctggatcct gctgttcctc ctgagcgtga cagcaggagt gcacagcgac    60
attcagatga cccagagccc cagcagcctg agcgccagcg tcggagatag agtgaccatt   120
acttgtagag ccagccagga cattaggaac tacctgaatt ggtatcagca gaagcccggc   180
ggggccgtga aactgctgat ctactataca agccggctgc actccggcgt ccctagtaga   240
ttctctggaa gtggctcagg gactgactac accctgacaa tcagctccct gcagcccgag   300
gatattgcta cctattttg tcagcaggga atactctgc cttggacctt cggcggaggg   360
actaaactgg aaatcaaacg aacggtggct gcaccatctg tcttcatctt cccgccatct   420
gatgagcagt tgaaatctgg aactgcctct gttgtgtgcc tgctgaataa cttctatccc   480
agagaggcca aagtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ag                      702
```

<210> SEQ ID NO 111
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 111

```
atgggctgga gctggatcct gctgttcctc ctgagcgtga cagcaggagt gcacagcgac    60
attcagatga cccagagccc ttccagcctg agtgcttccg tcggggatag agtgacaatt   120
agttgcagag ccagccagga cattaggaac tacctgaatt ggtatcagca gaagcccggc   180
aaaactgtga agctgctgat ctactatacc agccggctgc actccggggt ccctagtaga   240
ttctctggca gtgggtcagg aacagactac acctttacaa tcagctccct gcagcccgag   300
gatattgcca cctatttctg tcagcaggga atactctgc cttggacctt cggcggcgga   360
actaaactgg aaatcaaacg aacggtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ag                      702
```

<210> SEQ ID NO 112
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 112

```
atgggctgga gctggatcct gctgttcctc ctgagcgtga cagcaggagt gcacagcgaa    60
atcgtgctga cccagtcccc cgccacactg agtctgtccc ccggagaaag agccaccctg   120
agctgtaggg caagccagga tattcggaac tacctgaatt ggtatcagca gaagccagga   180
caggcacctc gactgctgat ctactatact agcagactgc actctgggat tccagctagg   240
ttctctggca gtgggtcagg aaccgacttt accctgacaa tcagctccct ggagcccgaa   300
gatttcgccg tgtactattg ccagcagggg aatactctgc cttggacctt cggccagggg   360
actaaagtgg aaatcaaacg aacggtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ag                      702
```

<210> SEQ ID NO 113
<211> LENGTH: 702
<212> TYPE: DNA
<213> ORGANISM: Artificial
<220> FEATURE:
<223> OTHER INFORMATION: Light chain of a humanized antibody that binds
      OX40 - 19 aa leader sequence

<400> SEQUENCE: 113

```
atgggctgga gctggatcct gctgttcctc ctgagcgtga cagcaggagt gcacagcgaa    60
atcgtgatga cccagagccc agccacactg tccgccagcc aggcgagag agtcacactg   120
tcttgccgag ccagccagga tattcggaac tacctgaatt ggtatcagca gaagccagga   180
```

-continued

| | | | | |
|---|---|---|---|---|
| ggagccgtgc | ggctgctgat | ctactatact | agcagactgc | actctggcgt ccctgctagg | 240 |
| ttctctggaa | gtggctcagg | gaccgactac | accctgacaa | ttagctccct ggagcccgaa | 300 |
| gattacgccg | tgtattttg | ccagcaggga | aatactctgc | cttggacatt cggacagggg | 360 |
| actaaagtgg | aaatcaaacg | aacggtggct | gcaccatctg | tcttcatctt cccgccatct | 420 |
| gatgagcagt | tgaaatctgg | aactgcctct | gttgtgtgcc | tgctgaataa cttctatccc | 480 |
| agagaggcca | aagtacagtg | gaaggtggat | aacgccctcc | aatcgggtaa ctcccaggag | 540 |
| agtgtcacag | agcaggacag | caaggacagc | acctacagcc | tcagcagcac cctgacgctg | 600 |
| agcaaagcag | actacgagaa | acacaaagtc | tacgcctgcg | aagtcaccca tcagggcctg | 660 |
| agctcgcccg | tcacaaagag | cttcaacagg | ggagagtgtt | ag | 702 |